(12) United States Patent
Murakami et al.

(10) Patent No.: US 10,772,787 B2
(45) Date of Patent: Sep. 15, 2020

(54) ASSISTANCE APPARATUS, ASSISTANCE METHOD, AND RECORDING MEDIUM

(71) Applicant: Panasonic Intellectual Property Management Co., Ltd., Osaka (JP)

(72) Inventors: Kenta Murakami, Osaka (JP); Stephen William John, Nara (JP); Hiroki Takeuchi, Osaka (JP); Shinobu Adachi, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 49 days.

(21) Appl. No.: 16/154,758

(22) Filed: Oct. 9, 2018

(65) Prior Publication Data
US 2019/0117493 A1 Apr. 25, 2019

(30) Foreign Application Priority Data
Oct. 20, 2017 (JP) .................................. 2017-203984

(51) Int. Cl.
*A61H 3/00* (2006.01)
*A61B 5/00* (2006.01)
(Continued)

(52) U.S. Cl.
CPC .......... *A61H 3/008* (2013.01); *A61B 5/1038* (2013.01); *A61B 5/112* (2013.01); *A61B 5/6807* (2013.01);
(Continued)

(58) Field of Classification Search
CPC ... A61B 5/6829; A61B 5/6831; A61B 5/1038; A61B 5/6828; A61B 5/6807; A61B 5/112; A61B 2562/0261; A61B 2562/0219; A61B 2562/0247; A61B 2225/50; A61H 3/008; A61H 1/0262; A61H 2201/1207;
(Continued)

(56) References Cited

U.S. PATENT DOCUMENTS

| 4,135,714 A * | 1/1979 | Hughes | A63B 21/04 473/229 |
| 4,328,965 A * | 5/1982 | Hatfield | A63B 21/025 124/23.1 |

(Continued)

FOREIGN PATENT DOCUMENTS

| JP | 2009-213538 | 9/2009 |
| JP | 2016-528940 | 9/2016 |

*Primary Examiner* — Garrett K Atkinson
(74) *Attorney, Agent, or Firm* — Wenderoth, Lind & Ponack, L.L.P.

(57) ABSTRACT

An assistance apparatus includes a first and second wires coupling an upper-body belt and a left knee belt to each other on or above a front and back parts of a body of a user, respectively, a third and fourth wires coupling the upper-body belt and a right knee belt to each other on or above the front and back parts, respectively, a motor, a first sensor that detects at least tensions of the first and third wires, and a control circuit. The control circuit controls the motor to generate, when the first wire is broken, in the second wire, a tension less than a tension of the second wire during no break in the first wire, and to generate, when the third wire is broken, in the fourth wire, a tension less than a tension of the fourth wire during no break in the third wire.

27 Claims, 35 Drawing Sheets

(51) Int. Cl.
*A61H 1/02* (2006.01)
*A61B 5/103* (2006.01)
*A61B 5/11* (2006.01)
*A61F 5/01* (2006.01)

(52) U.S. Cl.
CPC .......... *A61B 5/6828* (2013.01); *A61B 5/6829* (2013.01); *A61B 5/6831* (2013.01); *A61H 1/0262* (2013.01); *A61B 2562/0219* (2013.01); *A61B 2562/0247* (2013.01); *A61B 2562/0261* (2013.01); *A61F 2005/0155* (2013.01); *A61F 2005/0188* (2013.01); *A61H 2003/007* (2013.01); *A61H 2201/1207* (2013.01); *A61H 2201/14* (2013.01); *A61H 2201/16* (2013.01); *A61H 2201/1642* (2013.01); *A61H 2201/1652* (2013.01); *A61H 2201/5025* (2013.01); *A61H 2201/5061* (2013.01); *A61H 2201/5079* (2013.01); *A61H 2201/5084* (2013.01); *A61H 2230/60* (2013.01); *A63B 2225/50* (2013.01)

(58) Field of Classification Search
CPC ........ A61H 2201/5079; A61H 2201/16; A61H 2201/5084; A61H 2201/5061; A61H 2201/5025; A61H 2201/14; A61H 2230/60; A61H 2003/007; A61H 2201/1642; A61H 2201/1652; A61H 3/00; A61H 2201/5007; A61H 2003/005; A61F 2005/0188; A61F 2005/0155
See application file for complete search history.

(56) References Cited

U.S. PATENT DOCUMENTS

| | | | | |
|---|---|---|---|---|
| 4,685,670 A * | 8/1987 | Zinkin | ............ | A63B 21/04 482/129 |
| 4,779,866 A * | 10/1988 | Marshall | ............ | A63B 21/16 482/116 |
| 4,961,573 A * | 10/1990 | Wehrell | ............ | A63B 21/0552 482/124 |
| 4,979,733 A * | 12/1990 | Prud'Hon | ............ | A63B 21/0058 482/4 |
| 5,090,694 A * | 2/1992 | Pauls | ............ | A63B 21/015 482/118 |
| 5,147,265 A * | 9/1992 | Pauls | ............ | A63B 21/015 482/115 |
| 5,226,867 A * | 7/1993 | Beal | ............ | A63B 21/153 482/120 |
| 5,382,212 A * | 1/1995 | Davenport | ............ | A63B 21/04 482/121 |
| 5,486,149 A * | 1/1996 | Smith | ............ | A63B 21/015 482/120 |
| 5,586,962 A * | 12/1996 | Hallmark | ............ | A63B 21/04 482/123 |
| 5,618,249 A * | 4/1997 | Marshall | ............ | A63B 21/153 482/115 |
| 5,733,231 A * | 3/1998 | Corn | ............ | A63B 21/025 482/120 |
| 6,436,006 B1 * | 8/2002 | Zemlyakov | ............ | A63B 21/0083 482/112 |
| 6,440,044 B1 * | 8/2002 | Francis | ............ | A63B 21/0455 482/114 |
| 6,685,602 B2 * | 2/2004 | Colosky, Jr. | ............ | A63B 21/025 482/122 |
| 6,929,589 B1 * | 8/2005 | Bruggemann | ............ | A63B 21/025 482/121 |
| 7,462,141 B1 * | 12/2008 | Raboin | ............ | A63B 21/225 482/110 |
| 7,871,359 B2 * | 1/2011 | Humble | ............ | A63B 21/153 242/375.1 |
| 7,878,955 B1 * | 2/2011 | Ehrlich | ............ | A63B 21/025 482/127 |
| 8,002,677 B2 * | 8/2011 | Dibble | ............ | A63B 21/045 482/127 |
| 9,320,936 B1 * | 4/2016 | Rea | ............ | A63B 21/4009 |
| 9,700,751 B2 * | 7/2017 | Verdi | ............ | A63B 21/4019 |
| 10,022,287 B2 * | 7/2018 | Shimada | ............ | A63B 69/0028 |
| 2002/0025891 A1 * | 2/2002 | Colosky, Jr. | ............ | A63B 21/025 482/127 |
| 2005/0181915 A1 * | 8/2005 | Hoecht | ............ | A63B 21/023 482/127 |
| 2010/0130338 A1 * | 5/2010 | Wehrell | ............ | A63B 21/4007 482/124 |
| 2017/0202724 A1 * | 7/2017 | De Rossi | ............ | A61H 3/00 |

* cited by examiner

LEFT LEG FLEXION
110a1 → HIGH TENSION

RIGHT LEG FLEXION
110a3 → HIGH TENSION

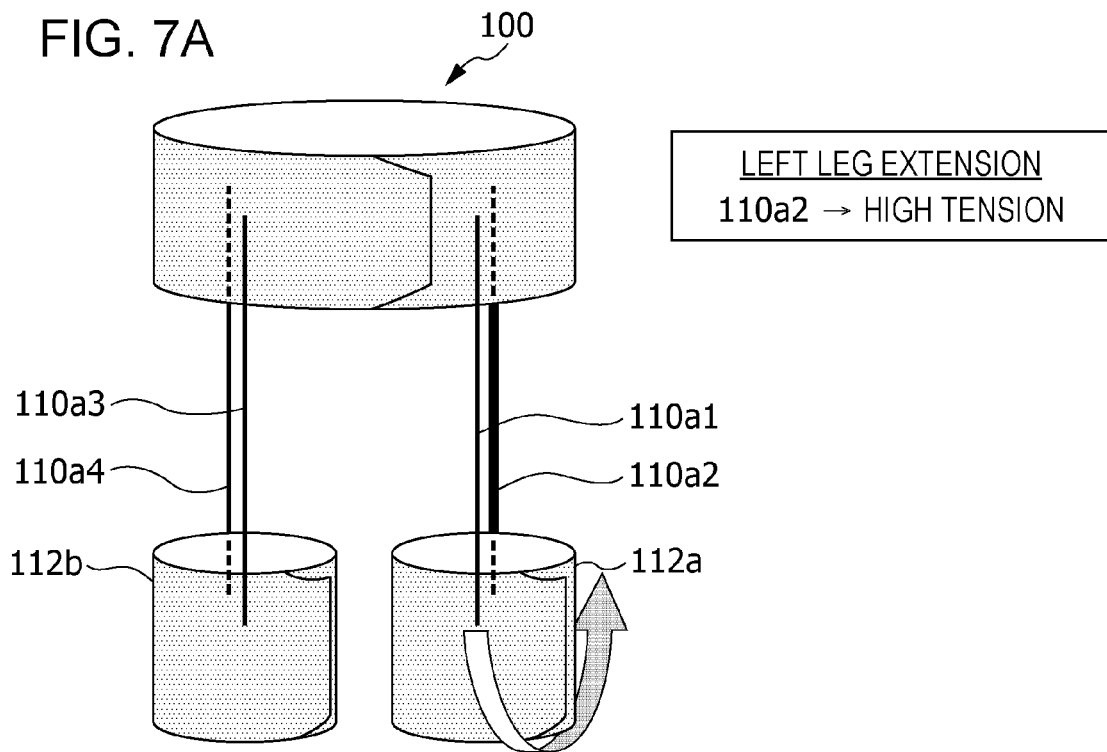
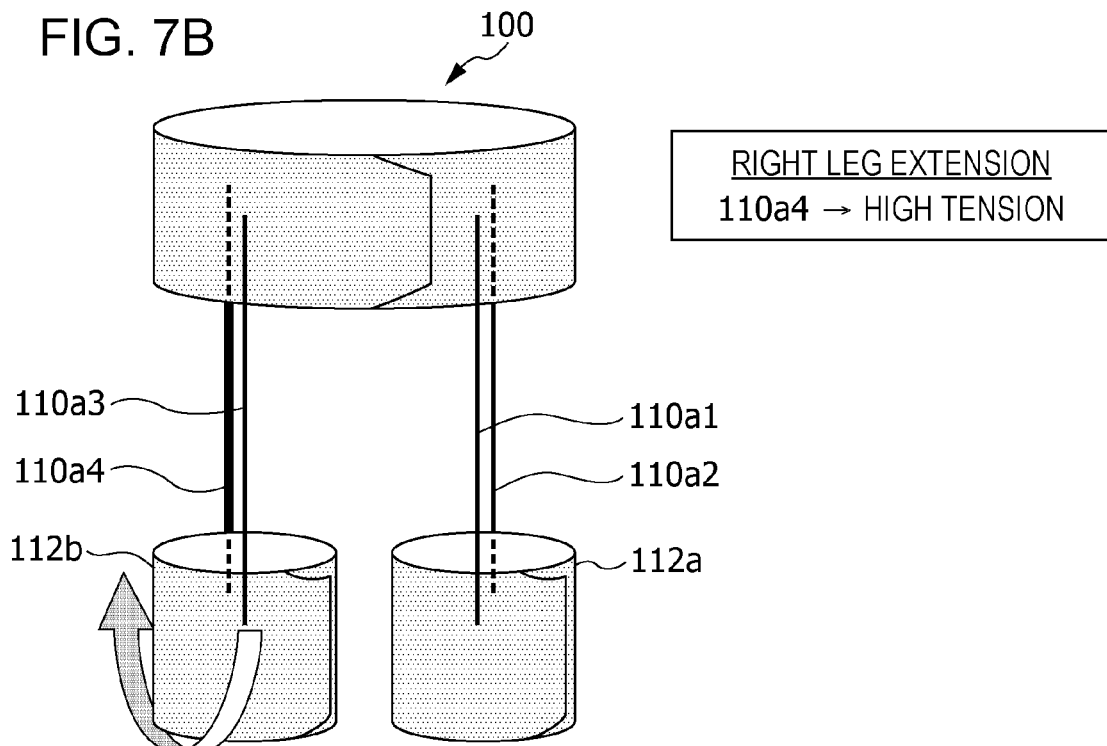

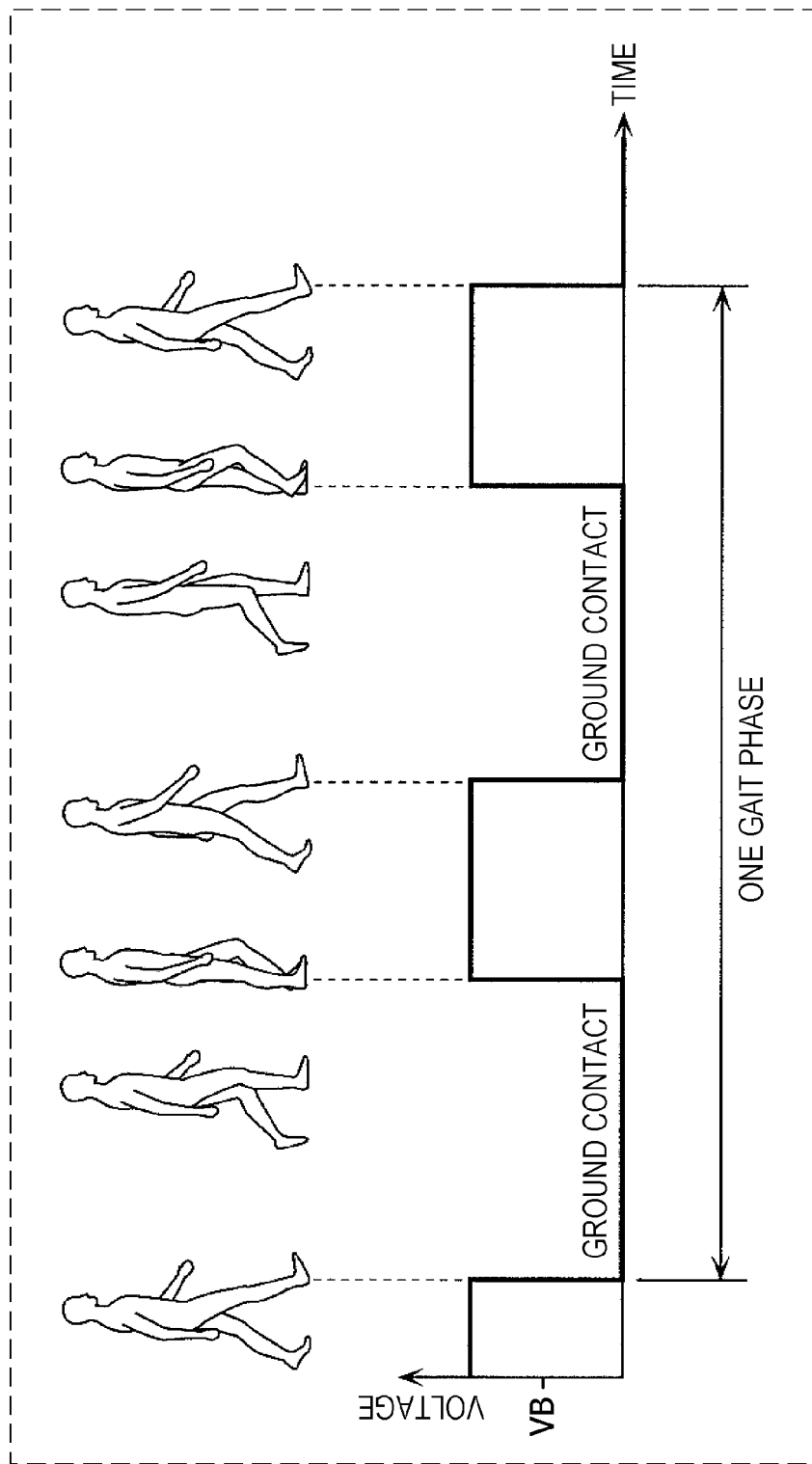

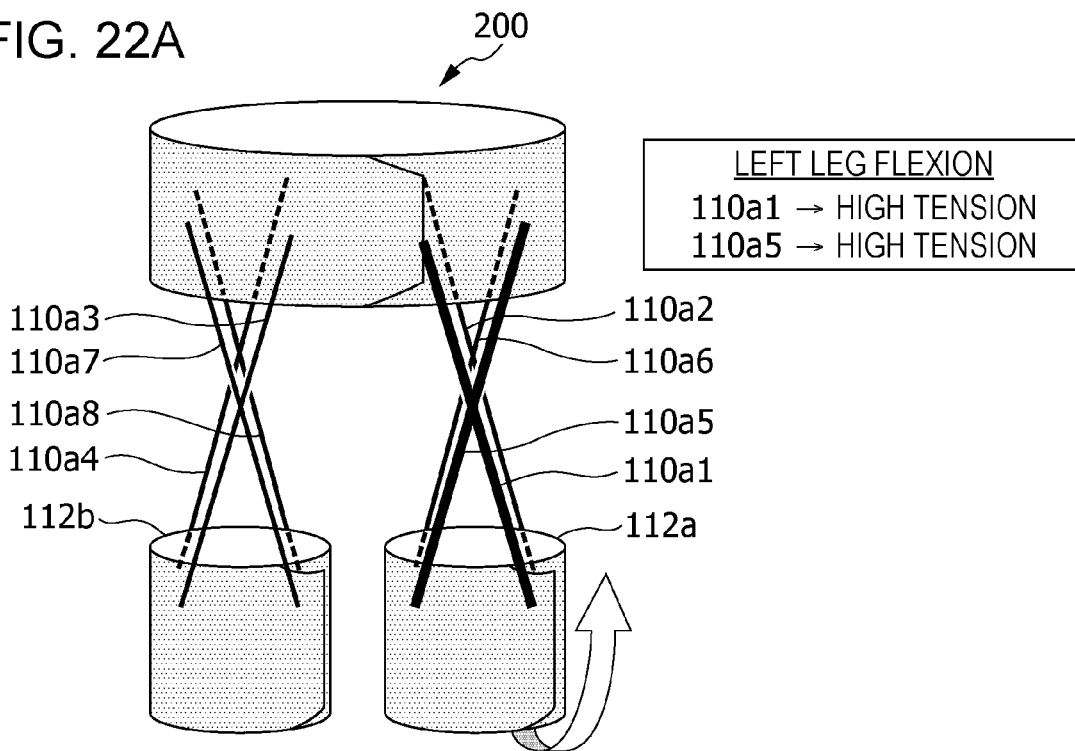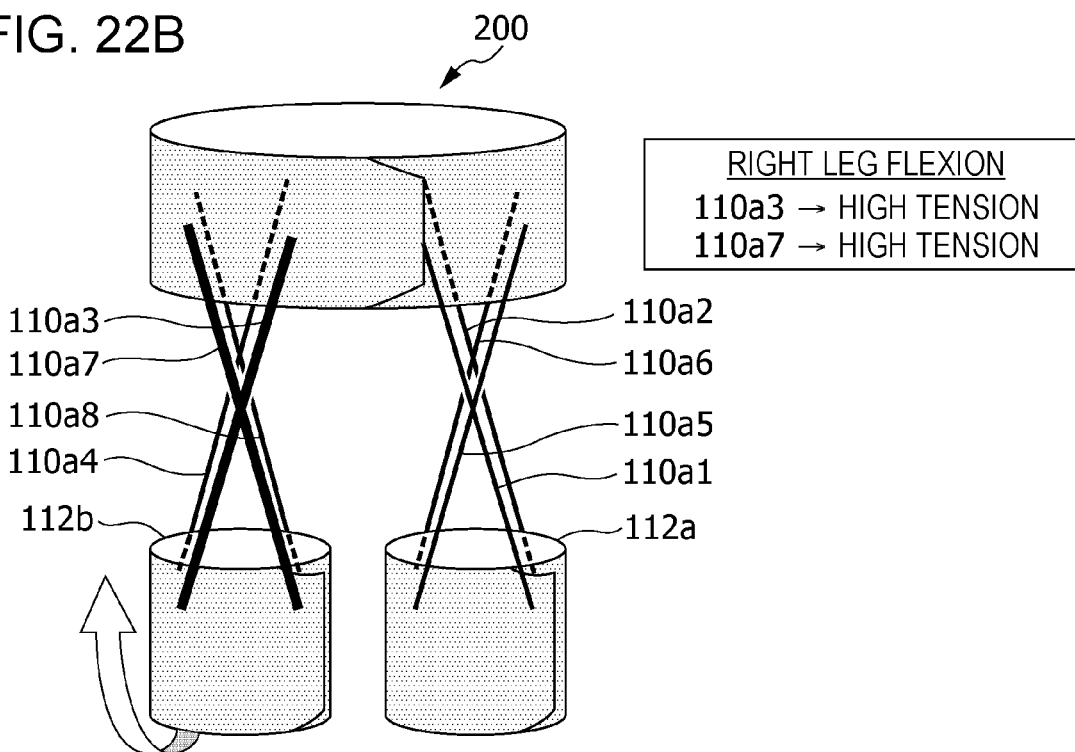

ASSISTANCE APPARATUS, ASSISTANCE METHOD, AND RECORDING MEDIUM

BACKGROUND

1. Technical Field

The present disclosure relates to an assistance apparatus, an assistance method, and a recording medium for assisting a wearer in walking.

2. Description of the Related Art

For example, Japanese Unexamined Patent Application Publication No. 2009-213538 discloses an assistant outfit for assisting movements of joints of a user. The disclosed assistant outfit includes a thigh link to be attached to a thigh, a thigh restraint band that restrains movement of the thigh link, a lower-leg link to be attached to a lower leg, a lower-leg restraint band that restrains movement of the lower-leg link, and a knee assistant motor that changes the angle between the thigh link and the lower-leg link. Japanese Unexamined Patent Application Publication (Translation of PCT Application) No. 2016-528940 discloses a soft exosuit equipped with an actuator including an operating member. In the soft exosuit, activation of the actuator generates a moment around a joint of a user wearing the soft exosuit to assist the movement of the user.

SUMMARY

A need exists to provide assistance for movements of a user in different ways in accordance with the state of the user, such as whether the user is carrying an object such as luggage. A specific method for addressing this issue is not described in Japanese Unexamined Patent Application Publication No. 2009-213538 or Japanese Unexamined Patent Application Publication (Translation of PCT Application) No. 2016-528940.

One non-limiting and exemplary embodiment provides an assistance apparatus, an assistance method, and a recording medium that provide assistance in accordance with the state of a user.

In one general aspect, the techniques disclosed here feature an assistance apparatus including an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, at least one motor, a first sensor that detects at least a tension of the first wire and a tension of the third wire, and a control circuit. In first assistance for assisting the user in walking without an object, the control circuit controls the at least one motor to generate (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, (iv) a tension greater than or equal to the first threshold value in the fourth wire during a fourth period, the fourth period being a period of 0% or more and 25% or less and 65% or more and less than 100% of the gait phase of the right leg, (v) a tension less than a second threshold value in the first wire during a fifth period, the fifth period being a period of 0% or more and less than 100% of the gait phase of the left leg, except the first period, (vi) a tension less than the second threshold value in the second wire during a sixth period, the sixth period being a period of 0% or more and less than 100% of the gait phase of the left leg, except the second period, (vii) a tension less than the second threshold value in the third wire during a seventh period, the seventh period being a period of 0% or more and less than 100% of the gait phase of the right leg, except the third period, and (viii) a tension less than the second threshold value in the fourth wire during an eighth period, the eighth period being a period of 0% or more and less than 100% of the gait phase of the right leg, except the fourth period. The first threshold value is larger than the second threshold value. The control circuit detects at least a break in the first wire and a break in the third wire based on a sensor value of the first sensor. In response to detection of a break in the first wire, the control circuit controls the at least one motor to generate a tension in the second wire during the second period that appears first after a timing of the break in the first wire, the tension being less than a tension of the second wire in a period during which no break occurs in the first wire. In response to detection of a break in the third wire, the control circuit controls the at least one motor to generate a tension in the fourth wire during the fourth period that appears first after a timing of the break in the third wire, the tension being less than a tension of the fourth wire in a period during which no break occurs in the third wire.

It should be noted that general or specific embodiments may be implemented as a system, an apparatus, a method, an integrated circuit, a computer program, a computer-readable recording medium such as a recording disk, or any selective combination thereof. The computer-readable recording medium includes a non-volatile recording medium such as a compact disc-read only memory (CD-ROM).

An assistance apparatus and so on according to aspects of the present disclosure can provide assistance in accordance with the state of a user. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 7A is a diagram illustrating a case where the assistance apparatus according to the embodiment assists extension of the hip joint of the left leg of the user;

FIG. 7B is a diagram illustrating a case where the assistance apparatus according to the embodiment assists extension of the hip joint of the right leg of the user;

FIG. 11 is a diagram illustrating an example of a signal of a pressure-sensitive sensor;

FIG. 22A is a diagram illustrating a case where the assistance apparatus according to the modification assists flexion of the hip joint of the left leg of the user;

FIG. 22B is a diagram illustrating a case where the assistance apparatus according to the modification assists flexion of the hip joint of the right leg of the user;

DETAILED DESCRIPTION

Figure 1:
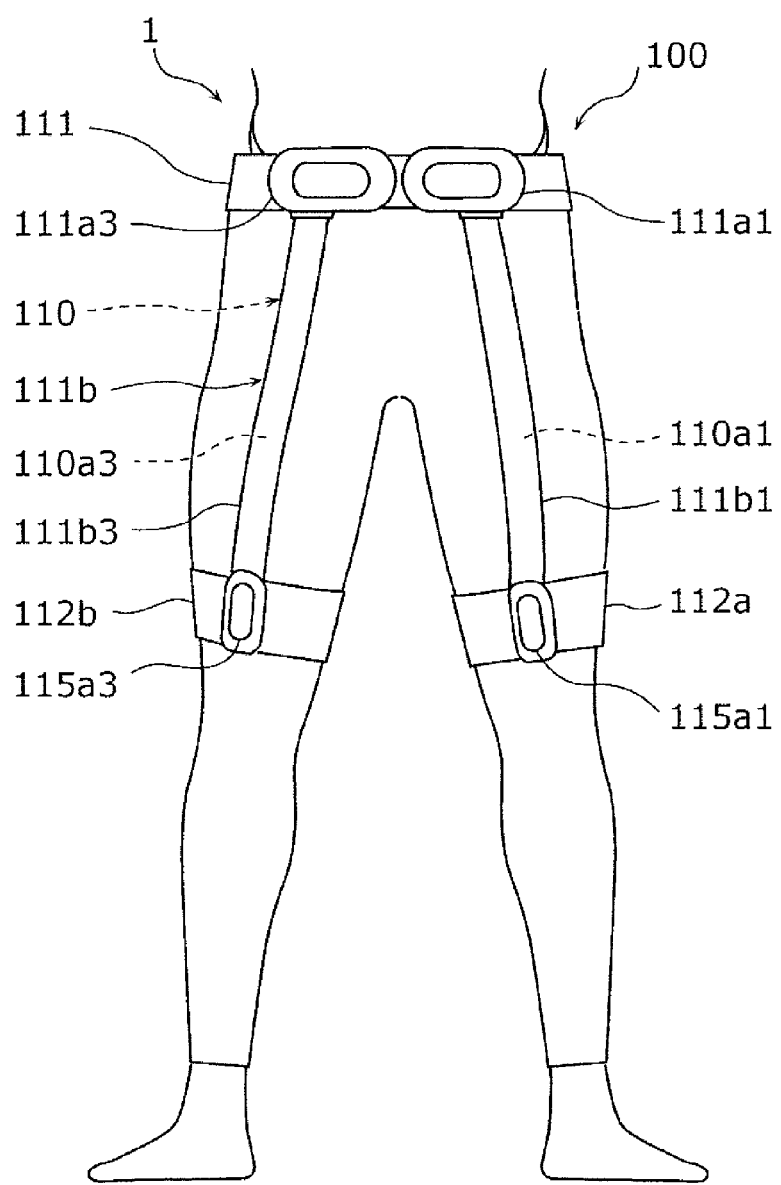
FIG. 1 is a front view of a user wearing an assistance apparatus according to an embodiment, as viewed from the front.

Underlying Knowledge Forming Basis of the Present Disclosure

The inventors of the present disclosure, or the present inventors, have studied the techniques described in Japanese Unexamined Patent Application Publication No. 2009-213538 (hereinafter referred to as "Patent Literature 1") and Japanese Unexamined Patent Application Publication (Translation of PCT Application) No. 2016-528940 (hereinafter referred to as "Patent Literature 2") mentioned in the "BACKGROUND" section and have examined techniques for supporting, or assisting, a user in walking. The present inventors have focused on changing states of a user, who is a wearer of an assistance apparatus. For example, it is necessary that an assistance method for a user who is carrying an object such as luggage be different from an assistance method for a user who is carrying no object.

First, the present inventors have examined an assistance apparatus that assists a user in walking by applying forces generated by motors to the user through wires. To enable various kinds of assistance on the legs of a user, the present inventors have developed an assistance apparatus including wires, each of which is to be placed so as to extend across one of the front of the hip joint of the left leg of the user, the back of the hip joint of the left leg of the user, the front of the hip joint of the right leg of the user, and the back of the hip joint of the right leg of the user. The present inventors have further developed a configuration in which the wires are each coupled to an upper-body belt and a left knee belt or a right knee belt, which are to be attached to the body of the user, and are accordingly attached to the body of the user. Thus, the present inventors have devised an assistance apparatus having a simple configuration.

For example, Patent Literature 1 discloses an assistant outfit including a rod-shaped thigh link that is attached to a side portion of a thigh, and a rod-shaped lower-leg link that is attached to a side portion of a lower leg. The thigh link and the lower-leg link are coupled to a knee assistant motor. The knee assistant motor is driven to change the angle defined by the thigh link and the lower-leg link, and accordingly the assistant outfit assists flexion and extension of the knee of the user. The thigh link, the lower-leg link, and the knee assistant motor are attached to each of the side portion of the right leg of the user and the side portion of the left leg of the user, resulting in the assistant outfit disclosed in Patent Literature 1 having a structure that is large-scale and complicated for the user. Thus, the assistant outfit places a heavy burden on the user.

In Patent Literature 2, tension is applied to connection elements of the soft exosuit, which is worn on a part of the body of the user from the waist to a thigh and a lower leg, through a cable placed at the front part of the thigh of the user, thereby assisting flexion and extension of the knee of the user. In the soft exosuit disclosed in Patent Literature 2, the connection elements and so on, which are attached to the body of the user, are large-scale and complicated for the user. Thus, the soft exosuit places a heavy burden on the user.

In addition, none of Patent Literatures 1 and 2 discloses the details of a method for providing assistance in accordance with the state of a user. Accordingly, the present inventors have devised the following technique for providing assistance in accordance with the state of a user by using the assistance apparatus having a simple configuration described above.

An assistance apparatus according to an aspect of the present disclosure includes an upper-body belt to be worn on an upper half of a body of a user, a left knee belt to be worn on a left knee of the user, a right knee belt to be worn on a right knee of the user, a first wire that couples the upper-body belt and the left knee belt to each other on or above a front part of the body of the user, a second wire that couples the upper-body belt and the left knee belt to each other on or above a back part of the body of the user, a third wire that couples the upper-body belt and the right knee belt to each other on or above the front part of the body of the user, a fourth wire that couples the upper-body belt and the right knee belt to each other on or above the back part of the body of the user, at least one motor, a first sensor that detects at least a tension of the first wire and a tension of the third wire, and a control circuit. In first assistance for assisting the user in walking without an object, the control circuit controls the at least one motor to generate (i) a tension greater than or equal to a first threshold value in the first wire during a first period, the first period being a period of 35% or more and 90% or less of a gait phase of a left leg of the user, (ii) a tension greater than or equal to the first threshold value in the second wire during a second period, the second period being a period of 0% or more and 25% or less and 65% or more and less than 100% of the gait phase of the left leg, (iii) a tension greater than or equal to the first threshold value in the third wire during a third period, the third period being a period of 35% or more and 90% or less of a gait phase of a right leg of the user, (iv) a tension greater than or equal to the first threshold value in the fourth wire during a fourth period, the fourth period being a period of 0% or more and 25% or less and 65% or more and less than 100% of the gait phase of the right leg, (v) a tension less than a second threshold value in the first wire during a fifth period, the fifth period being a period of 0% or more and less than 100% of the gait phase of the left leg, except the first period, (vi) a tension less than the second threshold value in the second wire during a sixth period, the sixth period being a period of 0% or more and less than 100% of the gait phase of the left leg, except the second period, (vii) a tension less than the second threshold value in the third wire during a seventh period, the seventh period being a period of 0% or more and less than 100% of the gait phase of the right leg, except the third period, and (viii) a tension less than the second threshold value in the fourth wire during an eighth period, the eighth period being a period of 0% or more and less than 100% of the gait phase of the right leg, except the fourth period. The first threshold value is larger than the second threshold value. The control circuit detects at least a break in the first wire and a break in the third wire based on a sensor value of the first sensor. In response to detection of a break in the first wire, the control circuit controls the at least one motor to generate a tension in the second wire during the second period that appears first after a timing of the break in the first wire, the tension being less than a tension of the second wire in a period during which no break occurs in the first wire. In response to detection of a break in the third wire, the control circuit controls the at least one motor to generate a tension in the fourth wire during the fourth period that appears first after a timing of the break in the third wire, the tension being less than a tension of the fourth wire in a period during which no break occurs in the third wire.

In the configuration described above, the tension generated in the first wire can apply an assistance force for flexion to the left leg of the user, and the tension generated in the third wire can apply an assistance force for flexion to the right leg of the user. The tension generated in the second wire can apply an assistance force for extension to the left leg of the user, and the tension generated in the fourth wire can apply an assistance force for extension to the right leg of the user. In response to detection of a break in the first wire, the assistance apparatus reduces the tension to be generated in the second wire during the initial second period thereafter to a level smaller than that in a period during which no break occurs in the first wire. In response to detection of a break in the third wire, the assistance apparatus reduces the tension to be generated in the fourth wire during the initial fourth period thereafter to a level smaller than that in a period during which no break occurs in the third wire. Accordingly, the assistance apparatus weakens the assistance force for extension to be applied for the first time after a wire break to a leg for which a wire for assisting flexion is broken, compared with that before the wire break. If a wire break suddenly stops exerting an assistance force on the left or right leg, the user is likely to disrupt the balance between the movements of the left and right legs and can fall. Weakening the assistance force to be applied for the first time after the break to a leg of the user having a broken wire may prevent the user from disrupting the balance between the movements of the left and right legs. Thus, the assistance apparatus can provide assistance to the user in accordance with the state of the user. The first threshold value may be a tension value that allows the user to recognize that the movement of a leg is promoted by a tension generated in a wire, and may be 40 newtons (N), for example. The second threshold value may be a tension value that is not perceivable by the user. The second threshold value may be a tension value that prevents a wire from loosening, and may be a value that is 0.2 to 0.4 times the first threshold value or 10 N, for example.

In the assistance apparatus according to the aspect of the present disclosure, in second assistance for assisting the user in walking with an object, the control circuit may control the at least one motor to generate (i) a tension less than the second threshold value in the first wire during the fifth period, (ii) a tension greater than or equal to the second threshold value in the second wire during the sixth period, (iii) a tension less than the second threshold value in the third wire during the seventh period, and (iv) a tension greater than or equal to the second threshold value in the fourth wire during the eighth period. The tension of the second wire in the sixth period during the second assistance may be greater than the tension of the second wire in the sixth period during the first assistance. The tension of the fourth wire in the eighth period during the second assistance may be greater than the tension of the fourth wire in the eighth period during the first assistance.

In the configuration described above, the assistance apparatus generates a tension greater than or equal to the first threshold value in the first wire during the first period in the gait phase of the left leg to assist flexion of the left leg, and generates a tension greater than or equal to the first threshold value in the third wire during the third period in the gait phase of the right leg to assist flexion of the right leg, thereby assisting the user in walking. Further, the assistance apparatus sets the tension of the first wire to be less than the second threshold value during the fifth period in the gait phase of the left leg and sets the tension of the third wire to be less than the second threshold value during the seventh period in the gait phase of the right leg to weaken assistance for flexion or stop assisting flexion, thereby reducing an influence on extension of the legs. Further, the assistance apparatus generates a tension greater than or equal to the first threshold value in the second wire during the second period in the gait phase of the left leg to assist extension of the left leg, and generates a tension greater than or equal to the first threshold value in the fourth wire during the fourth period in the gait phase of the right leg to assist extension of the right leg, thereby assisting the user in walking. Further, the assistance apparatus sets the tension of the second wire to be greater than or equal to the second threshold value during the sixth period in the gait phase of the left leg to assist extension of the left leg, and sets the tension of the fourth wire to be greater than or equal to the second threshold value during the eighth period in the gait phase of the right leg to assist extension of the right leg. This may keep the center of gravity of the body of the user, who is carrying an object, at the position in the upright posture of the user. Thus, the assistance apparatus can assist a user in walking with an object while keeping the user in a stable posture. In addition, the assistance apparatus weakens, also for a user walking with an object, the assistance force for extension to be applied for the first time after a wire break to a leg for which a wire for assisting flexion is broken, compared with that before the wire break.

In the assistance apparatus according to the aspect of the present disclosure, the control circuit may control the at least one motor to generate (i) a tension in the second wire during the second period that appears second after the timing of the break in the first wire, the tension being equal to the tension of the second wire in the period during which no break occurs in the first wire, and (ii) a tension in the fourth wire during the fourth period that appears second after the timing of the break in the third wire, the tension being equal to the tension of the fourth wire in the period during which no break occurs in the third wire.

In the configuration described above, the assistance apparatus sets the wire tension for extension to be applied for the second time to a leg, for which a wire for assisting flexion is broken, after a wire break occurs, that is, an assistance force, to be the same as that before the wire break. The timing at which a wire tension for extension is applied for the second time after a wire break occurs corresponds to a time point when one or more gait phases elapse after the wire break. At this time point, the user is likely to restore the balance between the movements of the left and right legs to a stable state from an unstable state immediately after the wire break has occurred. Thus, even if an assistance force for extension to be applied to a leg for which a wire is broken is returned to that when there is no wire break, such an assistance force may less affect the body balance of the user. In addition, a uniform and sufficiently strong assistance force for extension is applied to the left and right legs of the user, and thus the user can be stably and sufficiently assisted by the assistance apparatus in walking.

In the assistance apparatus according to the aspect of the present disclosure, the control circuit may control the at least one motor to generate (i) a tension less than the second threshold value in the third wire during the third period after the timing of the break in the first wire, and (ii) a tension less than the second threshold value in the first wire during the first period after the timing of the break in the third wire.

In the configuration described above, if a wire for assisting flexion of one of the left and right legs is broken, the assistance apparatus reduces the tension to be generated in a wire for assisting flexion of the other of the left and right legs to a value less than the second threshold value. This reduces the unbalance in assistance for flexion to be provided to the user between a leg for which a wire is broken and a leg for which no wire is broken. Accordingly, the assistance apparatus can provide assistance with improved balance to the left and right legs of the user.

In the assistance apparatus according to the aspect of the present disclosure, the left leg may shift from a stance phase to a swing phase during the first period, the left leg may shift from the swing phase to the stance phase during the second period, the right leg may shift from the stance phase to the swing phase during the third period, and the right leg may shift from the swing phase to the stance phase during the fourth period.

In the configuration described above, the assistance apparatus assists flexion during the first period in which the left leg shifts from the stance phase to the swing phase, and assists flexion during the third period in which the right leg shifts from the stance phase to the swing phase. Thus, the assistance apparatus can effectively assist the user in walking. Further, the assistance apparatus assists extension during the second period in which the left leg shifts from the swing phase to the stance phase, and assists extension during the fourth period in which the right leg shifts from the swing phase to the stance phase. Thus, the assistance apparatus can effectively assist the user in walking.

In the assistance apparatus according to the aspect of the present disclosure, in the second assistance, the tension of the first wire in the fifth period may be less than the tension of the second wire in the sixth period, and the tension of the third wire in the seventh period may be less than the tension of the fourth wire in the eighth period.

In the configuration described above, in the second assistance, the tension of the first wire during the fifth period in the gait phase of the left leg can be prevented from affecting assistance for extension with the tension of the second wire during the sixth period in the gait phase of the left leg. Further, the tension of the third wire during the seventh period in the gait phase of the right leg can be prevented from affecting assistance for extension with the tension of the fourth wire during the eighth period in the gait phase of the right leg. Accordingly, the assistance apparatus can effectively maintain the center of gravity of the body of the user, who is carrying an object, at the position in the upright posture of the user.

In the assistance apparatus according to the aspect of the present disclosure, the at least one motor may include a first motor, a second motor, a third motor, and a fourth motor. The first wire may have a first end fixed to the left knee belt. The first wire may have a second end fixed to the first motor. The second wire may have a first end fixed to the left knee belt. The second wire may have a second end fixed to the second motor. The third wire may have a first end fixed to the right knee belt. The third wire may have a second end fixed to the third motor. The fourth wire may have a first end fixed to the right knee belt. The fourth wire may have a second end fixed to the fourth motor.

In the configuration described above, the assistance apparatus can separately control the respective tensions of the first wire, the second wire, the third wire, and the fourth wire. Thus, the assistance apparatus can provide fine assistance.

The assistance apparatus according to the aspect of the present disclosure may further include a fifth wire that couples the upper-body belt and the left knee belt to each other and that extends on or above the front part of the body of the user in a direction crossing a direction in which the first wire extends, a sixth wire that couples the upper-body belt and the left knee belt to each other and that extends on or above the back part of the body of the user in a direction crossing a direction in which the second wire extends, a seventh wire that couples the upper-body belt and the right knee belt to each other and that extends on or above the front part of the body of the user in a direction crossing a direction in which the third wire extends, and an eighth wire that couples the upper-body belt and the right knee belt to each other and that extends on or above the back part of the body of the user in a direction crossing a direction in which the fourth wire extends. In the first assistance, the control circuit may control the at least one motor to generate (i) a tension greater than or equal to the first threshold value in the first wire and the fifth wire during the first period, (ii) a tension greater than or equal to the first threshold value in the second wire and the sixth wire during the second period, (iii) a tension greater than or equal to the first threshold value in the third wire and the seventh wire during the third period, (iv) a tension greater than or equal to the first threshold value in the fourth wire and the eighth wire during the fourth period, (v) a tension less than the second threshold value in the first wire and the fifth wire during the fifth period, (vi) a tension less than the second threshold value in the second wire and the sixth wire during the sixth period, (vii) a tension less than the second threshold value in the third wire and the seventh wire during the seventh period, and (viii) a tension less than the second threshold value in the fourth wire and the eighth wire during the eighth period.

In the configuration described above, the tensions generated in the first and fifth wires can apply an assistance force for flexion to the left leg of the user. The tensions generated in the second and sixth wires can apply an assistance force for extension to the left leg of the user. The tensions generated in the third and seventh wires can apply an assistance force for flexion to the right leg of the user. The tensions generated in the fourth and eighth wires can apply an assistance force for extension to the right leg of the user. Thus, the assistance apparatus including the first to eighth wires can provide the first assistance in a way similar to that for the assistance apparatus including the first to fourth wires. In addition, the assistance apparatus including the first to eighth wires separately controls the respective tensions of the first to eighth wires, thereby providing more types of assistance. For example, the tensions generated in the first and fifth wires may be the same or different, and a different type of assistance can be provided in each case.

In the assistance apparatus according to the aspect of the present disclosure, in second assistance for assisting the user in walking with an object, the control circuit may control the at least one motor to generate (i) a tension less than the second threshold value in the first wire during the fifth period, (ii) a tension greater than or equal to the second threshold value in the second wire during the sixth period, (iii) a tension less than the second threshold value in the third wire during the seventh period, and (iv) a tension greater than or equal to the second threshold value in the fourth wire during the eighth period. The tension of the second wire in the sixth period during the second assistance may be greater than the tension of the second wire in the sixth period during the first assistance. The tension of the fourth wire in the eighth period during the second assistance may be greater than the tension of the fourth wire in the eighth period during the first assistance. In the second assistance, the control circuit may control the at least one motor to generate (i) a tension less than the second threshold value in the first wire and the fifth wire during the fifth period, (ii) a tension greater than or equal to the second threshold value in the second wire and the sixth wire during the sixth period, (iii) a tension less than the second threshold value in the third wire and the seventh wire during the seventh period, and (iv) a tension greater than or equal to the second threshold value in the fourth wire and the eighth wire during the eighth period.

In the configuration described above, the assistance apparatus including the first to eighth wires can provide the second assistance in a way similar to that for the assistance apparatus including the first to fourth wires.

In the assistance apparatus according to the aspect of the present disclosure, a time point of 50% of the gait phase of the left leg may correspond to a time point of 0% of the gait phase of the right leg, and a time point of 50% of the gait phase of the right leg may correspond to a time point of 0% of the gait phase of the left leg.

The assistance apparatus according to the aspect of the present disclosure may further include a memory. The memory may store a program for controlling the at least one motor. The control circuit may control the at least one motor in accordance with the program.

The assistance apparatus according to the aspect of the present disclosure may further include a second sensor that detects a gait cycle of the user. The control circuit may calculate the gait phase of the left leg and the gait phase of the right leg based on a sensor value of the second sensor.

In the configuration described above, the assistance apparatus can assist the user in walking on the basis of a gait phase corresponding to a gait cycle of the user. Accordingly, the assistance apparatus can provide assistance based on actual user walking.

The assistance apparatus according to the aspect of the present disclosure may further include an interface device. The control circuit may accept selection of an assistance method including the first assistance via the interface device. The control circuit may control the at least one motor in accordance with the assistance method.

In the configuration described above, the assistance apparatus enables selection of an assistance method desired by the user.

An assistance method according to another aspect of the present disclosure is an assistance method for assisting a movement of a user by using wires attached to a body of the user. The assistance method include coupling, using a first wire among the wires, an upper-body belt and a left knee belt to each other on or above a front part of the body of the user, the upper-body belt being a belt to be worn on an upper half of the body of the user, the left knee belt being a belt to be worn on a left knee of the user; coupling, using a second wire among the wires, the upper-body belt and the left knee belt to each other on or above a back part of the body of the user; coupling, using a third wire among the wires, the upper-body belt and a right knee belt to each other on or above the front part of the body of the user, the right knee belt being a belt to be worn on a right knee of the user; coupling, using a fourth wire among the wires, the upper-body belt and the right knee belt to each other on or above the back part of the body of the user; in first assistance for assisting the user in walking without an object, generating a tension greater than or equal to a first threshold value in the first wire during a first period, the first period being a period of 35% or more and 90% or less of a gait phase of a left leg of the user; generating a tension greater than or equal to the first threshold value in the second wire during a second period, the second period being a period of 0% or more and 25% or less and 65% or more and less than 100% of the gait phase of the left leg; generating a tension greater than or equal to the first threshold value in the third wire during a third period, the third period being a period of 35% or more and 90% or less of a gait phase of a right leg of the user; generating a tension greater than or equal to the first threshold value in the fourth wire during a fourth period, the fourth period being a period of 0% or more and 25% or less and 65% or more and less than 100% of the gait phase of the right leg; generating a tension less than a second threshold value in the first wire during a fifth period, the fifth period being a period of 0% or more and less than 100% of the gait phase of the left leg, except the first period; generating a tension less than the second threshold value in the second wire during a sixth period, the sixth period being a period of 0% or more and less than 100% of the gait phase of the left leg, except the second period; generating a tension less than the second threshold value in the third wire during a seventh period, the seventh period being a period of 0% or more and less than 100% of the gait phase of the right leg, except the third period; generating a tension less than the second threshold value in the fourth wire during an eighth period, the eighth period being a period of 0% or more and less than 100% of the gait phase of the right leg, except the fourth period, the first threshold value being larger than the second threshold value; acquiring a sensor value of a first sensor that detects at least a tension of the first wire and a tension of the third wire; in response to detection of a break in the first wire, generating a tension in the second wire during the second period that appears first after a timing of the break in the first wire, the tension being less than a tension of the second wire in a period during which no break occurs in the first wire; and in response to detection of a break in the third wire, generating a tension in the fourth wire during the fourth period that appears first after a timing of the break in the third wire, the tension being less than a tension of the fourth wire in a period during which no break occurs in the third wire. The tension of the first wire, the tension of the second wire, the tension of the third wire, and the tension of the fourth wire are adjusted by a motor that is controlled by at least one control circuit. The assistance method according to the aspect described above can achieve advantages similar to those of the assistance apparatus according to the aspect of the present disclosure.

The assistance method according to the aspect of the present disclosure may further include, in second assistance for assisting the user in walking with an object, generating a tension less than the second threshold value in the first wire during the fifth period; generating a tension greater than or equal to the second threshold value in the second wire during the sixth period; generating a tension less than the second threshold value in the third wire during the seventh period; and generating a tension greater than or equal to the second threshold value in the fourth wire during the eighth period. The tension of the second wire in the sixth period during the second assistance may be greater than the tension of the second wire in the sixth period during the first assistance. The tension of the fourth wire in the eighth period during the second assistance may be greater than the tension of the fourth wire in the eighth period during the first assistance.

The assistance method according to the aspect of the present disclosure may further include generating a tension in the second wire during the second period that appears second after the timing of the break in the first wire, the tension being equal to the tension of the second wire in the period during which no break occurs in the first wire; and generating a tension in the fourth wire during the fourth period that appears second after the timing of the break in the third wire, the tension being equal to the tension of the fourth wire in the period during which no break occurs in the third wire.

The assistance method according to the aspect of the present disclosure may further include generating a tension less than the second threshold value in the third wire during the third period after the timing of the break in the first wire; and generating a tension less than the second threshold value in the first wire during the first period after the timing of the break in the third wire.

In the assistance method according to the aspect of the present disclosure, the left leg may shift from a stance phase to a swing phase during the first period, the left leg may shift from the swing phase to the stance phase during the second period, the right leg may shift from the stance phase to the swing phase during the third period, and the right leg may shift from the swing phase to the stance phase during the fourth period.

In the assistance method according to the aspect of the present disclosure, in the second assistance, the tension of the first wire in the fifth period may be less than the tension of the second wire in the sixth period, and the tension of the third wire in the seventh period may be less than the tension of the fourth wire in the eighth period.

In the assistance method according to the aspect of the present disclosure, a first end of the first wire may be fixed to the left knee belt, a second end of the first wire may be fixed to a first motor among the at least one motor, a first end of the second wire may be fixed to the left knee belt, a second end of the second wire may be fixed to a second motor among the at least one motor, a first end of the third wire may be fixed to the right knee belt, a second end of the third wire may be fixed to a third motor among the at least one motor, a first end of the fourth wire may be fixed to the right knee belt, and a second end of the fourth wire may be fixed to a fourth motor among the at least one motor.

The assistance method according to the aspect of the present disclosure may further include coupling, using a fifth wire among the wires, the upper-body belt and the left knee belt to each other, the fifth wire extending on or above the front part of the body of the user in a direction crossing a direction in which the first wire extends; coupling, using a sixth wire among the wires, the upper-body belt and the left knee belt to each other, the sixth wire extending on or above the back part of the body of the user in a direction crossing a direction in which the second wire extends; coupling, using a seventh wire among the wires, the upper-body belt and the right knee belt to each other, the seventh wire extending on or above the front part of the body of the user in a direction crossing a direction in which the third wire extends; coupling, using an eighth wire among the wires, the upper-body belt and the right knee belt to each other, the eighth wire extending on or above the back part of the body of the user in a direction crossing a direction in which the fourth wire extends; in the first assistance, generating a tension greater than or equal to the first threshold value in the first wire and the fifth wire during the first period; generating a tension greater than or equal to the first threshold value in the second wire and the sixth wire during the second period; generating a tension greater than or equal to the first threshold value in the third wire and the seventh wire during the third period; generating a tension greater than or equal to the first threshold value in the fourth wire and the eighth wire during the fourth period; generating a tension less than the second threshold value in the first wire and the fifth wire during the fifth period; generating a tension less than the second threshold value in the second wire and the sixth wire during the sixth period; generating a tension less than the second threshold value in the third wire and the seventh wire during the seventh period; and generating a tension less than the second threshold value in the fourth wire and the eighth wire during the eighth period.

The assistance method according to the aspect of the present disclosure may further include, in second assistance for assisting the user in walking with an object, generating a tension less than the second threshold value in the first wire during the fifth period; generating a tension greater than or equal to the second threshold value in the second wire during the sixth period; generating a tension less than the second threshold value in the third wire during the seventh period; generating a tension greater than or equal to the second threshold value in the fourth wire during the eighth period, the tension of the second wire in the sixth period during the second assistance being greater than the tension of the second wire in the sixth period during the first assistance, the tension of the fourth wire in the eighth period during the second assistance being greater than the tension of the fourth wire in the eighth period during the first assistance; in the second assistance, generating a tension less than the second threshold value in the first wire and the fifth wire during the fifth period; generating a tension greater than or equal to the second threshold value in the second wire and the sixth wire during the sixth period; generating a tension less than the second threshold value in the third wire and the seventh wire during the seventh period; and generating a tension greater than or equal to the second threshold value in the fourth wire and the eighth wire during the eighth period.

In the assistance method according to the aspect of the present disclosure, a time point of 50% of the gait phase of the left leg may correspond to a time point of 0% of the gait phase of the right leg, and a time point of 50% of the gait phase of the right leg may correspond to a time point of 0% of the gait phase of the left leg.

The assistance method according to the aspect of the present disclosure may further include acquiring a sensor value of a second sensor that detects a gait cycle of the user; and calculating the gait phase of the left leg and the gait phase of the right leg based on the sensor value of the second sensor.

The assistance method according to the aspect of the present disclosure may further include accepting selection of an assistance method including the first assistance via an interface device; and generating a tension in the first wire, the second wire, the third wire, and the fourth wire in accordance with the assistance method.

A recording medium according to still another aspect of the present disclosure is a recording medium storing a control program for causing a device including a processor to execute a process. The recording medium is a non-volatile, computer-readable medium. A first wire couples an upper-body belt and a left knee belt to each other on or above a front part of a body of a user, the upper-body belt being a belt to be worn on an upper half of the body of the user, the left knee belt being a belt to be worn on a left knee of the user. A second wire couples the upper-body belt and the left knee belt to each other on or above a back part of the body of the user. A third wire couples the upper-body belt and a right knee belt to each other on or above the front part of the body of the user, the right knee belt being a belt to be worn on a right knee of the user. A fourth wire couples the upper-body belt and the right knee belt to each other on or above the back part of the body of the user. The process includes when assisting the user in walking without an object, causing at least one motor to generate a tension greater than or equal to a first threshold value in the first wire during a first period, the first period being a period of 35% or more and 90% or less of a gait phase of a left leg of the user; causing the at least one motor to generate a tension greater than or equal to the first threshold value in the second wire during a second period, the second period being a period of 0% or more and 25% or less and 65% or more and less than 100% of the gait phase of the left leg; causing the at least one motor to generate a tension greater than or equal to the first threshold value in the third wire during a third period, the third period being a period of 35% or more and 90% or less of a gait phase of a right leg of the user; causing the at least one motor to generate a tension greater than or equal to the first threshold value in the fourth wire during a fourth period, the fourth period being a period of 0% or more and 25% or less and 65% or more and less than 100% of the gait phase of the right leg; causing the at least one motor to generate a tension less than a second threshold value in the first wire during a fifth period, the fifth period being a period of 0% or more and less than 100% of the gait phase of the left leg, except the first period; causing the at least one motor to generate a tension less than the second threshold value in the second wire during a sixth period, the sixth period being a period of 0% or more and less than 100% of the gait phase of the left leg, except the second period; causing the at least one motor to generate a tension less than the second threshold value in the third wire during a seventh period, the seventh period being a period of 0% or more and less than 100% of the gait phase of the right leg, except the third period; causing the at least one motor to generate a tension less than the second threshold value in the fourth wire during an eighth period, the eighth period being a period of 0% or more and less than 100% of the gait phase of the right leg, except the fourth period, the first threshold value being larger than the second threshold value; acquiring a sensor value of a first sensor that detects at least a tension of the first wire and a tension of the third wire; in response to detection of a break in the first wire, generating a tension in the second wire during the second period that appears first after a timing of the break in the first wire, the tension being less than a tension of the second wire in a period during which no break occurs in the first wire; and in response to detection of a break in the third wire, generating a tension in the fourth wire during the fourth period that appears first after a timing of the break in the third wire, the tension being less than a tension of the fourth wire in a period during which no break occurs in the third wire. The recording medium according to the aspect described above can achieve advantages similar to those of the assistance apparatus according to the aspect of the present disclosure.

It should be noted that the general or specific aspects described above may be implemented as a system, an apparatus, a method, an integrated circuit, a computer program, or a computer-readable recording medium such as a recording disc, or any selective combination thereof. Examples of the computer-readable recording medium include a non-volatile recording medium such as a CD-ROM.

Embodiment

The following specifically describes an assistance apparatus and so on according to an embodiment of the present disclosure with reference to the drawings. The following embodiment describes general or specific examples. Numerical values, shapes, constituent elements, arrangement positions and connection forms of the constituent elements, steps, the order of the steps, and so on in the following embodiment are merely examples and are not intended to limit the present disclosure. The constituent elements mentioned in the following embodiment are described as optional constituent elements unless they are specified in independent claims that define the present disclosure in its broadest concept. The following description of the embodiment may include expressions with the term "approximately", such as approximately parallel or approximately perpendicular. For example, the expression "approximately parallel" is used to mean not only the state of being exactly parallel, that is, the state of being substantially parallel but also the state of being parallel with an error of several percent, for example. This also applies to other expressions with "approximately". In addition, the drawings are illustrative and are not to scale. In the drawings, substantially the same constituent elements are given the same numerals and will not be repeatedly described or will be described in brief.

In this embodiment, an assistance apparatus 100 will be described as an assistance apparatus that assists a user wearing the assistance apparatus 100 in walking. Specifically, the assistance apparatus 100 according to the embodiment will be described as an assistance apparatus that actively supports flexion and extension of the hip joints of the user to allow the user to walk. In this embodiment, the term "actively supporting" may refer not only to supporting flexion and extension forces, which are required for the hip joints, during flexion and extension of the hip joints of the user to walk in the direction of travel but also to applying a force for causing flexion and extension of the hip joints and to physically controlling the amount of flexion and extension of the hip joints to the desired amount of flexion and extension, that is, physically controlling movements of the hip joints of the user. As used herein, the term "assisting the user" by the assistance apparatus 100 is used to include both actively supporting the movement of the user and supporting the movement of the user in an auxiliary manner.

1. Configuration of Assistance Apparatus According to Embodiment

Figure 2:
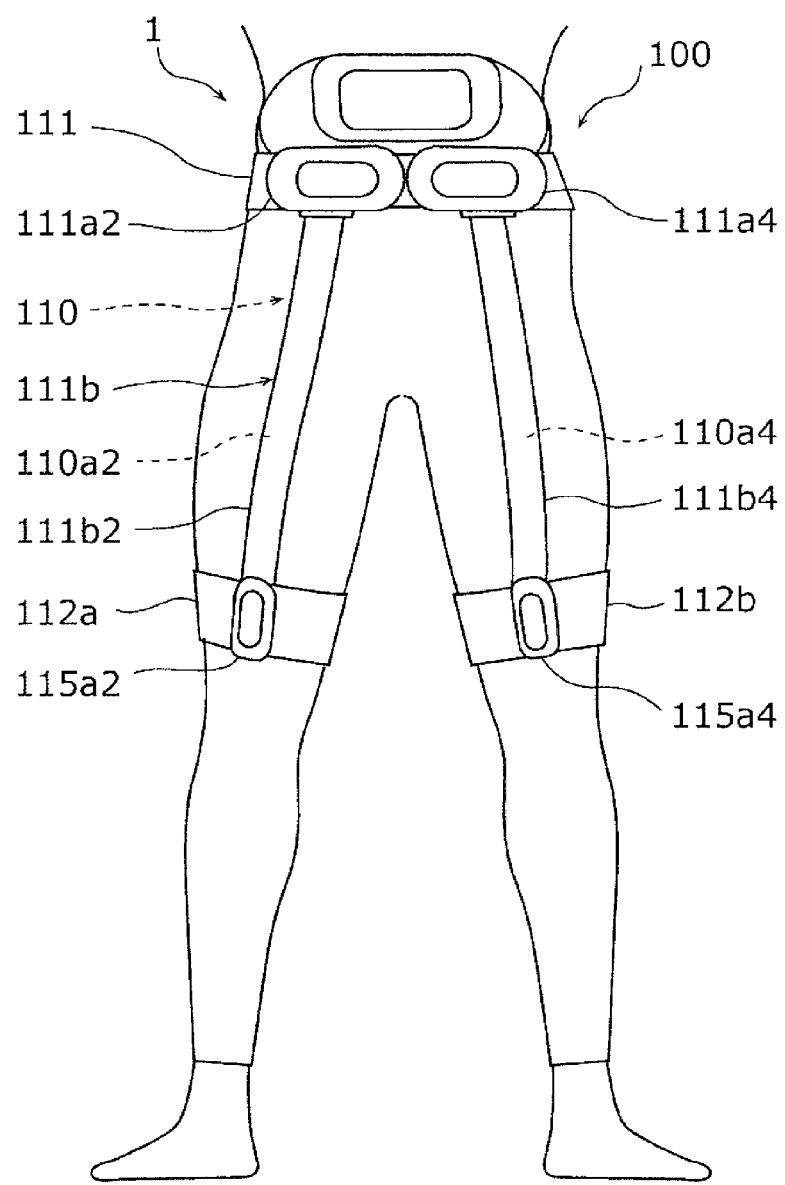
FIG. 2 is a back view of the user wearing the assistance apparatus illustrated in FIG. 1.
Figure 3:
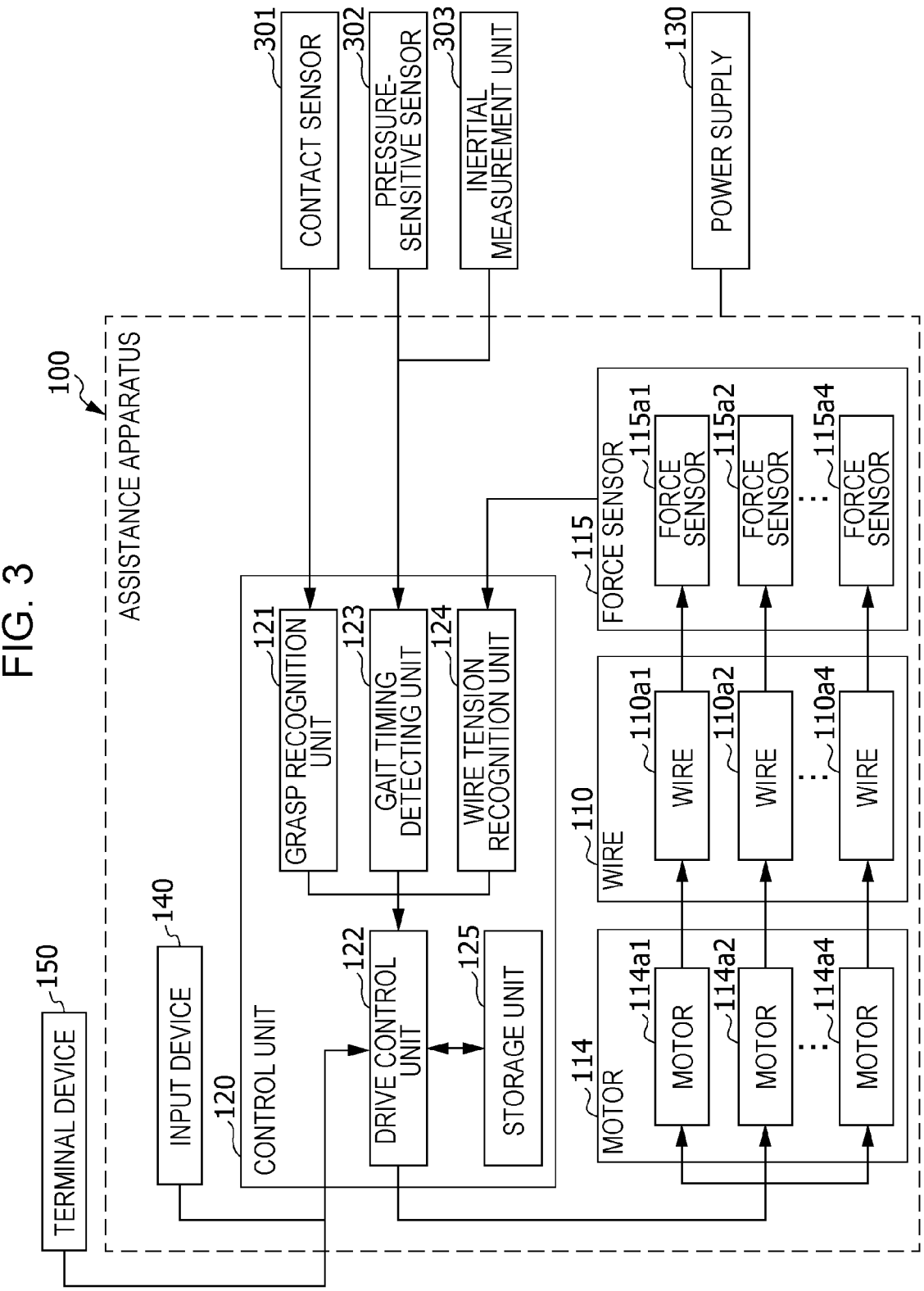
FIG. 3 is a block diagram illustrating a functional configuration of the assistance apparatus according to the embodiment.

The assistance apparatus 100 according to the embodiment will be described with reference to FIG. 1 to FIG. 3. FIG. 1 is a front view of a user 1 wearing the assistance apparatus 100 according to the embodiment, as viewed from the front. FIG. 2 is a back view of the user 1 wearing the assistance apparatus 100 illustrated in FIG. 1. FIG. 3 is a block diagram illustrating a functional configuration of the assistance apparatus 100 according to the embodiment.

As illustrated in FIG. 1 to FIG. 3, the assistance apparatus 100 includes an upper-body belt 111, a left knee belt 112*a*, a right knee belt 112*b*, and wires 110. The assistance apparatus 100 further includes motors 114, force sensors 115, and a control unit 120 that controls the operation of the motors 114. The assistance apparatus 100 may include a power supply 130 for supplying electric power to the motors 114 and so on. The power supply 130 may be, for example, a primary battery, a secondary battery, or the like.

The wires 110 include wires 110*a*1 to 110*a*4. Each of the wires 110 is coupled to the upper-body belt 111 and the left knee belt 112*a* or coupled to the upper-body belt 111 and the right knee belt 112*b*.

The motors 114 include motors 114*a*1 to 114*a*4. The wire 110*a*1 is coupled to the motor 114*a*1. The wire 110*a*2 is coupled to the motor 114*a*2. The wire 110*a*3 is coupled to the motor 114*a*3. The wire 110*a*4 is coupled to the motor 114*a*4.

The force sensors 115 include force sensors 115*a*1 to 115*a*4. The force sensor 115*a*1 is disposed on the wire 110*a*1. The force sensor 115*a*2 is disposed on the wire 110*a*2. The force sensor 115*a*3 is disposed on the wire 110*a*3. The force sensor 115*a*4 is disposed on the wire 110*a*4.

The upper-body belt 111 is worn on the upper half of the body of the user 1. The upper-body belt 111 has a band shape, for example. The upper-body belt 111 includes, near an end portion thereof, a fixing member. Examples of the fixing member include a hook-and-loop fastener such as a Velcro (registered trademark) tape, a fastener such as a hook or a buckle, and a tape. For example, the upper-body belt 111 is wrapped around the waist of the user 1 and is kept wrapped around the waist of the user 1 by using the fixing member. Thus, the upper-body belt 111 is worn on the waist of the user 1. The fixing position of the fixing member is adjusted to change the inner diameter of the wrapped upper-body belt 111. Since the length of the upper-body belt 111 can be adjusted, various users 1 with different waist circumferences can wear the upper-body belt 111. The upper-body belt 111 is made of a non-extensible material, for example. Thus, the upper-body belt 111 is less deformable when pulled by the wires 110. The term "upper half of the body", as used herein, is used to include a portion of the body of the user from the shoulder to the waist. The upper-body belt 111 illustrated in FIG. 1 and FIG. 2 has a configuration of a waist belt to be worn on the waist of the user 1. The upper-body belt 111 may be worn on, for example, the waist of the user 1 and/or the shoulder of the user 1 and/or the chest of the user 1.

The upper-body belt 111 may have a tubular shape. In this case, the tubular-shaped upper-body belt 111 may have a larger circumference than the waist circumference of the user 1. The upper-body belt 111 has an adjustment mechanism for adjusting the length of the upper-body belt 111 so that the upper-body belt 111 fits the waist of the user 1. The adjustment mechanism is, for example, a hook-and-loop fastener and may be configured such that a portion of the hook-and-loop fastener having a hook surface is located on an outer periphery of the tubular shape in such a manner as to branch from the outer periphery and a loop surface of the hook-and-loop fastener is located on an outer peripheral surface of the tubular shape. That is, the upper-body belt 111 folds back at the portion of the hook-and-loop fastener, and the inner diameter of the tube formed by the upper-body belt 111 changes in accordance with the amount of fold-back.

The left knee belt 112a is worn on the left leg of the user 1 in the vicinity of the left knee, and the right knee belt 112b is worn on the right leg of the user 1 in the vicinity of the right knee. The left knee belt 112a may be worn on any portion of the left leg in a region extending from below the knee to the thigh. The right knee belt 112b may be worn on any portion of the right leg in a region extending from below the knee to the thigh. That is, the term "knee", as used herein, may be used to include a region extending from below the knee to the thigh.

Each of the knee belts 112a and 112b has a band shape, for example, and includes, near an end portion thereof, a fixing member. The knee belts 112a and 112b are the knee left belt 112a and the right knee belt 112b. Examples of the fixing member include a hook-and-loop fastener such as a Velcro (registered trademark) tape, a fastener such as a hook or a buckle, and a tape. Each of the knee belts 112a and 112b is worn on a corresponding one of the thighs of the user 1 or above a corresponding one of the knees of the user 1. For example, each of the knee belts 112a and 112b is wrapped around the corresponding one of the thighs or the like of the user 1 and is kept wrapped around the corresponding one of the thighs or the like of the user 1 by using the fixing member. Thus, the knee belts 112a and 112b are worn on the thighs or the like of the user 1. The fixing positions of the fixing members are adjusted to change the respective inner diameters of the wrapped knee belts 112a and 112b. Since the lengths of the knee belts 112a and 112b can be adjusted, various users 1 having different leg circumferences can wear the knee belts 112a and 112b. The knee belts 112a and 112b may not necessarily be worn over the knee joints. The human thigh has a feature in that the diameter of the thigh becomes larger gradually from the knee toward the hip. Thus, the knee belts 112a and 112b, which are worn on the thighs, namely, above the knees, slip just a little even under tensile forces of the wires 110 when the knee belts 112a and 112b are tightly fastened. In addition, the knee belts 112a and 112b are made of a non-extensible material, for example. Thus, the knee belts 112a and 112b are less deformable when pulled by the wires 110.

Each of the knee belts 112a and 112b may have a tubular shape. In this case, the tubular-shaped knee belts 112a and 112b may have larger circumferences than the thighs of the user 1. The knee belts 112a and 112b have each an adjustment mechanism for adjusting the length of the corresponding one of the knee belts 112a and 112b so that the knee belts 112a and 112b fit the thighs or the like of the user 1. Each of the adjustment mechanisms is, for example, a hook-and-loop fastener and may be configured such that a portion of the hook-and-loop fastener having a hook surface is located on an outer periphery of the tubular shape in such a manner as to branch from the outer periphery and a loop surface of the hook-and-loop fastener is located on an outer peripheral surface of the tubular shape. That is, the knee belts 112a and 112b each fold back at the portion of the hook-and-loop fastener, and the inner diameter of the tube formed by each of the knee belts 112a and 112b changes in accordance with the amount of fold-back.

The motors 114 are arranged on the upper-body belt 111 in a fixed manner. In this embodiment, the motors 114 include four motors 114a1 to 114a4. For example, the motors 114a1 to 114a4 may be accommodated in hollow containers 111a1 to 111a4 included in the upper-body belt 111, respectively. The containers 111a1 to 111a4 may be integrated with the upper-body belt 111 or may be removably attached to the upper-body belt 111. The containers 111a1 to 111a4 may be disposed in the manner illustrated in FIG. 1 and FIG. 2. In the example illustrated in FIG. 1 and FIG. 2, the containers 111a1, 111a2, 111a3, and 111a4 are located on the left side of the front part, the left side of the back part, the right side of the front part, and the right side of the back part of the body of the user 1, respectively. The motors 114a1, 114a2, 114a3, and 114a4 are accommodated in the containers 111a1, 111a2, 111a3, and 111a4, respectively. The motor 114a1 changes the length of the wire 110a1 between the upper-body belt 111 and the left knee belt 112a to adjust the tension of the wire 110a1. The motor 114a2 changes the length of the wire 110a2 between the upper-body belt 111 and the left knee belt 112a to adjust the tension of the wire 110a2. The motor 114a3 changes the length of the wire 110a3 between the upper-body belt 111 and the right knee belt 112b to adjust the tension of the wire 110a3. The motor 114a4 changes the length of the wire 110a4 between the upper-body belt 111 and the right knee belt 112b to adjust the tension of the wire 110a4.

In this embodiment, each of the motors 114a1 to 114a4 includes a pulley, a drive shaft for rotating the pulley, and an electric motor for driving the drive shaft to rotate. The pulley of each of the motors 114a1 to 114a4 has a corresponding wire among the wires 110a1 to 110a4 wound therearound. The motors 114a1 to 114a4 and the wires 110a1 to 110a4 have a one-to-one correspondence. The respective pulleys, drive shafts, and electric motors of the motors 114a1 to 114a4 are accommodated in the containers 111a1 to 111a4, respectively. Each of the motors 114a1 to 114a4 may include an electric motor, but may include no pulley or drive shaft. Alternatively, the upper-body belt 111 may include pulleys and drive shafts, each pulley and drive shaft being associated with one of the motors 114a1 to 114a4. In this case, a rotating shaft of the electric motor is coupled to the drive shaft for the pulley in such a manner that a rotational driving force can be transmitted to the drive shaft. Instead of the motors 114a1 to 114a4, for example, a device capable of adjusting the lengths of the wires 110a1 and 110a2 between the upper-body belt 111 and the left knee belt 112a and the lengths of the wires 110a3 and 110a4 between the upper-body belt 111 and the right knee belt 112b, such as a linear actuator or a pneumatic or hydraulic piston, may be used. In the assistance apparatus 100 having the configuration described above, the wound portions of the wires 110a1 to 110a4 and the motors 114a1 to 114a4 are located on the upper-body belt 111, and the wires 110a1 to 110a4 and the knee belts 112a and 112b are located below the upper-body belt 111. Accordingly, the assistance apparatus 100 achieves a simple and compact configuration.

In this embodiment, the wires 110 include four wires 110a1 to 110a4. The motor 114a1 is coupled to the wire 110a1, the motor 114a2 is coupled to the wire 110a2, the motor 114a3 is coupled to the wire 110a3, and the motor 114a4 is coupled to the wire 110a4 so as to individually adjust the lengths of the wires 110a1 to 110a4.

Each of the wires 110a1 and 110a2 has one end fixed to the left knee belt 112a. The wire 110a1 has another end coupled to the motor 114a1, and the wire 110a2 has another end coupled to the motor 114a2. That is, the other end of the wire 110a1 and the other end of the wire 110a2 are fixed. The wire 110a1 couples the left knee belt 112a and the motor 114a1 to each other, and the wire 110a2 couples the left knee belt 112a and the motor 114a2 to each other.

Each of the wires 110a3 and 110a4 has one end fixed to the right knee belt 112b. The wire 110a3 has another end coupled to the motor 114a3, and the wire 110a4 has another end coupled to the motor 114a4. That is, the other end of the wire 110a3 and the other end of the wire 110a4 are fixed. The wire 110a3 couples the right knee belt 112b and the motor 114a3 to each other, and the wire 110a4 couples the right knee belt 112b and the motor 114a4 to each other.

In this embodiment, each of the motors 114a1 to 114a4 rotates the pulley in the forward or reverse direction to wind or unwind the corresponding wire among the wires 110a1 to the 110a4 around the pulley. The wires 110a1 to 110a4 described above are fixed to the waist of the user 1 by the upper-body belt 111 and are fixed to the left and right thighs or the like of the user 1 by the knee belts 112a and 112b.

As described above, each of the wires 110a1 to 110a4 couples the upper-body belt 111 to the left knee belt 112a or the right knee belt 112b. The wires 110a1 to 110a4 may be coupled to the upper-body belt 111 directly or indirectly. Each of the wires 110a1 to 110a4 may be coupled to the left knee belt 112a or the right knee belt 112b directly or indirectly. In the example described above, the one end of each of the wires 110a1 to 110a4 is fixed to, or is directly coupled to, the left knee belt 112a or the right knee belt 112b, and the other end of each of the wires 110a1 to 110a4 is fixed to, or is indirectly coupled to, the upper-body belt 111 via the corresponding one of the motors 114. However, each of the wires 110 may be coupled to the upper-body belt 111 and each of the wires 110 may be coupled to the left knee belt 112a or the right knee belt 112b by using the following configuration, for example.

Specifically, the one end of each of the wires 110 may be indirectly coupled to the left knee belt 112a or the right knee belt 112b via the corresponding one of the motors 114, and the other end of each of the wires 110 may be directly coupled to the upper-body belt 111. Alternatively, both ends of each of the wires 110 may be directly coupled to the upper-body belt 111 and to the left knee belt 112a or the right knee belt 112b, and a motor, a linear actuator, or a pneumatic or hydraulic piston may be disposed in the middle of each of the wires 110 to adjust the length of the wire 110.

Alternatively, the one end of each of the wires 110 may be directly coupled to the left knee belt 112a or the right knee belt 112b, and the other end of each of the wires 110 may be indirectly coupled to the left knee belt 112a or the right knee belt 112b via the corresponding one of the motors 114 in such a manner that each of the wires 110 is arranged to reciprocate between the left knee belt 112a or the right knee belt 112b and the upper-body belt 111. Alternatively, the one end of each of the wires 110 may be directly coupled to the upper-body belt 111, and the other end of each of the wires 110 may be indirectly coupled to the upper-body belt 111 via the corresponding one of the motors 114 in such a manner that each of the wires 110 is arranged to reciprocate between the upper-body belt 111 and the left knee belt 112a or the right knee belt 112b.

Alternatively, both ends of each of the wires 110 may be coupled to the corresponding one of the motors 114 and may be arranged to form a ring through the motor 114. In this case, each of the wires 110 is arranged to reciprocate between the upper-body belt 111 and the left knee belt 112a or the right knee belt 112b, and each of the motors 114 changes the length of the circumference of the ring of the corresponding one of the wires 110.

In any of the configurations described above, each of the wires 110 is coupled to the upper-body belt 111 and the left knee belt 112a or the right knee belt 112b so that the tension thereof is supported by the upper-body belt 111 and the left knee belt 112a or the right knee belt 112b. Thus, when each of the motors 114a1 to 114a4 pulls the corresponding wire among the wires 110, tension that causes the upper-body belt 111 and the left knee belt 112a or the right knee belt 112b to come into close proximity to each other is generated in the corresponding wire.

The force sensors 115 include four force sensors 115a1 to 115a4. The force sensor 115a1 detects the tension of the wire 110a1 and outputs the detected tension to the control unit 120. The force sensor 115a2 detects the tension of the wire 110a2 and outputs the detected tension to the control unit 120. The force sensor 115a3 detects the tension of the wire 110a3 and outputs the detected tension to the control unit 120. The force sensor 115a4 detects the tension of the wire 110a4 and outputs the detected tension to the control unit 120. The force sensor 115a1 is disposed on the wire 110a1 in the left knee belt 112a. The force sensor 115a2 is disposed on the wire 110a2 in the left knee belt 112a. The force sensor 115a3 is disposed on the wire 110a3 in the right knee belt 112b. The force sensor 115a4 is disposed on the wire 110a4 in the right knee belt 112b. The force sensors 115a1 to 115a4 may be located in the upper-body belt 111. Each of the force sensors 115a1 to 115a4 may be capable of detecting the tension of the corresponding wire among the wires 110a1 to 110a4, and may be a strain gauge force sensor or a piezoelectric force sensor, for example. The force sensors 115a1 to 115a4 and the wires 110a1 to 110a4 have a one-to-one correspondence. The force sensors 115a1 to 115a4 are examples of a first sensor.

Each of the wires 110a1 to 110a4 may be a metallic wire or a non-metallic wire. Examples of the non-metallic wire include a fiber wire and a fiber belt. A fiber wire or fiber belt is made of a material such as polyester fiber, nylon fiber, acrylic fiber, para-aramid fiber, ultrahigh molecular weight polyethylene fiber, poly-p-phenylenebenzobisoxazole (PBO) fiber, polyarylate fiber, or carbon fiber. In this embodiment, four coupling belts 111b1 to 111b4 are arranged along the wires 110a1 to 110a4, respectively, and each of the coupling belts 111b1 to 111b4 extends from the upper-body belt 111 to the left knee belt 112a or the right knee belt 112b. The coupling belts 111b1 to 111b4 and the wires 110a1 to 110a4 have a one-to-one correspondence. As a non-limiting example, the coupling belts 111b1 to 111b4 are each integrated with the upper-body belt 111 and the left knee belt 112a or the right knee belt 112b and are made of a material similar to that of the belts 111, 112a, and 112b. For example, the upper-body belt 111, the knee belts 112a and 112b, and the coupling belts 111b1 to 111b4 may form a single suit having an assistance function that is wearable by the user 1. Each of the coupling belts 111b1 to 111b4 contains and covers the corresponding wire among the wires 110a1 to 110a4. The coupling belts 111b1 to 111b4 may be collectively referred to as coupling belts 111b.

Figure 4:
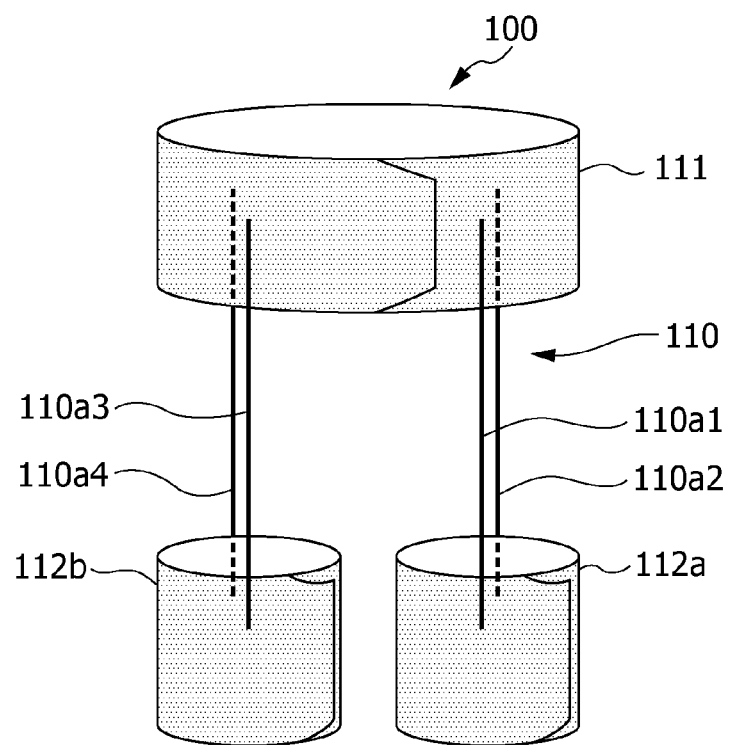
FIG. 4 is a diagram schematically illustrating the arrangement of constituent elements of the assistance apparatus illustrated in FIG. 1.

The arrangement configuration of the wires 110a1 to 110a4 will be described in detail with reference to FIG. 1, FIG. 2, and FIG. 4. FIG. 4 schematically illustrates the arrangement of the constituent elements of the assistance apparatus 100 illustrated in FIG. 1. The wire 110a1 couples the upper-body belt 111 and the left knee belt 112a to each other via the motor 114a1 on or above the front part of the body of the user 1. The wire 110a1 extends upward from the left knee belt 112a on or above the front part of the body of the user 1. The wire 110a2 couples the upper-body belt 111 and the left knee belt 112a to each other via the motor 114a2 on or above the back part of the body of the user 1. The wire 110a2 extends upward from the left knee belt 112a on or above the back part of the body of the user 1. The wire 110a3 couples the upper-body belt 111 and the right knee belt 112b to each other via the motor 114a3 on or above the front part of the body of the user 1. The wire 110a3 extends upward from the right knee belt 112b on or above the front part of the body of the user 1. The wire 110a4 couples the upper-body belt 111 and the right knee belt 112b to each other via the motor 114a4 on or above the back part of the body of the user 1. The wire 110a4 extends upward from the right knee belt 112b on or above the back part of the body of the user 1. In this manner, the wire 110a1 is located on or above the front part of the left leg of the user 1, the wire 110a2 is located on or above the back part of the left leg of the user 1, the wire 110a3 is located on or above the front part of the right leg of the user 1, and the wire 110a4 is located on or above the back part of the right leg of the user 1. The wires 110a1 to 110a4 are pulled individually to apply forces in different directions to the left and right legs.

In the example illustrated in FIG. 1, FIG. 2, and FIG. 4, the wires 110a1 and 110a3 do not cross each other on or above the front part of the body of the user 1. However, the wires 110a1 and 110a3 may cross each other on or above the front part of the body of the user 1. In the example illustrated in FIG. 1, FIG. 2, and FIG. 4, the wires 110a2 and 110a4 do not cross each other on or above the back part of the body of the user 1. However, the wires 110a2 and 110a4 may cross each other on or above the back part of the body of the user 1.

The motors 114a1 to 114a4 pull the wires 110a1 to 110a4 to apply tensions to the wires 110a1 to 110a4, respectively, and the tensions are transmitted to the left and right legs of the user 1 via the upper-body belt 111 and the knee belts 112a and 112b. To effectively transmit the tensions of the wires 110a1 to 110a4 to the left and right legs of the user 1, the upper-body belt 111 and the knee belts 112a and 112b may have rigidity so as not to be deformable and have inflexibility so as not to be extensible. As described above, examples of the material of the upper-body belt 111 and the knee belts 112a and 112b include a non-extensible material.

The upper-body belt 111 and the knee belts 112a and 112b described above are worn by the user 1 in such a manner as to tightly fit the body of the user 1, thus efficiently transmitting the driving forces of the motors 114a1 to 114a4 to the legs of the user 1 through the wires 110a1 to 110a4 and effectively assisting movements of the legs of the user 1. The term "assisting", as used herein, is used to include supporting the movement of the user in order to allow the user to perform a predetermined motion and forcing the body of the user to perform the predetermined motion to induce movements of the body.

Figure 5:
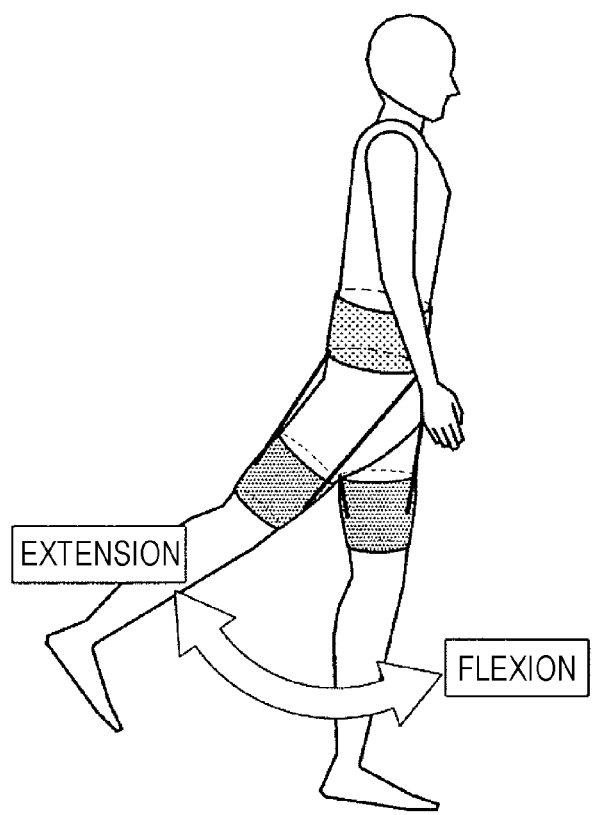
FIG. 5 is a diagram illustrating example motions of the right leg of the user, which are assisted by the assistance apparatus.

A further description will be given of a relationship between tensions applied to the wires 110a1 to 110a4 by the assistance apparatus 100 and motions of the user that are assisted with the tensions. For example, FIG. 5 illustrates example motions of the right leg of the user, which are assisted by the assistance apparatus 100. In the example illustrated in FIG. 5, the assistance apparatus 100 applies an assistance force to the right leg during the swing phase of gait. The assistance apparatus 100 may apply an assistance force to the right leg during the stance phase of gait. The assistance apparatus 100 also enables the left leg of the user to perform motions similar to those of the right leg. As illustrated in FIG. 5, the assistance apparatus 100 can apply an assistance force for flexion and extension to the hip joint of the right leg of the user. The flexion of the hip joint is a motion of moving the thigh forward, and the extension of the hip joint is a motion of moving the thigh backward.

Figure 6A:
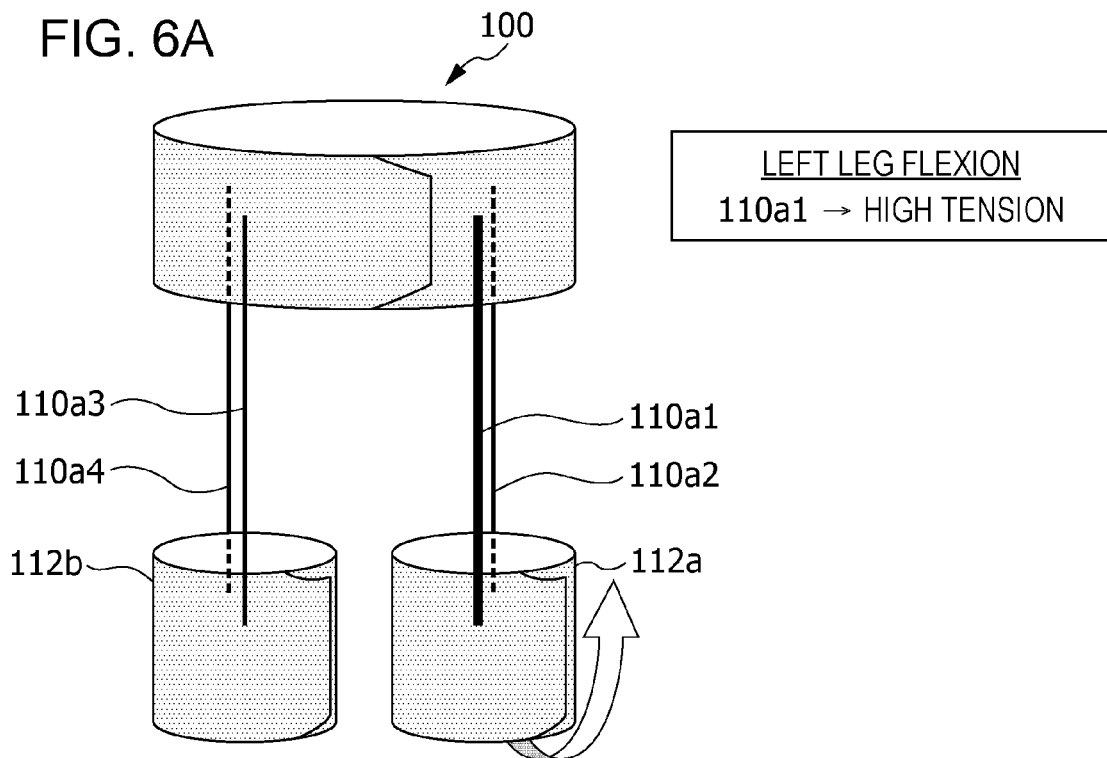
FIG. 6A is a diagram illustrating a case where the assistance apparatus according to the embodiment assists flexion of the hip joint of the left leg of the user.
Figure 6B:
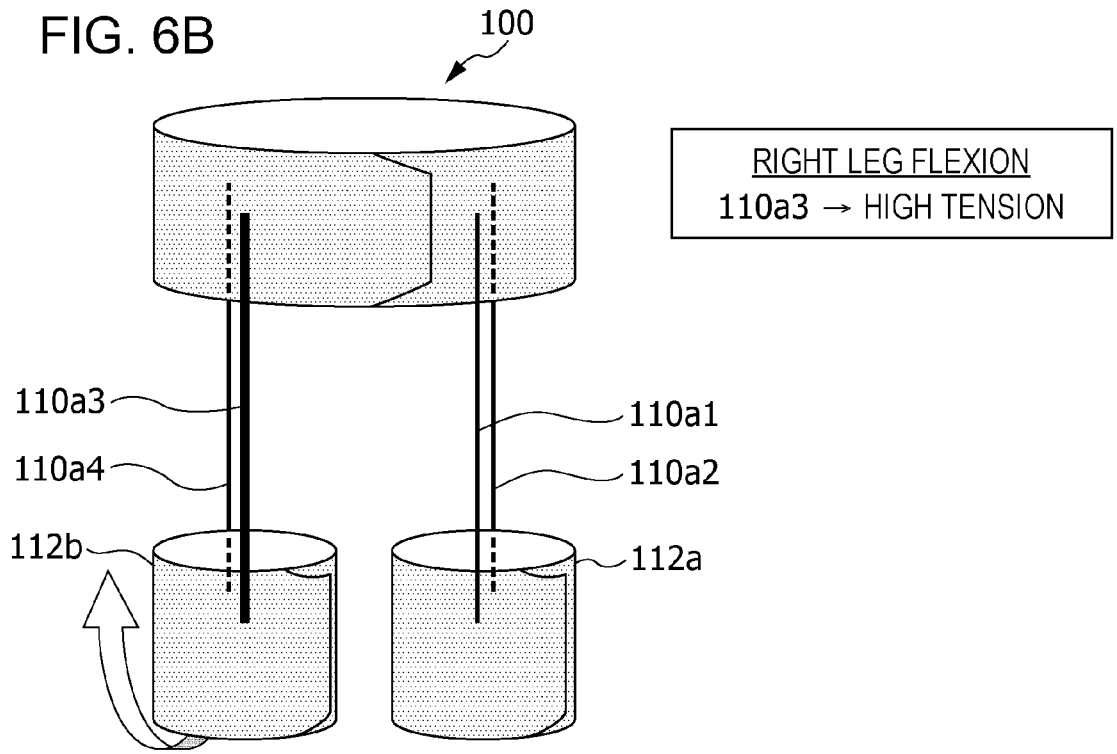
FIG. 6B is a diagram illustrating a case where the assistance apparatus according to the embodiment assists flexion of the hip joint of the right leg of the user.

Further, a relationship between motions of the user, which are induced, or assisted, by the assistance apparatus 100, and assistance forces given to the user through the wires 110a1 to 110a4 will be described with reference to FIG. 6A to FIG. 7B. FIG. 6A illustrates a case where the assistance apparatus 100 according to the embodiment assists flexion of the hip joint of the left leg of the user, and FIG. 6B illustrates a case where the assistance apparatus 100 according to the embodiment assists flexion of the hip joint of the right leg of the user. In FIG. 6A, to flex the left leg, the control unit 120 drives the motor 114a1 to increase the tension of the wire 110a1, that is, to generate a tension in the wire 110a1. In FIG. 6B, to flex the right leg, the control unit 120 drives the motor 114a3 to increase the tension of the wire 110a3. The control unit 120 may control the tensions of the wires 110 in accordance with the detection results of the force sensors 115a1 to 115a4 or in accordance with the amount of driving of the motors 114a1 to 114a4. The details of the control unit 120 will be described below.

In this embodiment, as a non-limiting example, a tension is applied to each of the wires 110a1 to 110a4 in a normal state before flexion. The tension may be applied so as to prevent the corresponding one of the wires 110a1 to 110a4 from loosening and may be less than or equal to 10 N or less than or equal to 5 N, for example. To flex the left leg and the right leg, the tensions of the wires 110a1 and 110a3 are each increased to, for example, a value greater than or equal to 40 N and less than or equal to 100 N. An example for the left leg will be described. A tension greater than or equal to 40 N is exerted on the wire 110a1 for a user, who is a healthy adult male in 20 s to 40 s. At this time, the user is able to clearly recognize that a force in a flexing direction acts on the left leg and promotes flexion of the left leg. When a tension over 80 N is exerted on the wire 110a1, the left leg of the user is raised in the flexing direction. When the tension exerted on the wire 110a1 is less than or equal to 20 N, the user continues the current motion without substantially perceiving the resistance caused by the tension of the wire 110a1. The tension values described above are examples. The tension values may be changed, as desired, in accordance with the age, gender, body size, or physical activity level of the user, the type of motion of the leg, the degree of assistance on the leg, and so on.

FIG. 7A and FIG. 7B illustrate cases where the assistance apparatus 100 according to the embodiment assists extension of the hip joints of the left and right legs of the user, respectively. In FIG. 7A, the control unit 120 increases the tension of the wire 110a2 to extend the left leg. In FIG. 7B, the control unit 120 increases the tension of the wire 110a4 to extend the right leg. The tensions of the wires 110 during extension may be similar to those during flexion.

In the foregoing description, the control unit 120 increases the tension of one wire to assist one motion of one leg. At this time, the control unit 120 may control the motors corresponding to the other three wires in accordance with the motion of the user so that the tensions of the other three wires are kept in the current states, and adjust the tensions of the other three wires. The control unit 120 may control the motors corresponding to the other three wires so as not to exert tension on the three wires. For example, the control unit 120 may stop the operation of the motors corresponding to the other three wires.

The assistance apparatus 100 described above is capable of assisting the user in walking by applying assistance torques, which are assistance forces in flexing and extending directions, to the user in accordance with torques generated during the stance phase and swing phase of the leg of the user while the user is walking.

Further, the configuration of the control unit 120 of the assistance apparatus 100 will be described with reference to FIG. 3. The control unit 120 controls the overall operation of the assistance apparatus 100. The control unit 120 determines operations to be individually applied to the wires 110a1 to 110a4 and controls assistance for the hip joints of the user 1. The operations to be individually applied to the wires 110a1 to 110a4 are operation patterns of the wires 110a1 to 110a4, including the timings of applying tensions to the wires 110a1 to 110a4, the magnitudes of the tensions, and periods during which the tensions are applied.

The control unit 120 acquires an instruction entered by the user 1 or the like from an input device 140 included in the assistance apparatus 100 or from a terminal device 150 external to the assistance apparatus 100, and controls the assistance apparatus 100 to start and stop assistance in accordance with the acquired instruction. The input device 140 of the assistance apparatus 100 may be a button, a switch, a key, a touch pad, a microphone of an audio recognition device, or any other suitable device. The terminal device 150 may be a terminal device carried by the user 1 wearing the assistance apparatus 100, and examples of the terminal device 150 include a smartphone, a smartwatch, a tablet, and a personal computer. The control unit 120 may communicate with the input device 140 and the terminal device 150 in a wired or wireless way. The wireless communication may be implemented using a wireless local area network (LAN) such as wireless fidelity (Wi-Fi (registered trademark)), or may be short-range wireless communication such as Bluetooth (registered trademark) or ZigBee (registered trademark), or any other type of wireless communication. The wired communication may be any existing wired communication. The control unit 120 may include a wired or wireless communication circuit. The wired or wireless communication circuit included in the assistance apparatus 100 may be used to perform wired communication or wireless communication. The input device 140 and the terminal device 150 are examples of an interface device.

Figure 8:
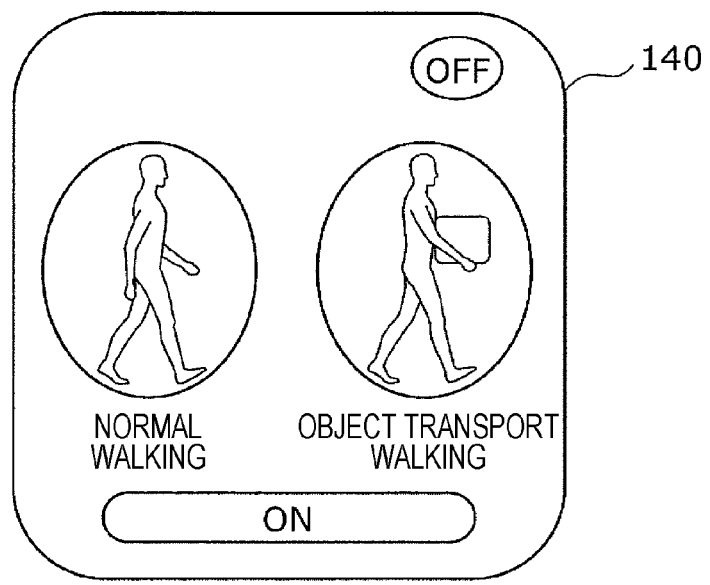
FIG. 8 is a diagram illustrating an example of an input section of an input device included in the assistance apparatus according to the embodiment.

For example, FIG. 8 illustrates an example input section of the input device 140 included in the assistance apparatus 100 according to the embodiment. The input device 140 includes four physical buttons that accept input. The four buttons include an "ON" button for starting the assistance apparatus 100, an "OFF" button for stopping the operation of the assistance apparatus 100, a "normal walking" button for selecting a normal walking mode among operation modes of the assistance apparatus 100, and an "object transport walking" button for selecting an object transport walking mode among the operation modes of the assistance apparatus 100. When the input section of the input device 140 is implemented as a touch panel, the buttons may be icons.

Figure 9:
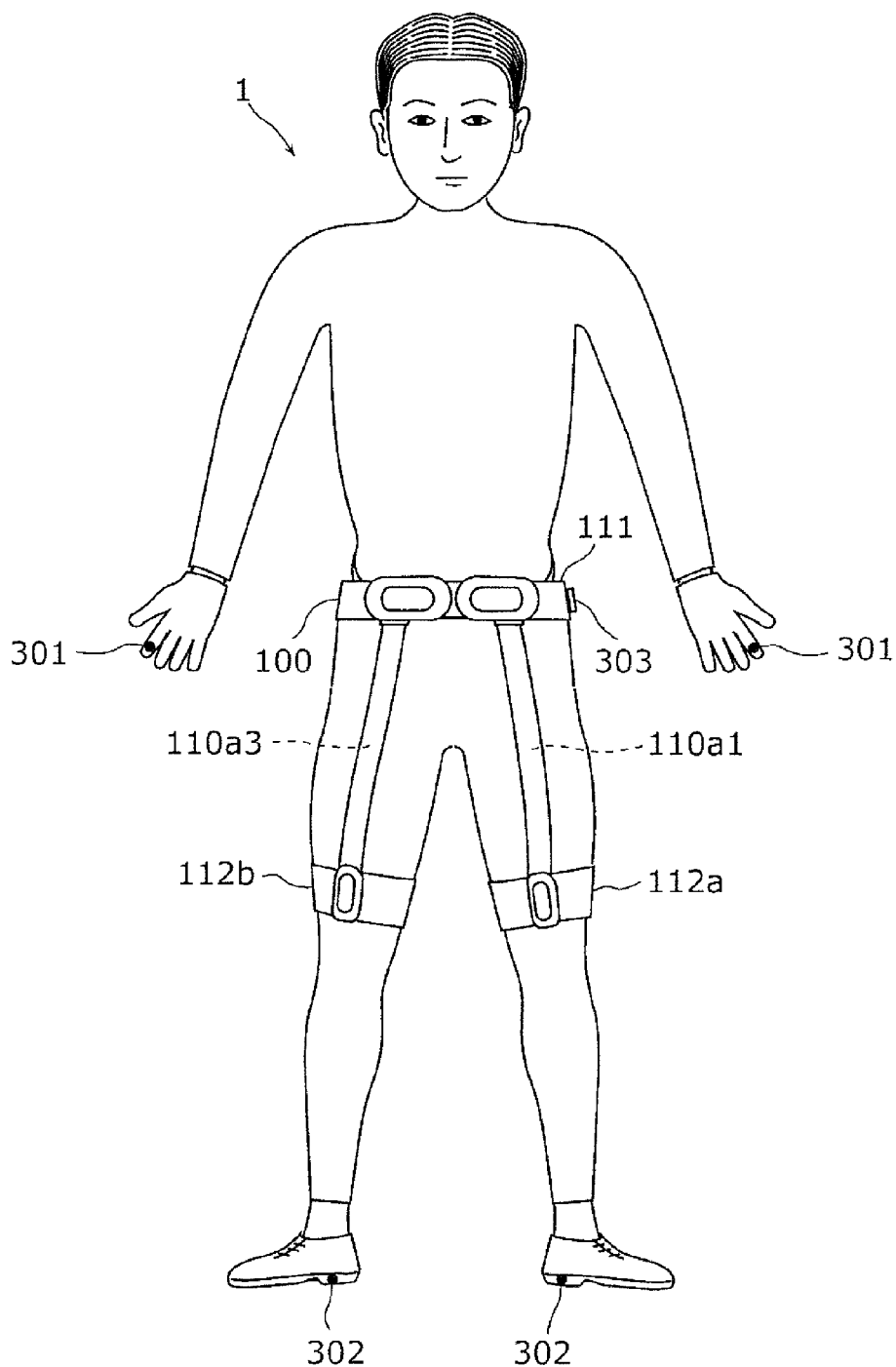
FIG. 9 is a diagram illustrating the arrangement of sensors and so on that are attached to the body of the user.

In this embodiment, furthermore, as illustrated in FIG. 9, a contact sensor 301 and at least one of a pressure-sensitive sensor 302 and an inertial measurement unit 303 are attached to the body of the user 1. FIG. 9 illustrates the arrangement of sensors and so on to be attached to the body of the user 1. The contact sensor 301, the pressure-sensitive sensor 302, and the inertial measurement unit 303 output detection results to the control unit 120. The contact sensor 301 is attached to each of the hands of the user 1. Specifically, the contact sensor 301 is attached to a finger tip or the like of gloves worn by the user 1. The contact sensor 301 may be attached to each of both hands of the user 1 or to either hand of the user 1. The contact sensor 301 detects a direct contact and an indirect contact between the hand of the user 1 and an object. Examples of the contact sensor 301 include a contact detection sensor, a touch sensor, a proximity sensor, and a sensor similar to the pressure-sensitive sensor 302. The contact sensor 301 may be attached to each of the arm, chest, abdomen, and so on of the user 1, which may come into contact with an object when the user 1 holds the object.

The pressure-sensitive sensor 302 is attached to each of the soles of the feet of the user 1. Specifically, the pressure-sensitive sensor 302 is attached to each of the bottoms or the like of shoes worn by the user 1. The pressure-sensitive sensor 302 may be attached to each of both feet of the user 1 or to either foot of the user 1. The pressure-sensitive sensor 302 detects a pressure acting on each of the soles of the feet of the user 1, that is, a load. Examples of the pressure-sensitive sensor 302 include a capacitive pressure sensor, a piezoelectric pressure sensor, and a strain gauge pressure sensor. The inertial measurement unit 303 is attached to a portion of the body of the user 1 that moves along with the movement of the user 1, such as the waist in the upper half of the body of the user 1. Specifically, the inertial measurement unit 303 is attached to the upper-body belt 111. The inertial measurement unit 303 includes an acceleration sensor and a gyro sensor (also referred to as an "angular velocity sensor"). The inertial measurement unit 303 may include an acceleration sensor, but may include no gyro sensor. The inertial measurement unit 303 may further include a geomagnetic sensor. The inertial measurement unit 303 detects, on the basis of a detected acceleration and angular velocity, the acceleration of the user 1 in each direction, and the movement direction, movement speed, and movement distance of the user 1. The pressure-sensitive sensor 302 and the inertial measurement unit 303 are examples of a second sensor.

The contact sensor 301, the pressure-sensitive sensor 302, and the inertial measurement unit 303 exchange information with the control unit 120 via wired communication or wireless communication. The wired communication and wireless communication may be any of the wired communication and wireless communication described above.

As illustrated in FIG. 3, the control unit 120 includes a grasp recognition unit 121, a drive control unit 122, a gait timing detection unit 123, a wire tension recognition unit 124, and a storage unit 125. The grasp recognition unit 121, the drive control unit 122, the gait timing detection unit 123, and the wire tension recognition unit 124, which are constituent elements of the control unit 120, may be implemented by a computer system including a processor such as a central processing unit (CPU) or a digital signal processor (DSP) and a memory such as a random access memory (RAM) and a read-only memory (ROM). Some or all of the functions of the constituent elements described above may be achieved by the CPU or the DSP executing a program recorded on the ROM by using the RAM as a work memory. Alternatively, some or all of the functions of the constituent elements described above may be achieved by a dedicated hardware circuit such as an electronic circuit or an integrated circuit. The functions of some or all of the constituent elements described above may be implemented by a combination of the software functions described above and a hardware circuit. The program may be provided as an application by communication via a communication network such as the Internet, communication conforming to a mobile communication standard, communication via any other wireless or wired network, broadcasting, or the like. A computer system and/or a hardware circuit constituted by the control unit 120 may be mounted on the upper-body belt 111, accommodated in the containers 111a1 to 111a4 together with the motors 114a1 to 114a4, or embedded in the upper-body belt 111 at a different location from the motors 114a1 to 114a4, for example. The control unit 120 is an example of a control circuit.

The storage unit 125 is capable of storing information, and the stored information is retrievable from the storage unit 125. The storage unit 125 stores computer programs in accordance with which the constituent elements of the control unit 120 execute processes, threshold values described below, input profiles of wire tensions described below, and so on. The storage unit 125 is implemented as a storage device, for example, a semiconductor memory such as a ROM, a RAM, or a flash memory, a hard disk drive, or a solid state drive (SSD). In this embodiment, the storage unit 125 is included in the control unit 120. Alternatively, the storage unit 125 may be disposed separately from the control unit 120. The storage unit 125 is an example of a memory.

Figure 10A:
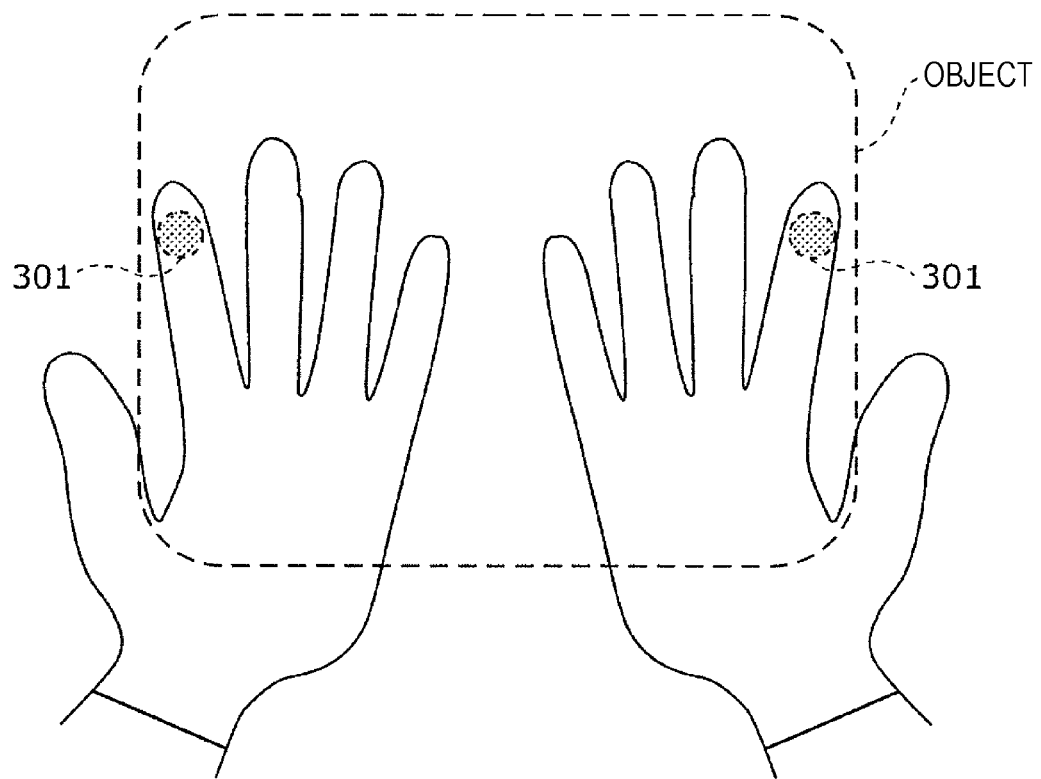
FIG. 10A is a diagram illustrating a relationship between contact sensors and the hands of the user.
Figure 10B:
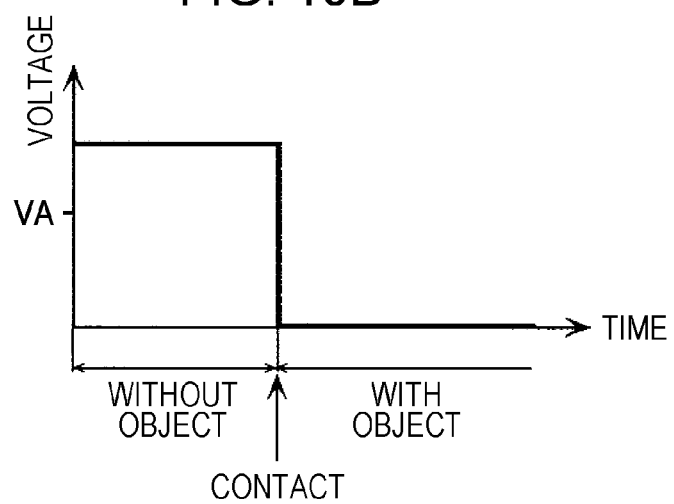
FIG. 10B is a diagram illustrating an example of a signal of a contact sensor.

The grasp recognition unit 121 detects a grasp of an object by the user 1 with their hands. The grasp recognition unit 121 determines whether the user 1 is holding an object with their hands on the basis of a change in sensor value, which is acquired from the contact sensor 301. For example, as illustrated in FIG. 10A and FIG. 10B, the contact sensor 301 is a piezoelectric sensor. In this case, the grasp recognition unit 121 detects a time point at which a voltage value corresponding to a sensor value detected by the contact sensor 301 becomes less than a predetermined value, as a time point at which the hands of the user 1 touch an object, that is, as a time point at which the user 1 grasps the object. For example, in the example illustrated in FIG. 10B, the predetermined value is represented by "VA". FIG. 10A illustrates a relationship between contact sensors 301 and the hands of the user. FIG. 10B illustrates an example of a signal of a contact sensor 301. The grasp recognition unit 121 outputs a detection result to the drive control unit 122.

The gait timing detection unit 123 detects a gait timing to determine a timing of assisting the user 1. The gait timing may include a timing of starting assisting the user 1 during walking, and a timing of determining phases such as a stance phase and a swing phase in a period during which the user 1 takes one step. The drive control unit 122 determines a timing of assisting the user 1 from the gait timing detected by the gait timing detection unit 123 and controls the operation of the motors 114.

Specifically, the gait timing detection unit 123 estimates a gait cycle of the user 1 wearing the assistance apparatus 100, predicts gait phases in the next one step on the basis of the estimation result, and outputs assistance timings based on the predicted gait phases to the drive control unit 122. A gait cycle is a time interval from heel strike of one leg to the next heel strike of the same leg. The gait cycle is constituted by a period of a stance phase and a period of a swing phase. The gait cycle may be sequence of motions occurring from heel strike of one leg to the next heel strike of the same leg.

The gait timing detection unit 123 detects a timing of heel strike of the user 1 on the basis of a sensor value acquired from the pressure-sensitive sensor 302 or on the basis of sensor values acquired from the acceleration sensor and the gyro sensor of the inertial measurement unit 303, and estimates a gait phase for each step, or a gait cycle, of the user 1 in real time. The gait cycles and the steps may be in a one-to-one relationship. Each step of the user 1 is a step with either of the left and right legs. For example, each step of the user 1 corresponds to a period from when the left leg touches the ground to when the left leg touches the ground again. The gait timing detection unit 123 predicts, based on the estimated gait cycle, a gait phase for the next step and a starting time and duration of each of the stance phase and swing phase for the next step, and outputs the prediction results to the drive control unit 122. When the terminal device 150 carried by the user 1 includes an inertial measurement unit, the gait timing detection unit 123 may acquire a sensor value of an acceleration sensor and a sensor value of a gyro sensor from the terminal device 150.

Gait phases represent temporal timings of gait states during a single step taken by the user 1. A time point at which one leg of the user 1 touches the ground corresponds to a time point at which a gait phase is 0%, and a time point at which the same leg of the user 1 touches the ground again corresponds to a time point at which a gait phase is 100%. In a gait phase, timings of gait states of the user 1 are represented in the range of 0% to 100%. For example, a value of 0% to 100% of a gait phase may correspond to the time elapsed from when one leg of the user 1 touches the ground to when the same leg of the user 1 touches the ground again. Specifically, when the time period from when one leg of the user 1 touches the ground to when the same leg of the user 1 touches the ground again is 1 second, the gait phase at the point in time at which a period of 0.5 seconds elapses from the time when the leg of the user 1 touches the ground is represented by 50%.

More specifically, the gait timing detection unit 123 determines a time point at which the leg of the user 1 touches the ground on the basis of the sensor value of the pressure-sensitive sensor 302 in such a manner that, for example, as illustrated in FIG. 11, a time point at which the voltage value corresponding to the pressure sensor value of the pressure-sensitive sensor 302 becomes less than a predetermined value is detected as a timing of heel strike. FIG. 11 illustrates an example of a signal based on signals of the pressure-sensitive sensors 302. For example, the predetermined value is represented by "VB" in FIG. 11. A period during which the pressure-sensitive sensor 302 measures a pressure value greater than or equal to a predetermined value corresponds to a period of heel contact. The pressure-sensitive sensor 302 is placed at each of the feet of the user 1. The gait timing detection unit 123 acquires a timing at which the shoe touches the ground using the pressure-sensitive sensor 302, rather than a timing that is based on the inertial measurement unit 303 located in the upper-body belt 111 or the like. Thus, the gait timing detection unit 123 can more reliably estimate a gait cycle.

Figure 12:
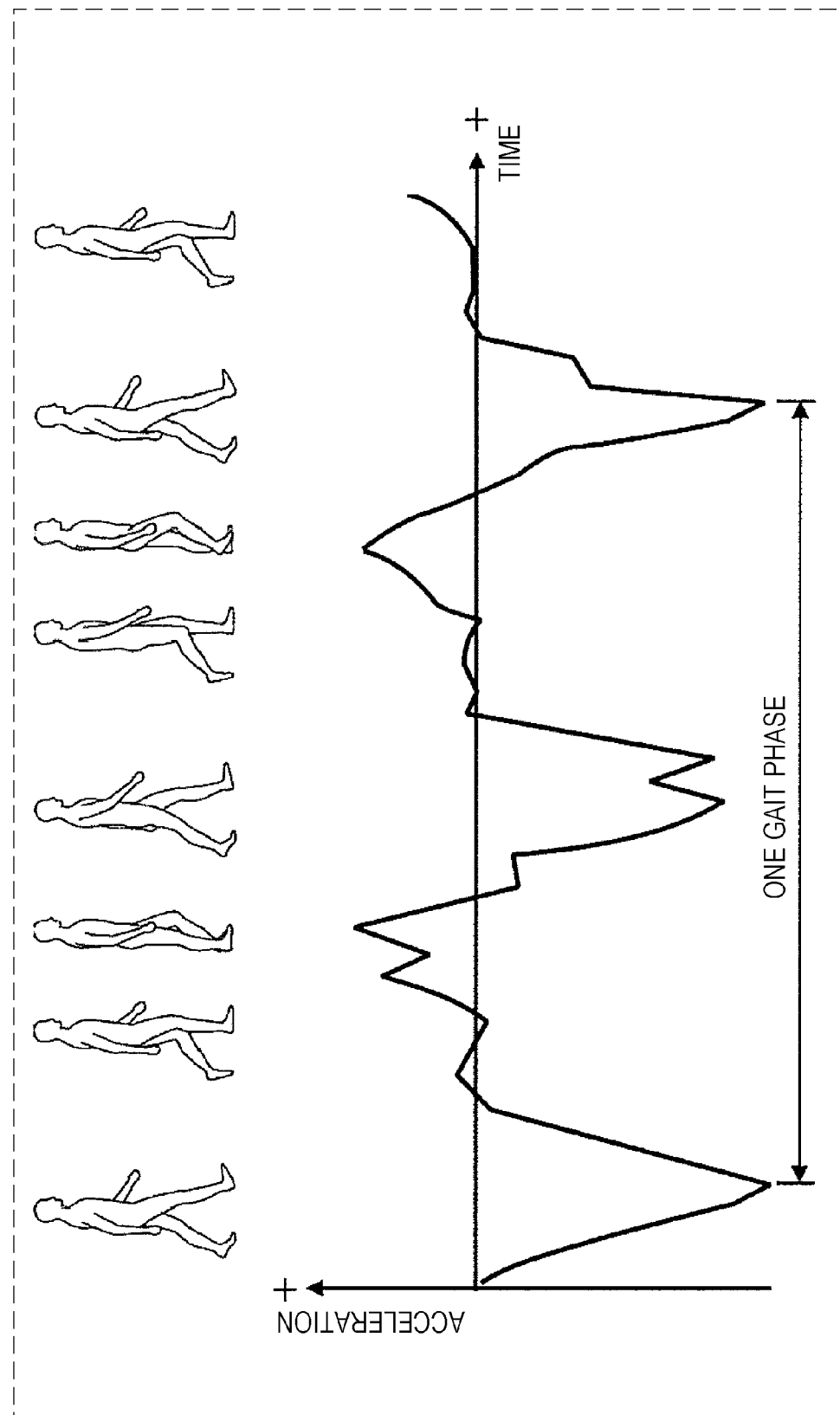
FIG. 12 is a diagram illustrating an example of a signal of an acceleration sensor of an inertial measurement unit.

When the inertial measurement unit 303 is used, the gait timing detection unit 123 determines a time point at which the foot of the user 1 touches the ground on the basis of information obtained by the acceleration sensor. For a method for estimating a time point at which a foot touches the ground by using an acceleration sensor, see, for example, IEEE TRANSACTIONS ON BIOMEDICAL ENGINEERING, VOL. 52, NO. 3, 2005, p. 488, FIG. 1, p. 489, FIG. 2. When estimating a gait cycle on the basis of a sensor value of the inertial measurement unit 303, the gait timing detection unit 123 may estimate a gait cycle by using signal waveforms obtained from the acceleration sensor and the gyro sensor. For example, a gait cycle can be estimated by using a signal waveform obtained from the acceleration sensor, as illustrated in FIG. 12. In the example illustrated in FIG. 12, the signal waveform obtained from the acceleration sensor can be used to estimate a time point at which the foot of the user 1 touches the ground, and a gait cycle can be estimated accordingly. FIG. 12 illustrates an example of a signal of the acceleration sensor of the inertial measurement unit 303.

The user 1 may wear an angle sensor (also referred to as a "tilt sensor"). In this case, the angle sensor is attached to, for example, a thigh of the user 1. The gait timing detection unit 123 acquires the angle of the hip joint of the user 1 as gait information. The gait timing detection unit 123 calculates a gait phase on the basis of a cycle of change in the angle of the hip joint of the user 1.

Regardless of which of the pressure-sensitive sensor 302 and the inertial measurement unit 303 is used, for example, the gait timing detection unit 123 may estimate, based on a sensor value of the pressure-sensitive sensor 302 or a sensor value of the inertial measurement unit 303 for the latest three steps of the user 1, an elapsed time of 0% to 100% of a gait phase for each step and may calculate an average value of the three elapsed times. Then, the gait timing detection unit 123 may predict the point in time corresponding to 100% of the gait phase for the next step on the basis of the average value of the elapsed times. Further, the gait timing detection unit 123 may estimate the start timings of the stance phase and the swing phase during the gait phase for each step on the basis of the signal waveform of the sensor and calculate an average value of the start timings for the three steps. Then, the gait timing detection unit 123 may predict, based on the average value, the start timings of the stance phase and the swing phase for the next one step.

Alternatively, the gait timing detection unit 123 may estimate, based on a sensor value of the pressure-sensitive sensor 302 or a sensor value of the inertial measurement unit 303 for the last one step of the user 1, an elapsed time of 0% to 100% of the gait phase for the one step and may predict the point in time corresponding to 100% of the gait phase for the next step on the basis of the estimated elapsed time. Further, the gait timing detection unit 123 may estimate the start timings of the stance phase and the swing phase during the one step on the basis of the sensor values for the last one step of the user 1, and may predict the start timings of the stance phase and the swing phase for the next one step.

The wire tension recognition unit 124 detects the tensions generated in the wires 110a1 to 110a4. The wire tension recognition unit 124 detects the tensions of the wires 110a1 to 110a4 on the basis of sensor values acquired from the force sensors 115a1 to 115a4. The wire tension recognition unit 124 outputs the detected tensions of the wires 110a1 to 110a4 to the drive control unit 122.

The drive control unit 122 controls the motors 114a1 to 114a4, which respectively adjust the tensions of the wires 110a1 to 110a4, on the basis of information on a predicted gait phase of the user 1, which is acquired from the gait timing detection unit 123, and on the basis of information indicating whether the user 1 is carrying an object, which is acquired from the grasp recognition unit 121. The drive control unit 122 starts the motors 114a1 to 114a4, stops the operation of the motors 114a1 to 114a4, and controls the amount by which the wires 110a1 to 110a4 are respectively pulled by the motors 114a1 to 114a4 and the pulling tensions of the wires 110a1 to 110a4. The drive control unit 122 controls the amount of rotation of each of the motors 114a1 to 114a4 and adjusts the rotation torque of each of the motors 114a1 to 114a4, thereby enabling control of the amount by which the corresponding wire among the wires 110 is pulled and the pulling tensions of the corresponding wire.

Specifically, the drive control unit 122 determines a type of assistance to be provided to the user 1 on the basis of the prediction result of the gait timing acquired from the gait timing detection unit 123. Examples of the type of assistance include motions of the leg on which assistance is to be provided to the user 1, such as flexion and extension. In accordance with the type of assistance, the drive control unit 122 further determines a wire to be pulled to assist a motion of the user 1 among the wires 110a1 to 110a4, a tension to be applied to the wire, and a timing of pulling the wire.

Further, the drive control unit 122 changes the relationship between the tension of a wire and the timing of pulling the wire even for the same type of assistance on the basis of information acquired from the grasp recognition unit 121 indicating whether the user 1 is carrying an object.

An assistance correspondence, which is a relationship between the gait timing acquired from the gait timing detection unit 123 and the type of assistance, is set in advance and is stored in, for example, the storage unit 125. A wire-tension relationship, which is a relationship between a wire to be pulled, a tension of the wire, and a timing of pulling the wire, is set in advance in accordance with the type of assistance and information indicating whether the user 1 is carrying an object, and is stored in, for example, the storage unit 125. The wire-tension relationship may be updated on the basis of the achievement of assistance-based control by the assistance apparatus 100. On the basis of information on the assistance correspondence and the wire-tension relationship, which are stored in the storage unit 125, the drive control unit 122 determines a type of assistance to be provided to the user 1 and determines control of wires corresponding to the determined type of assistance. The drive control unit 122 controls the motors linked to the determined wires, in accordance with tensions to be applied to the wires and timings of pulling the wires.

Further, the drive control unit 122 controls the operation of the motors 114a1 to 114a4 on the basis of information on the tensions of the wires 110a1 to 110a4, which is acquired from the wire tension recognition unit 124, so that the tensions of the wires 110a1 to 110a4 have predetermined levels. In addition, the drive control unit 122 may change the wire-tension relationship on the basis of, in addition to the information acquired from the grasp recognition unit 121, the gait timing detection unit 123, and the wire tension recognition unit 124, information on the user 1, such as age, gender, body size, and physical activity level, the degree of assistance on the leg, and so on, and may use the changed wire-tension relationship.

2. Modification of Assistance Apparatus

Figure 13:
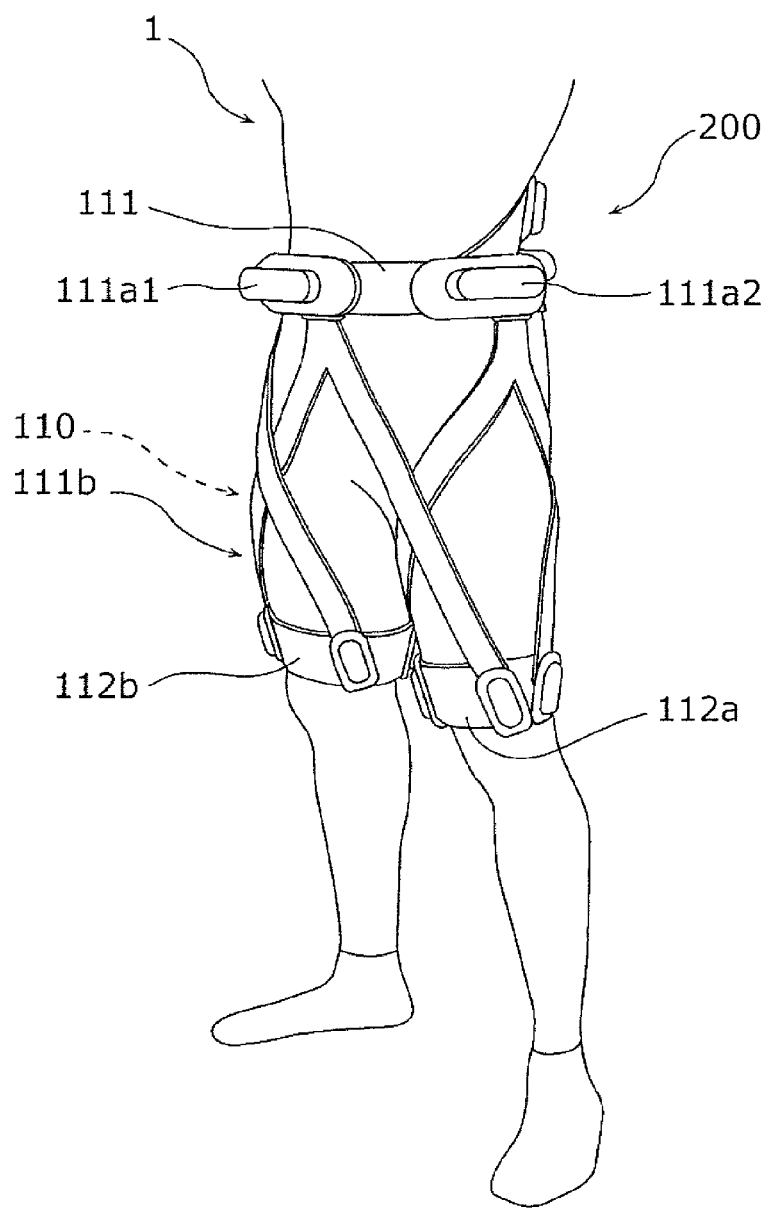
FIG. 13 is a perspective view of a user wearing an assistance apparatus according to a modification of the embodiment, as viewed obliquely from the front.
Figure 14:
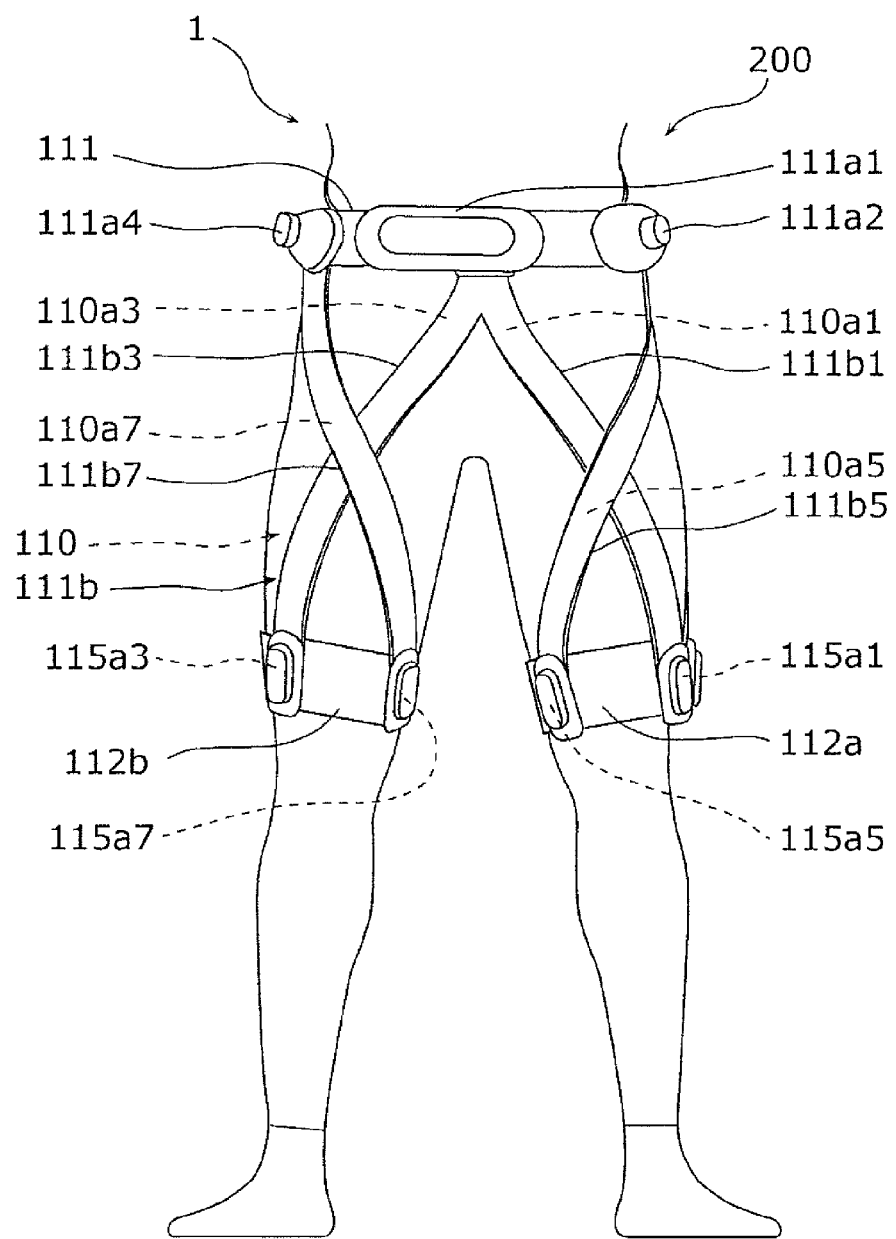
FIG. 14 is a front view of the user wearing the assistance apparatus illustrated in FIG. 13.
Figure 15:
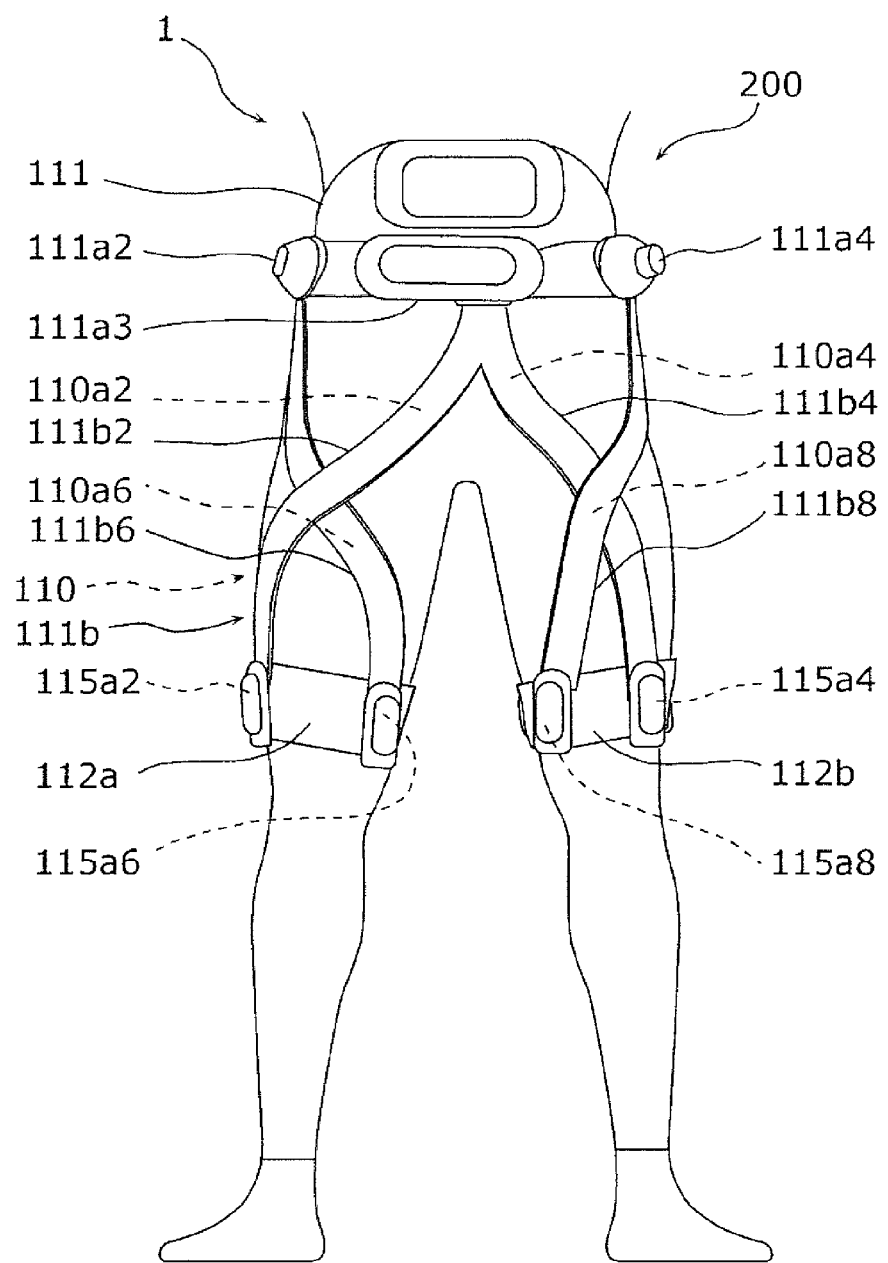
FIG. 15 is a back view of the user wearing the assistance apparatus illustrated in FIG. 13.
Figure 16:
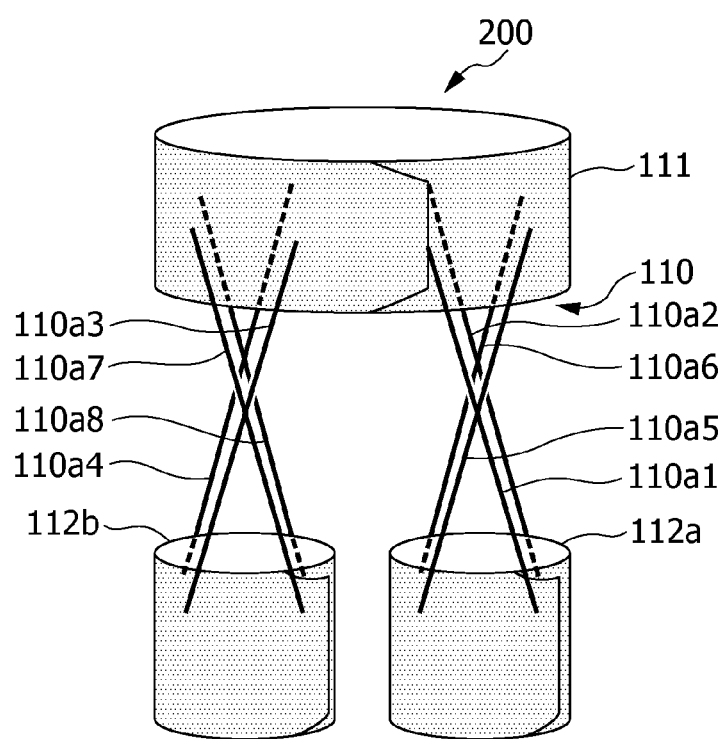
FIG. 16 is a diagram schematically illustrating the arrangement of constituent elements of the assistance apparatus illustrated in FIG. 13.
Figure 17:
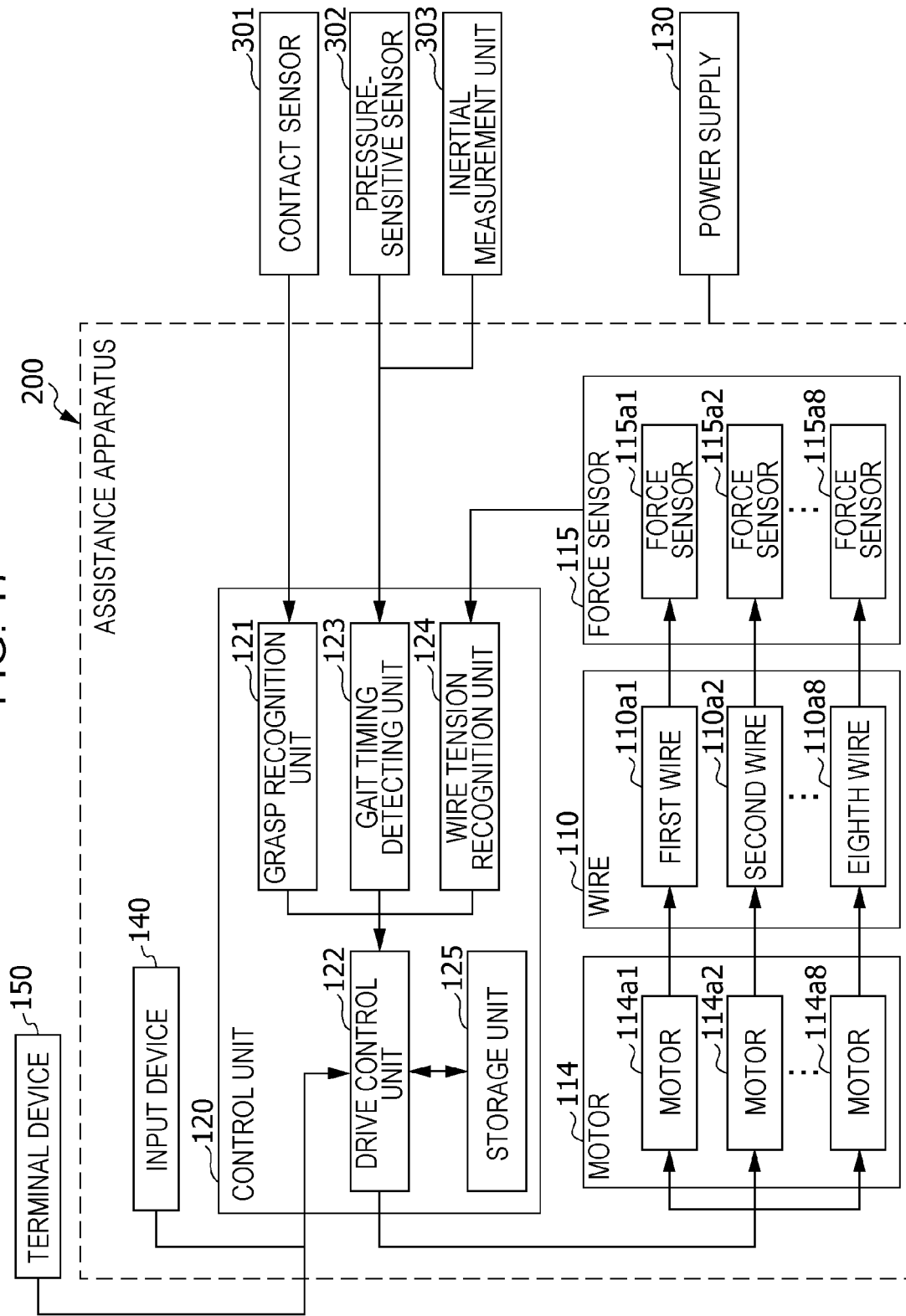
FIG. 17 is a block diagram illustrating a functional configuration of the assistance apparatus illustrated in FIG. 13.

In the assistance apparatus 100 described above, the upper-body belt 111 is coupled to the knee belts 112*a* and 112*b* by using the four wires 110*a*1 to 110*a*4. However, the number of wires is not limited to that in the embodiment. For example, as illustrated in FIG. 13 to FIG. 17, eight wires may be used. FIG. 13 is a perspective view of a user 1 wearing an assistance apparatus 200 according to a modification of the embodiment, as viewed obliquely from the front. FIG. 14 is a front view of the user 1 wearing the assistance apparatus 200 illustrated in FIG. 13. FIG. 15 is a back view of the user 1 wearing the assistance apparatus 200 illustrated in FIG. 13. FIG. 16 is a diagram schematically illustrating the arrangement of constituent elements of the assistance apparatus 200 illustrated in FIG. 13. FIG. 17 is a block diagram illustrating a functional configuration of the assistance apparatus 200 illustrated in FIG. 13.

As illustrated in FIG. 13 to FIG. 17, the assistance apparatus 200 according to the modification includes an upper-body belt 111, knee belts 112*a* and 112*b*, and eight wires, namely, first to eighth wires 110*a*1 to 110*a*8. The assistance apparatus 200 further includes a motor 114*a*1 linked to the first wire 110*a*1, a motor 114*a*2 linked to the second wire 110*a*2, a motor 114*a*3 linked to the third wire 110*a*3, a motor 114*a*4 linked to the fourth wire 110*a*4, a motor 114*a*5 linked to the fifth wire 110*a*5, a motor 114*a*6 linked to the sixth wire 110*a*6, a motor 114*a*7 linked to the seventh wire 110*a*7, a motor 114*a*8 linked to the eighth wire 110*a*8, a force sensor 115*a*1 disposed on the first wire 110*a*1, a force sensor 115*a*2 disposed on the second wire 110*a*2, a force sensor 115*a*3 disposed on the third wire 110*a*3, a force sensor 115*a*4 disposed on the fourth wire 110*a*4, a force sensor 115*a*5 disposed on the fifth wire 110*a*5, a force sensor 115*a*6 disposed on the sixth wire 110*a*6, a force sensor 115*a*7 disposed on the seventh wire 110*a*7, a force sensor 115*a*8 disposed on the eighth wire 110*a*8, and a control unit 120.

The upper-body belt 111 includes containers 111*a*1, 111*a*2, 111*a*3, and 111*a*4 so as to correspond to the front part, left side part, back part, and right side part of the body of the user 1, respectively. The motors 114*a*1 and 114*a*3 are accommodated in the container 111*a*1, the motors 114*a*5 and 114*a*6 are accommodated in the container 111*a*2, the motors 114*a*2 and 114*a*4 are accommodated in the container 111*a*3, and the motors 114*a*7 and 114*a*8 are accommodated in the container 111*a*4.

The first wire 110*a*1 and the fifth wire 110*a*5 are arranged to extend in directions crossing each other on or above the front part of the body of the user 1, and, more specifically, are arranged to cross each other. Each of the first wire 110*a*1 and the fifth wire 110*a*5 has one end fixed to the left knee belt 112*a*. The first wire 110*a*1 has another end coupled to the motor 114*a*1, and the fifth wire 110*a*5 has another end coupled to the motor 114*a*5. That is, the first wire 110*a*1 couples the left knee belt 112*a* and the motor 114*a*1 to each other, and the fifth wire 110*a*5 couples the left knee belt 112*a* and the motor 114*a*5 to each other.

The second wire 110*a*2 and the sixth wire 110*a*6 are arranged to extend in directions crossing each other on or above the back part of the body of the user 1, and, more specifically, are arranged to cross each other. Each of the second wire 110*a*2 and the sixth wire 110*a*6 has one end fixed to the left knee belt 112*a*. The second wire 110*a*2 has another end coupled to the motor 114*a*2, and the sixth wire 110*a*6 has another end coupled to the motor 114*a*6. That is, the second wire 110*a*2 couples the left knee belt 112*a* and the motor 114*a*2 to each other, and the sixth wire 110*a*6 couples the left knee belt 112*a* and the motor 114*a*6 to each other.

The third wire 110*a*3 and the seventh wire 110*a*7 are arranged to extend in directions crossing each other on or above the front part of the body of the user 1, and, more specifically, are arranged to cross each other. Each of the third wire 110*a*3 and the seventh wire 110*a*7 has one end fixed to the right knee belt 112*b*. The third wire 110*a*3 has another end coupled to the motor 114*a*3, and the seventh wire 110*a*7 has another end coupled to the motor 114*a*7. That is, the third wire 110*a*3 couples the right knee belt 112*b* and the motor 114*a*3 to each other, and the seventh wire 110*a*7 couples the right knee belt 112*b* and the motor 114*a*7 to each other.

The fourth wire 110*a*4 and the eighth wire 110*a*8 are arranged to extend in directions crossing each other on or above the back part of the body of the user 1, and, more specifically, are arranged to cross each other. Each of the fourth wire 110*a*4 and the eighth wire 110*a*8 has one end fixed to the right knee belt 112*b*. The fourth wire 110*a*4 has another end coupled to the motor 114*a*4, and the eighth wire 110*a*8 has another end coupled to the motor 114*a*8. That is, the fourth wire 110*a*4 couples the right knee belt 112*b* and the motor 114*a*4 to each other, and the eighth wire 110*a*8 couples the right knee belt 112*b* and the motor 114*a*8 to each other.

Further, the first wire 110*a*1 and the second wire 110*a*2 extend upward and toward the right side of the body of the user 1 from the left knee belt 112*a*. Specifically, the first wire 110*a*1 and the second wire 110*a*2 extend to the right side of the body of the user 1 while extending upward from the left knee belt 112*a*, and, for example, extend upward and diagonally to the right from the left knee belt 112*a*. The fifth wire 110*a*5 and the sixth wire 110*a*6 extend upward and toward the left side of the body of the user 1 from the left knee belt 112*a*. Specifically, the fifth wire 110*a*5 and the sixth wire 110*a*6 extend to the left side of the body of the user 1 while extending upward from the left knee belt 112*a*, and, for example, extend upward and diagonally to the left from the left knee belt 112*a*. The third wire 110*a*3 and the fourth wire 110*a*4 extend upward and toward the left side of the body of the user 1 from the right knee belt 112*b*. Specifically, the third wire 110*a*3 and the fourth wire 110*a*4 extend to the left side of the body of the user 1 while extending upward from the right knee belt 112*b*, and, for example, extend upward and diagonally to the left from the right knee belt 112*b*. The seventh wire 110*a*7 and the eighth wire 110*a*8 extend upward and toward the right side of the body of the user 1 from the right knee belt 112*b*. Specifically, the seventh wire 110*a*7 and the eighth wire 110*a*8 extend to the right side of the body of the user 1 while extending upward from the right knee belt 112*b*, and, for example, extend upward and diagonally to the right from the right knee belt 112*b*.

Figure 18:
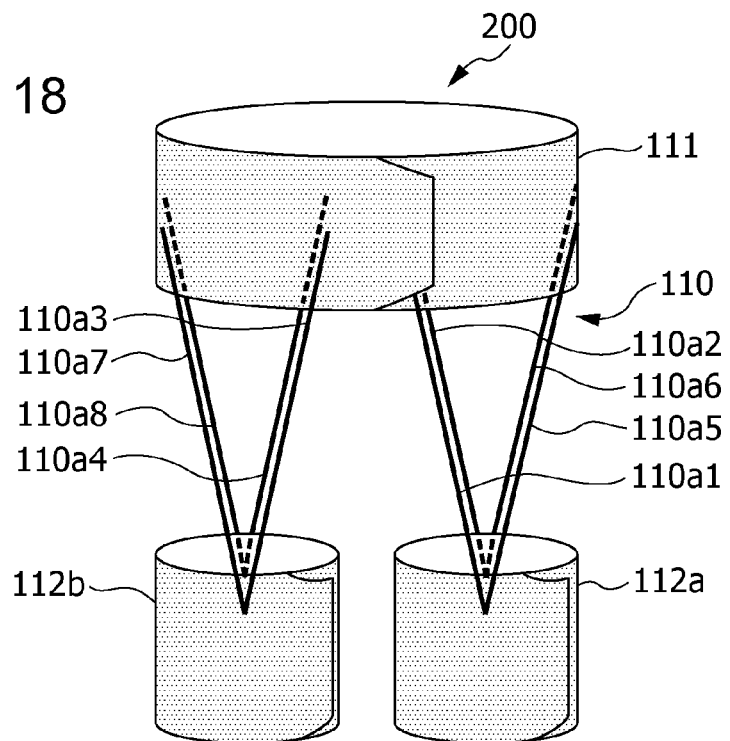
FIG. 18 is a diagram illustrating a modification of the arrangement of wires in the assistance apparatus illustrated in FIG. 13.
Figure 19:
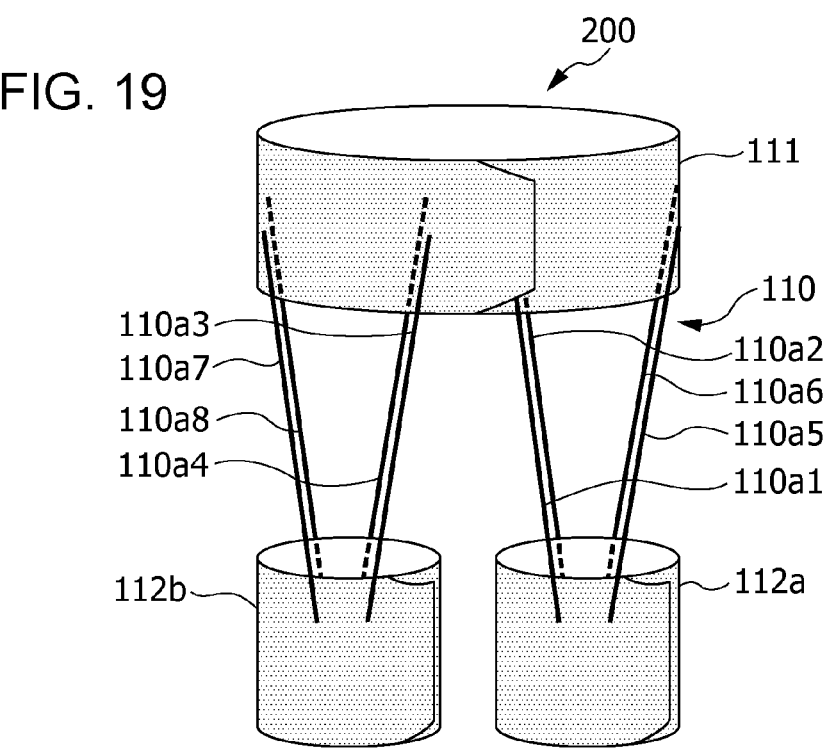
FIG. 19 is a diagram illustrating a modification of the arrangement of wires in the assistance apparatus illustrated in FIG. 13.

Extending of two wires in directions crossing each other is equivalent to crossing of directions in which the two wires extend. Further, crossing of directions in which the two wires extend is equivalent to extending of the two wires in directions that are not parallel to each other. The directions may cross each other at an intersection, or may have no intersection therebetween and may not cross each other. Thus, the two wires may actually cross each other at an intersection or may not actually cross each other. Such two wires extending in directions crossing each other may or may not cross each other when the user 1 is viewed from outside the user 1. When the two wires do not cross each other, as illustrated in FIG. 18 and FIG. 19, the two wires may extend to form a V shape, for example, or may extend away from each other. FIG. 18 and FIG. 19 illustrate modifications of the arrangement of the wires 110 in the assistance apparatus 200 illustrated in FIG. 13.

In this modification, furthermore, eight coupling belts 111b1 to 111b8 are arranged along the first wire 110a1 to the eighth wire 110a8, respectively, and each of the eight coupling belts 111b1 to 111b8 extends from the upper-body belt 111 to the left knee belt 112a or the right knee belt 112b. The coupling belts 111b1 to 111b8 and the first wire 110a1 to the eighth wire 110a8 have a one-to-one correspondence.

In this modification, as a non-limiting example of pairs of two wires extending in directions crossing each other, two wires in each pair of wires cross each other to form an X shape. The first wire 110a1 to the eighth wire 110a8 may have any other arrangement configuration. As illustrated in FIG. 18, for example, the first wire 110a1 and the fifth wire 110a5 may be arranged to form a V shape. In this case, the first wire 110a1 and the fifth wire 110a5 may form a tapered shape that becomes wider toward the top from the left knee belt 112a. In addition, on the left knee belt 112a, the first wire 110a1 and the fifth wire 110a5 may be arranged in close proximity to each other in the manner illustrated in FIG. 18 or may be arranged away from each other in the manner illustrated in FIG. 19. The same applies to the other pairs of wires.

Figure 20:
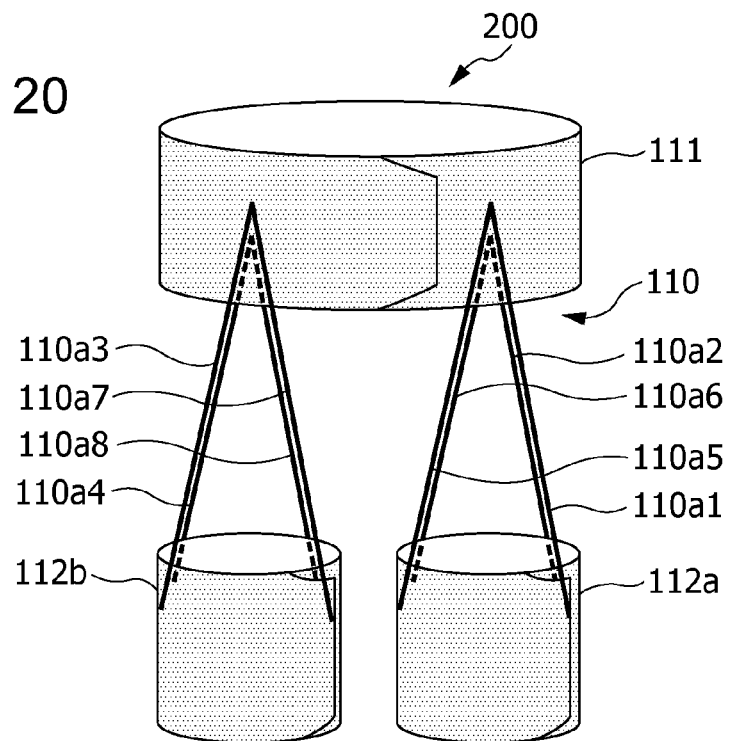
FIG. 20 is a diagram illustrating a modification of the arrangement of wires in the assistance apparatus illustrated in FIG. 13.
Figure 21:
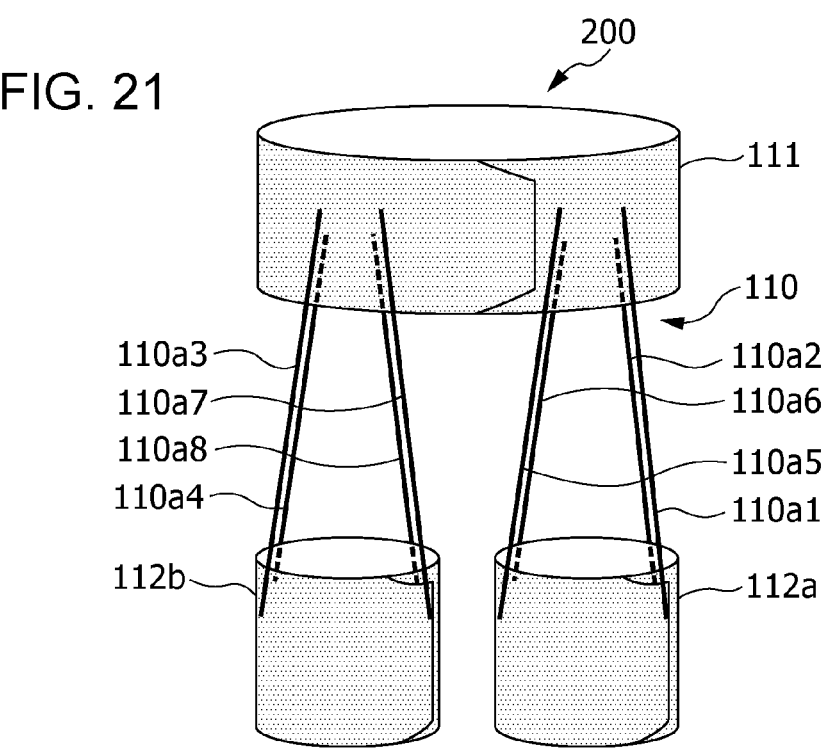
FIG. 21 is a diagram illustrating a modification of the arrangement of wires in the assistance apparatus illustrated in FIG. 13.

Alternatively, as illustrated in FIG. 20, for example, the first wire 110a1 and the fifth wire 110a5 may be arranged to form an inverted V shape. In this case, the first wire 110a1 and the fifth wire 110a5 may form a tapered shape that becomes narrower toward the top from the left knee belt 112a. In addition, on the upper-body belt 111, the first wire 110a1 and the fifth wire 110a5 may be arranged in close proximity to each other in the manner illustrated in FIG. 20 may be arranged away from each other in the manner illustrated in FIG. 21. The same applies to the other pairs of wires. FIG. 20 and FIG. 21 illustrate modifications of the arrangement of the wires 110 in the assistance apparatus 200 illustrated in FIG. 13.

In FIG. 13 to FIG. 15, the first wire 110a1 and the third wire 110a3 extending from the container 111a1 form an inverted V shape, the fifth wire 110a5 and the sixth wire 110a6 extending from the container 111a2 form an inverted V shape, the second wire 110a2 and the fourth wire 110a4 extending from the container 111a3 form an inverted V shape, and the seventh wire 110a7 and the eighth wire 110a8 extending from the container 111a4 form an inverted V shape. However, the arrangement of the first wire 110a1 to the eighth wire 110a8 on the upper-body belt 111 is not limited to the arrangement described above. For example, a wound portion of the first wire 110a1 and a wound portion of the third wire 110a3 may be arranged away from each other so that the two wires 110a1 and 110a3 do not cross each other or may be arranged so that the two wires 110a1 and 110a3 cross each other to form an X shape. A wound portion of the fifth wire 110a5 and a wound portion of the sixth wire 110a6 may be arranged away from each other so that the two wires 110a5 and 110a6 do not cross each other or may be arranged so that the two wires 110a5 and 110a6 cross each other to form an X shape. A wound portion of the second wire 110a2 and a wound portion of the fourth wire 110a4 may be arranged away from each other so that the two wires 110a2 and 110a4 do not cross each other or may be arranged so that the two wires 110a2 and 110a4 cross each other to form an X shape. A wound portion of the seventh wire 110a7 and a wound portion of the eighth wire 110a8 may be arranged away from each other so that the two wires 110a7 and 110a8 do not cross each other or may be arranged so that the two wires 110a7 and 110a8 cross each other to form an X shape.

In the assistance apparatus 200 described above, for example, the motor 114a1 generates a tension in the first wire 110a1, and the motor 114a5 generates a tension in the fifth wire 110a5. The assistance apparatus 200 drives the motor 114a1 to increase the tension of the first wire 110a1. Thus, a force is exerted on the leg of the user 1 in a direction in which the distance between the knee and the heel is reduced to assist a motion of the ankle of the user 1 during walking. The assistance apparatus 200 drives the motor 114a5 to increase the tension of the fifth wire 110a5. Thus, a force is exerted on the leg of the user 1 in a direction in which the distance between the knee and the heel is reduced to assist a motion of the ankle of the user 1 during walking. Further, by setting the tensions of the first wire 110a1 and the fifth wire 110a5 to different values, the assistance apparatus 200 can generate a moment of force regarding a left or right tilt of the heel of the user 1 and can assist a motion of the ankle of the user 1 during walking.

The assistance apparatus 200 can apply an assistance force to the hip joint of the left leg and the hip joint of the right leg of the user 1 to flex and extend the hip joints. Referring to FIG. 22A, a case is illustrated in which the assistance apparatus 200 according to the modification assists flexion of the hip joint of the left leg of the user 1. Referring to FIG. 22B, a case is illustrated in which the assistance apparatus 200 according to the modification assists flexion of the hip joint of the right leg of the user 1. In FIG. 22A, to flex the left leg, the drive control unit 122 drives the motors 114a1 and 114a5 to increase the tensions of the first wire 110a1 and the fifth wire 110a5. In FIG. 22B, to flex the right leg, the drive control unit 122 drives the motors 114a3 and 114a7 to increase the tensions of the third wire 110a3 and the seventh wire 110a7. In this modification, the tensions of the first wire 110a1 and the fifth wire 110a5 are assumed to be equivalent, but may be different. In this modification, the tensions of the third wire 110a3 and the seventh wire 110a7 are assumed to be equivalent, but may be different.

Figure 23A:
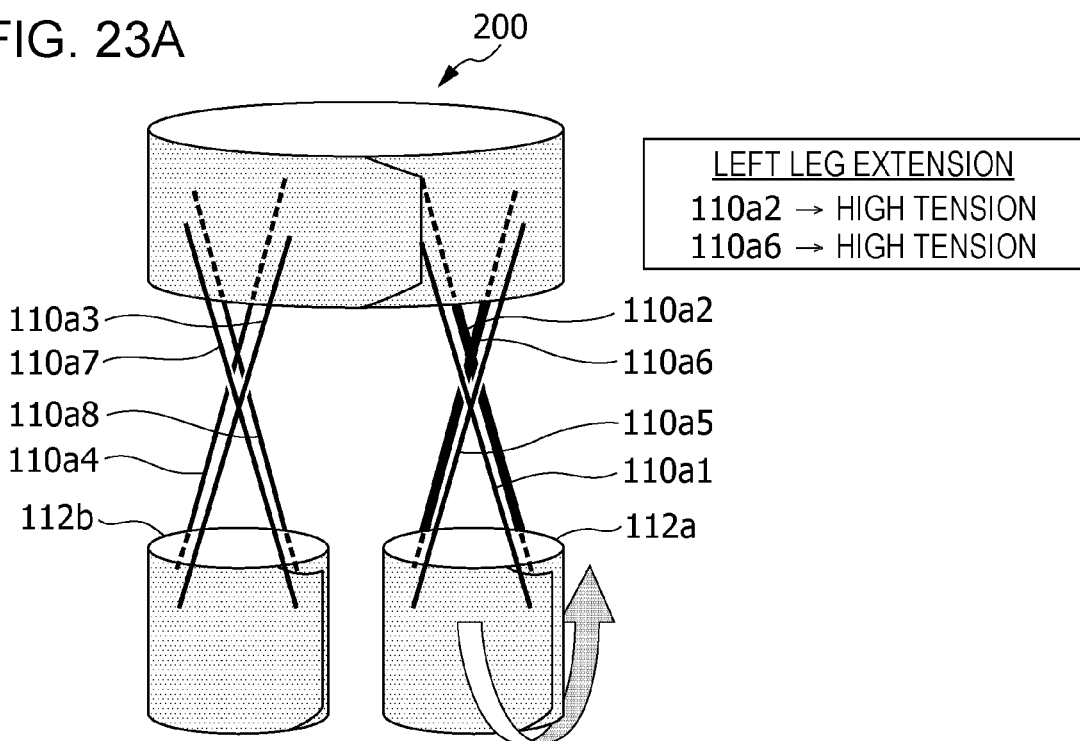
FIG. 23A is a diagram illustrating a case where the assistance apparatus according to the modification assists extension of the hip joint of the left leg of the user.
Figure 23B:
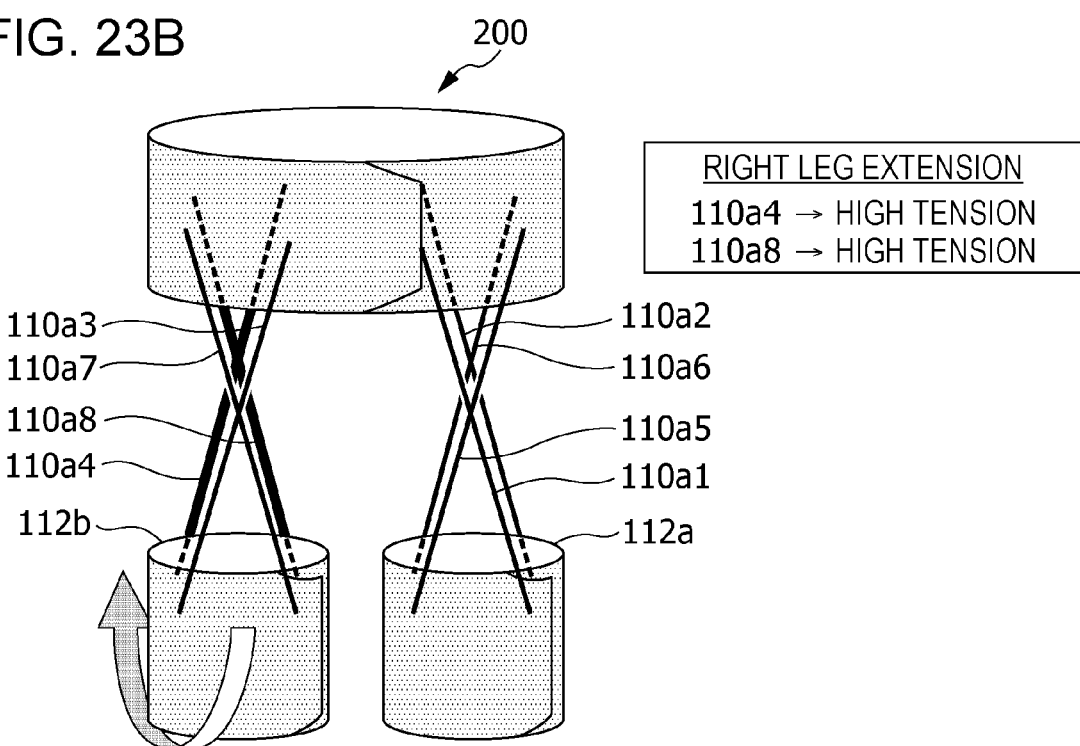
FIG. 23B is a diagram illustrating a case where the assistance apparatus according to the modification assists extension of the hip joint of the right leg of the user.

Referring to FIG. 23A, a case is illustrated in which the assistance apparatus 200 according to the modification assists extension of the hip joint of the left leg of the user 1. Referring to FIG. 23B, a case is illustrated in which the assistance apparatus 200 according to the modification assists extension of the hip joint of the right leg of the user 1. In FIG. 23A, to extend the left leg, the drive control unit 122 increases the tensions of the second wire 110a2 and the sixth wire 110a6. In FIG. 23B, to extend the right leg, the drive control unit 122 increases the tensions of the fourth wire 110a4 and the eighth wire 110a8. The tension of the second wire 110a2 for extension may be similar to the tension of the first wire 110a1 for flexion. The tension of the sixth wire 110a6 for extension may be similar to the tension of the fifth wire 110a5 for flexion. The tension of the fourth wire 110a4 for extension may be similar to the tension of the third wire 110a3 for flexion. The tension of the eighth wire 110a8 for extension may be similar to the tension of the seventh wire 110a7 for flexion.

In the foregoing description, the drive control unit 122 increases the tensions of two wires among the wires 110 to assist one motion of one leg. In this case, the drive control unit 122 may control the motors 114 to adjust the tensions of the wires 110 in accordance with a motion of the user 1 while keeping the tensions of the other six wires at the current value, or may stop the motors corresponding to the six wires so as not to exert the tensions on the six wires.

Figure 24:
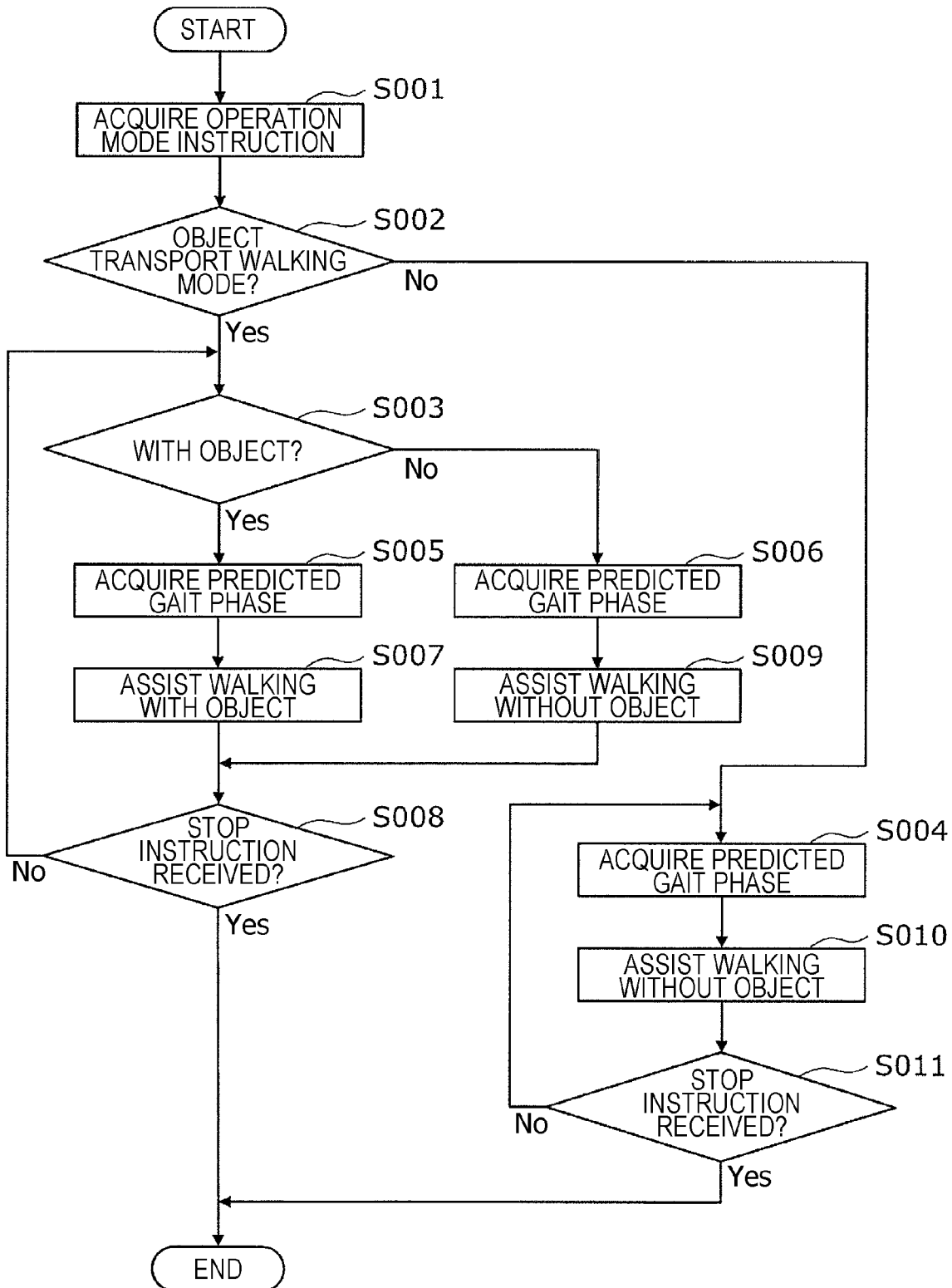
FIG. 24 is a flowchart illustrating an example overall flow of an operation of the assistance apparatus according to the embodiment for assisting a user.

3. Operation of Assistance Apparatus 3-1. Overall Operation of Assistance Apparatus Next, the overall operation flow of an assistance apparatus will be described. Since the assistance apparatus 100 according to the embodiment and the assistance apparatus 200 according to the modification are similar in terms of the overall operation flow of an assistance apparatus, the operation of the assistance apparatus 100 according to the embodiment will be described, with no description given of the operation of the assistance apparatus 200 according to the modification. FIG. 24 is a flowchart illustrating the overall flow of an operation of the assistance apparatus 100 for assisting the user 1.

As illustrated in FIG. 3 and FIG. 24, in step S001, the control unit 120 of the assistance apparatus 100 determines the operation mode of the assistance apparatus 100 in accordance with an operation mode instruction received from the user 1. Specifically, the drive control unit 122 receives an instruction for an operation mode to be performed by the assistance apparatus 100 from the input device 140 of the assistance apparatus 100 or from the terminal device 150. Examples of the operation mode include a normal walking mode in which a user walks without an object such as an item like luggage, and an object transport walking mode in which a user walks with an object. For example, the user 1 is able to select an operation mode through their decision-making on the basis of not only whether the user 1 is carrying an object but also, when the user 1 is carrying an object, the weight of the object, if necessary.

In step S002, the control unit 120 determines whether the instruction indicates the object transport walking mode. If the instruction indicates the object transport walking mode (Yes in step S002), the control unit 120 proceeds to step S003. If the instruction does not indicate the object transport walking mode (No in step S002), the control unit 120 proceeds to step S004.

In step S003, the grasp recognition unit 121 of the control unit 120 determines whether the user 1 is carrying an object. The grasp recognition unit 121 detects whether the user 1 is carrying an object on the basis of a sensor value acquired from the contact sensor 301 that the user 1 wears on their hand, and outputs a detection result to the drive control unit 122. If the grasp recognition unit 121 determines that the user 1 is carrying an object (Yes in step S003), the process proceeds to step S005. If the grasp recognition unit 121 determines that the user 1 is carrying no object (No in step S003), the process proceeds to step S006.

In step S005, the drive control unit 122 acquires a gait phase predicted by the gait timing detection unit 123. Further, in step S007, the drive control unit 122 controls the motors 114a1 to 114a4 on the basis of the acquired gait phase to generate tensions in the wires 110a1 to 110a4 of the assistance apparatus 100 with input profiles corresponding to the state of walking with an object. That is, by generating tensions in the wires 110a1 to 110a4, the drive control unit 122 assists the user 1 in flexing and extending the left and right legs. In this case, the drive control unit 122 controls the tension of the wire 110a1 on the basis of the tension of the wire 110a1, which is acquired from the force sensor 115a1, controls the tension of the wire 110a2 on the basis of the tension of the wire 110a2, which is acquired from the force sensor 115a2, controls the tension of the wire 110a3 on the basis of the tension of the wire 110a3, which is acquired from the force sensor 115a3, and controls the tension of the wire 110a4 on the basis of the tension of the wire 110a4, which is acquired from the force sensor 115a4. Accordingly, the assistance apparatus 100 assists the user 1 in walking with an object. The input profiles corresponding to the state of walking with an object will be described in detail below.

Each input profile includes a timing at which a tension is generated in a wire during a gait cycle of the left leg, a period during which a tension is generated in the wire, the value of the tension of the wire during the period, a timing at which a tension is generated in a wire during a gait cycle of the right leg, a period during which a tension is generated in the wire, and the value of the tension of the wire during the period. The input profiles are set in advance and are stored in the storage unit 125. While receiving assistance provided by the assistance apparatus 100, the user 1 may adjust the timing of generation of a wire tension, the period of generation of the wire tension, and the value of the wire tension via the input device 140 or the terminal device 150. The drive control unit 122 may reflect the adjustment results to change the input profile, and may store the changed input profile in the storage unit 125. The drive control unit 122 may control the wire tension by using the changed input profile.

Then, in step S008, the drive control unit 122 determines whether a stop instruction for stopping assistance provided by the assistance apparatus 100 has been acquired from the user 1. If the stop instruction has been acquired (Yes in step S008), the drive control unit 122 stops the operation of the assistance apparatus 100 and terminates the series of processes. If no stop instruction is acquired (No in step S008), the process returns to step S003. The stop instruction may be an instruction for changing the operation mode.

In step S006, the drive control unit 122 acquires a gait phase predicted by the gait timing detection unit 123. Further, in step S009, the drive control unit 122 controls the motors 114a1 to 114a4 on the basis of the acquired gait phase to generate tensions in the wires 110a1 to 110a4 of the assistance apparatus 100 with input profiles corresponding to the state of walking without an object. The drive control unit 122 controls the tension of the wire 110a1 on the basis of the tension of the wire 110a1, which is acquired from the force sensor 115a1, controls the tension of the wire 110a2 on the basis of the tension of the wire 110a2, which is acquired from the force sensor 115a2, controls the tension of the wire 110a3 on the basis of the tension of the wire 110a3, which is acquired from the force sensor 115a3, and controls the tension of the wire 110a4 on the basis of the tension of the wire 110a4, which is acquired from the force sensor 115a4, to assist the user 1 in flexing and extending the left and right legs. Accordingly, the assistance apparatus 100 assists the user 1 in walking without an object. The input profiles corresponding to the state of walking without an object will be described in detail below. After the processing of step S009, the drive control unit 122 proceeds to step S008.

In step S004, the drive control unit 122 acquires a gait phase predicted by the gait timing detection unit 123. Further, in step S010, the drive control unit 122 controls the motors 114a1 to 114a4 on the basis of the acquired gait phase to generate tensions in the wires 110a1 to 110a4 of the assistance apparatus 100 with input profiles corresponding to the state of walking without an object. The input profiles in step S010 may be equal to the input profiles in step S009. The drive control unit 122 controls the tension of the wire 110a1 on the basis of the tension of the wire 110a1, which is acquired from the force sensor 115a1, controls the tension of the wire 110a2 on the basis of the tension of the wire 110a2, which is acquired from the force sensor 115a2, controls the tension of the wire 110a3 on the basis of the tension of the wire 110a3, which is acquired from the force sensor 115a3, and controls the tension of the wire 110a4 on the basis of the tension of the wire 110a4, which is acquired from the force sensor 115a4, to assist the user 1 in flexing and extending the left and right legs. Accordingly, the assistance apparatus 100 assists the user 1 in walking without an object.

Then, in step S011, the drive control unit 122 determines whether a stop instruction for stopping assistance provided by the assistance apparatus 100 has been acquired from the user 1. If the stop instruction has been acquired (Yes in step S011), the drive control unit 122 stops the operation of the assistance apparatus 100 and terminates the series of processes. If no stop instruction is acquired (No in step S011), the process returns to step S004. The stop instruction may be an instruction for changing the operation mode.

As described above, the assistance apparatus 100 assists a user in walking in accordance with the normal walking mode or the object transport walking mode, which is selected by the user. In the object transport walking mode, the assistance apparatus 100 changes the input profiles of tensions, each of which is generated in one of the wires 110a1 to 110a4, in accordance with whether the user is carrying an object, and assists the user in accordance with the state of the user.

3-2. Description of Operation of Assistance Apparatus in First Pattern

The operation of an assistance apparatus in a first pattern will be described. The operation in the first pattern is an operation of an assistance apparatus for assisting a user in walking when the user walks forward while neither carrying nor holding an object such as an item. A description will be given of a relationship in the operation in the first pattern between a wire for which a tension is to be increased and the timing of increasing the tension of the wire in assistance for flexion and extension of each of the left and right legs of a user who is walking forward. The operation of the assistance apparatus 100 according to the embodiment and the operation of the assistance apparatus 200 according to the modification are the same, except that the number of wires in which tensions are to be generated for assistance for flexion and extension and maximum tension values are different. Thus, the following describes the operation of the assistance apparatus 100 according to the embodiment, with no description given of the operation of the assistance apparatus 200 according to the modification. The operation in the first pattern, that is, assistance for forward walking of a user who is carrying no object, is an example of first assistance.

The drive control unit 122 of the assistance apparatus 100 determines, based on a wire-tension relationship for a type of assistance, namely, either of flexion and extension, wires in which tensions are to be generated, pulling tensions of the wires, and the timing at which and the period during which the tensions of the wires are generated, and assists motions of the user. For example, FIG. 25 illustrates an example operation of the assistance apparatus 100 for assisting a user in walking forward without an object.

Figure 25:
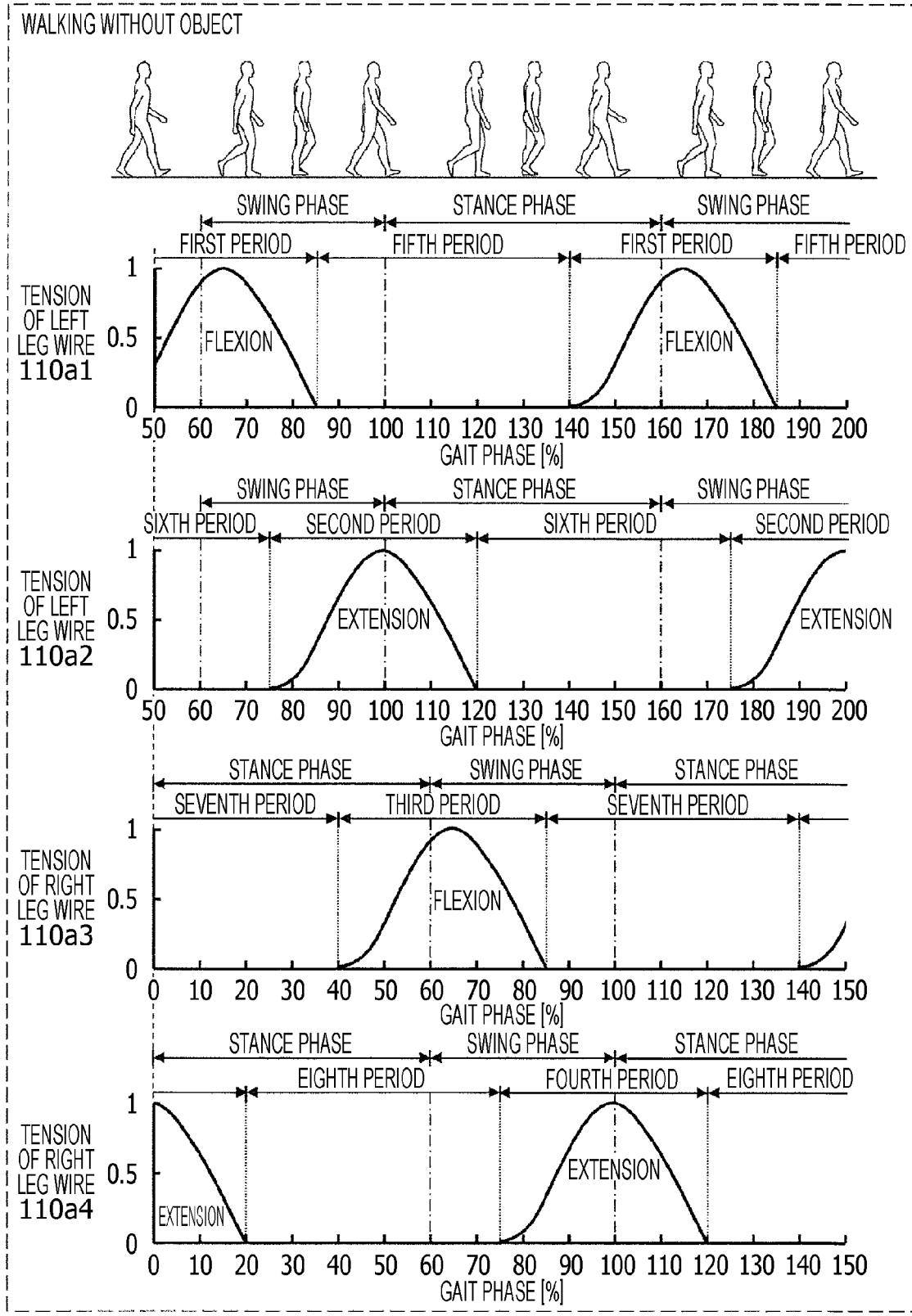
FIG. 25 is a diagram illustrating an example operation of the assistance apparatus according to the embodiment for assisting a user in walking forward without an object.

In FIG. 25, a relationship is illustrated among a gait state of a user, a gait phase of each leg, and the swing phase and stance phase of each leg. In the illustration of FIG. 25, the gait phase of each leg, wires in which tensions are to be generated, and the states of the tensions of the wires, that is, the input profiles of wire tensions, are associated with each other. An input profile of a wire tension represents the ratio of a wire tension to a maximum tension to be generated in each wire (also referred to as tension gain). For example, when the tension gain of each wire is 100 N, a tension to be actually generated is represented by an expression of a tension value stipulated in the input profile×extension gain. During a period of 0 to 100% of a gait phase, the assistance apparatus 100 produces a wire tension while changing the wire tension, with a maximum tension being 100 N.

In the example illustrated in FIG. 25, the assistance apparatus 100 assists both flexion and extension of the left and right legs of the user. As described above, the assistance apparatus 100 generates a tension in the wire 110a1 to apply an assistance force for flexion to the left leg, and generates a tension in the wire 110a2 to apply an assistance force for extension to the left leg. The assistance apparatus 100 generates a tension in the wire 110a3 to apply an assistance force for flexion to the right leg, and generates a tension in the wire 110a4 to apply an assistance force for extension to the right leg. The assistance apparatus 100 may assist either flexion or extension of the left and right legs of the user, instead of both flexion and extension of the left and right legs of the user.

In FIG. 25, the gait phase of the right leg is used as a reference gait phase. In the gait phase of the right leg, heel strike of the right leg occurs at 0%, and heel strike of the left leg occurs at 50%. In this embodiment, as a non-limiting example, a time point of 0% of the gait phase of the right leg corresponds to a time point of 50% of the gait phase of the left leg. In the example illustrated in FIG. 25, the gait phase of the right leg is used as a reference gait phase, for convenience of illustration. The gait phase of either leg may be used as a reference gait phase, and the gait phase of one leg need not be used as a reference gait phase.

The stance phase of the right leg is a period of 0% or more and 60% or less of the gait phase of the right leg, and the swing phase of the right leg is a period of more than 60% and less than 100% of the gait phase of the right leg.

The swing phase of the left leg is a period of more than 60% and less than 100% of the gait phase of the left leg, and the stance phase of the left leg is a period of 100% or more and 160% or less of the gait phase of the left leg. In the gait phase of the left leg, a period of more than 60% and less than 100% of the gait phase of the left leg, which is the swing phase of the left leg, is included in a first gait cycle of the left leg, and a period of 100% or more and 160% or less of the gait phase of the left leg, which is the stance phase of the left leg, is included in a second gait cycle of the left leg, which is subsequent to the first gait cycle of the left leg. That is, a period of 100% or more and 160% or less of the gait phase of the left leg corresponds to a period of 0% or more and 60% or less of the second gait phase of the left leg. In the following description, a gait phase represented using a value greater than or equal to 100% means a gait phase subsequent to a gait phase represented using a value of 0% to 100%. In FIG. 25, furthermore, a gait phase represented using a value over 100% may be converted into a value of 0% to 100% and represented using the value of 0% to 100%.

When assisting the user in walking forward, for example, the assistance apparatus 100 applies an assistance force for flexion to the left leg at a timing of about 40% of the gait phase of the left leg. A timing of about 40% of the gait phase of the left leg is included in the stance phase of the left leg and the swing phase of the right leg. Specifically, a timing of about 40% of the gait phase of the left leg is a timing immediately before the right leg touches the ground during the swing phase. At this time, the center of gravity of the body of the user shifts forward. When assisting the user in walking forward, for example, the assistance apparatus 100 applies an assistance force for flexion to the right leg at a timing of about 40% of the gait phase of the right leg. A timing of about 40% of the gait phase of the right leg is included in the swing phase of the left leg and the stance phase of the right leg. Specifically, a timing of about 40% of the gait phase of the right leg is a timing immediately before the left leg touches the ground during the swing phase. At this time, the center of gravity of the body of the user shifts forward.

Further, the assistance apparatus 100 applies an assistance force for extension to the left leg at a timing of about 75% of the gait phase of the left leg, for example. A timing of about 75% of the gait phase of the left leg is included in the swing phase of the left leg and the stance phase of the right leg. Specifically, a timing of about 75% of the gait phase of the left leg is a timing in the middle of moving the left leg of the user forward during the swing phase and is included in the period during which the center of gravity of the body of the user shifts from backward to forward. Further, the assistance apparatus 100 applies an assistance force for extension to the right leg at a timing of about 75% of the gait phase of the right leg, for example. A timing of about 75% of the gait phase of the right leg is included in the stance phase of the left leg and the swing phase of the right leg. Specifically, a timing of about 75% of the gait phase of the right leg is a timing in the middle of moving the right leg of the user forward during the swing phase and is included in the period during which the center of gravity of the body of the user shifts from backward to forward.

When assisting the user in walking forward, the assistance apparatus 100 generates a tension greater than or equal to a first threshold value in each of the wires 110a1 to 110a4. In the example illustrated in FIG. 25, the respective tensions of the wires 110a1 to 110a4 are 100 N, for example. The first threshold value may be a tension value that allows the user to recognize that flexion or extension is promoted by a tension generated in a wire. The first threshold value is, for example, 40 N, which is 40% of 100 N. In the example illustrated in FIG. 25, the assistance apparatus 100 generates a wire tension in each of the wires 110a1 to 110a4 in such a manner that the wire tension gradually increases, reaches a maximum tension, and then gradually decreases during the period of generation of the wire tension. The input profiles of the wire tensions generated in the wires 110a1 to 110a4 by the assistance apparatus 100 each exhibit a waveform that is convex curve. In this example, the maximum tension is 100 N.

To assist flexion of the left leg, for example, the assistance apparatus 100 continuously generates a tension in the wire 110a1 during the entirety of a first period, which is a period of 40% or more and 85% or less of the gait phase of the left leg. Then, the assistance apparatus 100 generates a tension greater than or equal to the first threshold value in the wire 110a1 during at least a portion of the first period. In the first period, the left leg shifts from the stance phase to the swing phase. Applying an assistance force for flexion to the left leg in the shift from the stance phase to the swing phase allows the user to easily raise the left leg and ensures that the user can easily walk.

In the example illustrated in FIG. 25, the assistance apparatus 100 generates no tension in the wire 110a1 during a fifth period, which is a period other than the first period. The fifth period may be a period of 0% or more and less than 40% of the gait phase of the left leg and a period of more than 85% and less than 100% of the gait phase of the left leg. However, the assistance apparatus 100 may generate a tension during the fifth period. For example, the assistance apparatus 100 may generate a tension less than a second threshold value in the wire 110a1 during the fifth period. The second threshold value is a tension value that is smaller than the first threshold value and that is not perceivable by the user, for example. For example, the second threshold value may be a tension value that prevents the wire 110a1 from loosening. The second threshold value is a value that is 0.2 to 0.4 times the first threshold value or is 10 N, for example. In the specification and the appended claims, generation of a tension smaller than the second threshold value means generation of a tension greater than or equal to 0 and less than the second threshold value and includes generation of a tension of 0.

The start timing of the first period may be included in a period of 35% or more and 55% or less of the gait phase of the left leg. The end timing of the first period may be included in a period of 80% or more and 90% or less of the gait phase of the left leg. In the example illustrated in FIG. 25, the wire tension is maximum at a timing of 65% of the gait phase of the left leg. However, the wire tension may be maximum at a time during a period of 60% or more and 70% or less of the gait phase of the left leg. Thus, the first period may be a period of 35% or more and 90% or less of the gait phase of the left leg.

To assist extension of the left leg, for example, the assistance apparatus 100 continuously generates a tension in the wire 110a2 during the entirety of a second period, which is a period of 75% or more and 120% or less of the gait phase of the left leg. Then, the assistance apparatus 100 generates a tension greater than or equal to the first threshold value in the wire 110a2 during at least a portion of the second period. In the second period, the left leg shifts from the swing phase to the stance phase. Applying an assistance force for extension to the left leg in the shift from the swing phase to the stance phase allows the left leg of the user to touch the ground stably and ensures that the user can easily walk. In the example illustrated in FIG. 25, the assistance apparatus 100 generates no tension in the wire 110a2 during a sixth period, which is a period other than the second period. The sixth period may be a period of more than 20% and less than 75% of the gait phase of the left leg. However, the assistance apparatus 100 may generate a tension less than the second threshold value during the sixth period.

The start timing of the second period may be included in a period of 65% or more and 90% or less of the gait phase of the left leg. The end timing of the second period may be included in a period of 110% or more and 125% or less of the gait phase of the left leg. In the example illustrated in FIG. 25, the wire tension is maximum at a timing of 100% of the gait phase of the left leg. However, the wire tension may be maximum at a time during a period of 85% or more and 100% or less of the gait phase of the left leg. Thus, the second period may be a period of 65% or more and 125% or less of the gait phase of the left leg, that is, may include a period of 0% or more and 25% or less of the gait phase of the left leg and a period of 65% or more and less than 100% of the gait phase of the left leg.

To assist flexion of the right leg, for example, the assistance apparatus 100 continuously generates a tension in the wire 110a3 during the entirety of a third period, which is a period of 40% or more and 85% or less of the gait phase of the right leg. Then, the assistance apparatus 100 generates a tension greater than or equal to the first threshold value in the wire 110a3 during at least a portion of the third period. In the third period, the right leg shifts from the stance phase to the swing phase. In the example illustrated in FIG. 25, the assistance apparatus 100 generates no tension in the wire 110a3 during a seventh period, which is a period other than the third period. However, the assistance apparatus 100 may generate a tension less than the second threshold value during the seventh period. The seventh period may be a period of 0% or more and less than 40% of the gait phase of the right leg and a period of more than 85% and less than 100% of the gait phase of the right leg.

The start timing of the third period may be included in a period of 35% or more and 55% or less of the gait phase of the right leg. The end timing of the third period may be included in a period of 80% or more and 90% or less of the gait phase of the right leg. In the example illustrated in FIG. 25, the wire tension is maximum at a timing of 65% of the gait phase of the right leg. However, the wire tension may be maximum at a time during a period of 60% or more and 70% or less of the gait phase of the right leg. Thus, the third period may be a period of 35% or more and 90% or less of the gait phase of the right leg.

To assist extension of the right leg, for example, the assistance apparatus 100 continuously generates a tension in the wire 110a4 during the entirety of a fourth period, which is a period of 75% or more and 120% or less of the gait phase of the right leg. Then, the assistance apparatus 100 generates a tension greater than or equal to the first threshold value in the wire 110a4 during at least a portion of the fourth period. In the fourth period, the right leg shifts from the swing phase to the stance phase. In the example illustrated in FIG. 25, the assistance apparatus 100 generates no tension in the wire 110a4 during an eighth period, which is a period other than the fourth period. However, the assistance apparatus 100 may generate a tension less than the second threshold value during the eighth period.

The start timing of the fourth period may be included in a period of 65% or more and 90% or less of the gait phase of the right leg. The end timing of the fourth period may be included in a period of 110% or more and 125% or less of the gait phase of the right leg. In the example illustrated in FIG. 25, the wire tension is maximum at a timing of 100% of the gait phase of the right leg. However, the wire tension may be maximum at a time during a period of 85% or more and 100% or less of the gait phase of the right leg. Thus, the fourth period may be a period of 65% or more and 125% or less of the gait phase of the right leg, that is, may include a period of 0% or more and 25% or less of the gait phase of the right leg and a period of 65% or more and less than 100% of the gait phase of the right leg.

As described above, during the entirety of a period corresponding to each input profile of a wire tension, the assistance apparatus 100 continuously generates a tension in the wire corresponding to the input profile. However, the embodiment is not limited to this. The assistance apparatus 100 may temporarily stop the generation of the tension in the wire during the period corresponding to the input profile. In this case, a load imposed on the leg of the user by the assistance apparatus 100 is reduced, and the load felt by the user on which the assistance apparatus 100 acts is reduced.

The input profiles of wire tensions illustrated in FIG. 25 are set so that the tension of each wire rises earlier than a desired time point by several percent (%) of the gait phase in consideration of a time delay from when the drive control unit 122 outputs a signal to the corresponding motor to when a tension is actually generated in the wire. For example, in the example illustrated in FIG. 25, input profiles of wire tensions are created so that the tension of each wire rises earlier than a desired time point by approximately 5%. For assistance for flexion, the assistance apparatus 100 provides assistance so that the assistance for flexion is completed immediately before the heel strikes the ground. Thus, input profiles of wire tensions are created so that assistance for flexion ends at a time during a period of 80% or more and 90% or less of the gait phase of the each leg in order to complete assistance for flexion at a timing of about 100% of the gait phase of each leg in consideration of a delay of output of the tension of each wire.

3-3. Description of Operation of Assistance Apparatus in Second Pattern

Figure 26:
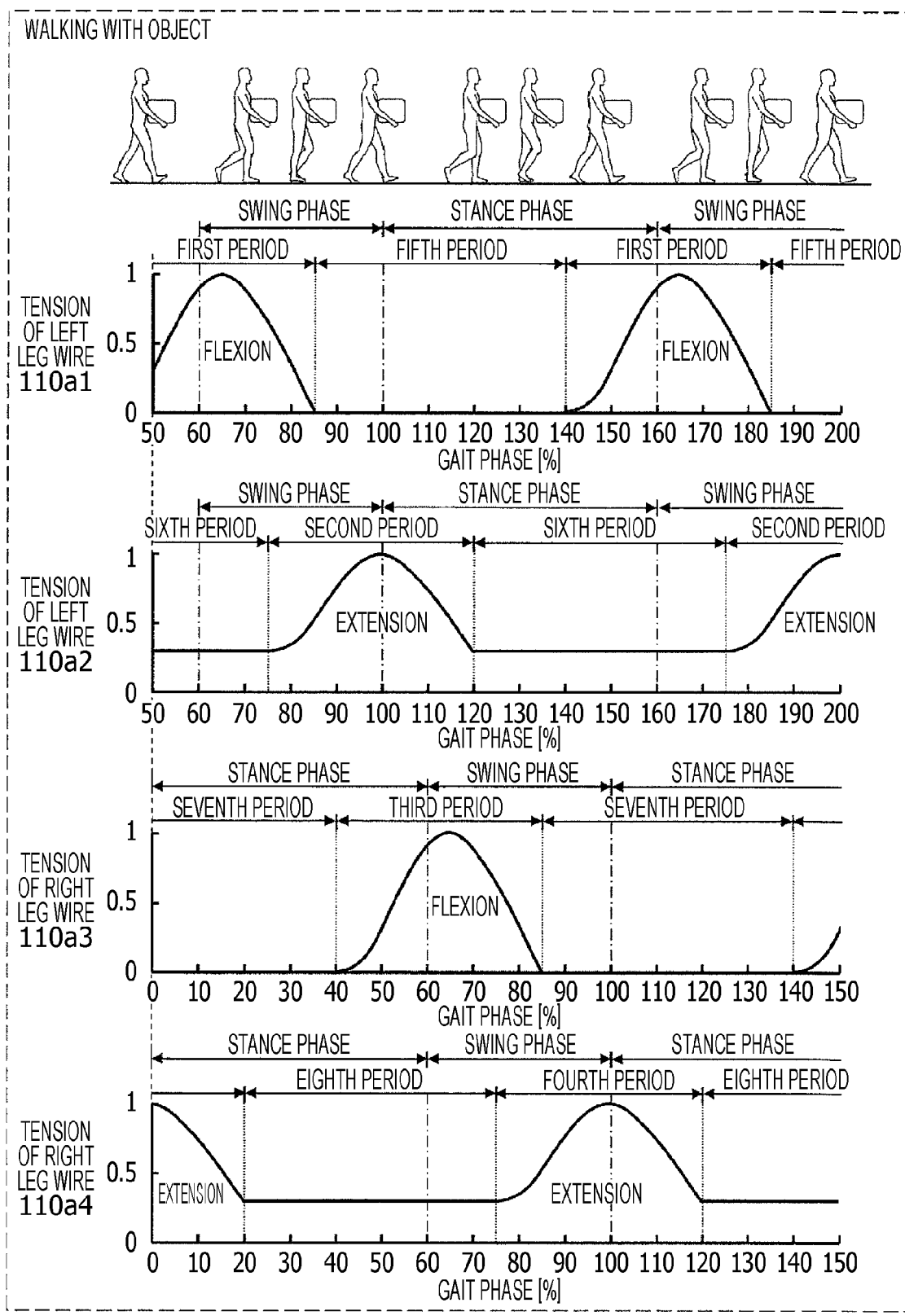
FIG. 26 is a diagram illustrating an example operation of the assistance apparatus according to the embodiment for assisting a user in walking forward with an object.

The operation of the assistance apparatus 100 in a second pattern will be described. The operation in the second pattern is an operation of the assistance apparatus 100 for assisting a user in walking when the user walks forward while carrying an object. For example, FIG. 26 illustrates an example operation of the assistance apparatus 100 for assisting a user in walking forward with an object. In the example illustrated in FIG. 26, the assistance apparatus 100 assists both flexion and extension of the left and right legs of the user. The assistance apparatus 100 produces a wire tension while changing the wire tension, with a maximum tension being 100 N. The operation in the second pattern, that is, assistance for forward walking of a user who is carrying an object, is an example of second assistance.

When assisting flexion of a user during forward walking with an object, the assistance apparatus 100 generates wire tensions in the wire 110a1 of the left leg and the wire 110a3 of the right leg in a way similar to that for a user during forward walking without an object described above.

When assisting extension of the left leg, for example, the assistance apparatus 100 continuously generates a tension in the wire 110a2 during the entirety of a second period, which is a period of 75% or more and 120% or less of the gait phase of the left leg. Then, the assistance apparatus 100 generates a wire tension greater than or equal to the first threshold value in the wire 110a2 during at least a portion of the second period. Then, the assistance apparatus 100 continuously generates a tension greater than or equal to the third threshold value and less than or equal to a fourth threshold value in the wire 110a2 during the entirety of a sixth period, which is a period other than the second period. The sixth period may be a period of more than 20% and less than 75% of the gait phase of the left leg. The tension of the wire 110a2 in the sixth period is greater than the tension of the wire 110a1 in the fifth period and is greater than the tension of the wire 110a2 in the sixth period during the operation in the first pattern. Then, the assistance apparatus 100 continuously generates a tension greater than the wire tension in the sixth period in the wire 110a2 during the entirety of the second period. Thus, the assistance apparatus 100 continuously generates a tension greater than or equal to the second threshold value in the wire 110a2 during an entire period including the second period and the sixth period. The fourth threshold value is a value less than the maximum wire tension. The fourth threshold value is, for example, a value given by an expression of maximum tension×0.6.

When assisting extension of the right leg, for example, the assistance apparatus 100 continuously generates a tension in the wire 110a4 during the entirety of a fourth period, which is a period of 75% or more and 120% or less of the gait phase of the right leg. Then, the assistance apparatus 100 generates a wire tension greater than or equal to the first threshold value in the wire 110*a*4 during at least a portion of the fourth period. Then, the assistance apparatus 100 continuously generates a tension greater than or equal to the second threshold value and less than or equal to the fourth threshold value in the wire 110*a*4 during the entirety of an eighth period, which is a period other than fourth period. The eighth period may be a period of more than 20% and less than 75% of the gait phase of the right leg. The tension of the wire 110*a*4 in the eighth period is greater than the tension of the wire 110*a*3 in the seventh period and is greater than the tension of the wire 110*a*4 in the eighth period during the operation in the first pattern. Then, the assistance apparatus 100 continuously generates a tension greater than the wire tension in the eighth period in the wire 110*a*4 during the entirety of the fourth period. Thus, the assistance apparatus 100 continuously generates a tension greater than or equal to the second threshold value in the wire 110*a*4 during an entire period including the fourth period and the eighth period.

As described above, a tension greater than or equal to the second threshold value is generated in the wires 110*a*2 and 110*a*4, which are located on or above the back part of the body of the user, during the entirety of a period over which the assistance apparatus 100 provides assistance. Thus, the user is subjected to the action such that the left and right legs are pulled backward all the time during walking. When the user is holding an object in the front part of the body, the center of gravity of the body of the user tends to be moved forward. Thus, the user, who is holding an object in the front part of the body, is subjected to the action such that the tensions of the wires 110*a*2 and 110*a*4 cause the user to walk forward with the center of gravity of the body being kept at the center of gravity position in the upright posture. This enables the user to walk with a stable posture. Accordingly, the user is able to transport an object with comfort. In the fifth period, the tension of the wire 110*a*1 for assisting flexion of the left leg is small, and thus the action exerted by the tension of the wire 110*a*2 is achieved while being less affected by the tension of the wire 110*a*1. In the seventh period, the tension of the wire 110*a*3 for assisting flexion of the right leg is small, and thus the action exerted by the tension of the wire 110*a*4 is achieved while being less affected by the tension of the wire 110*a*3.

Figure 27:
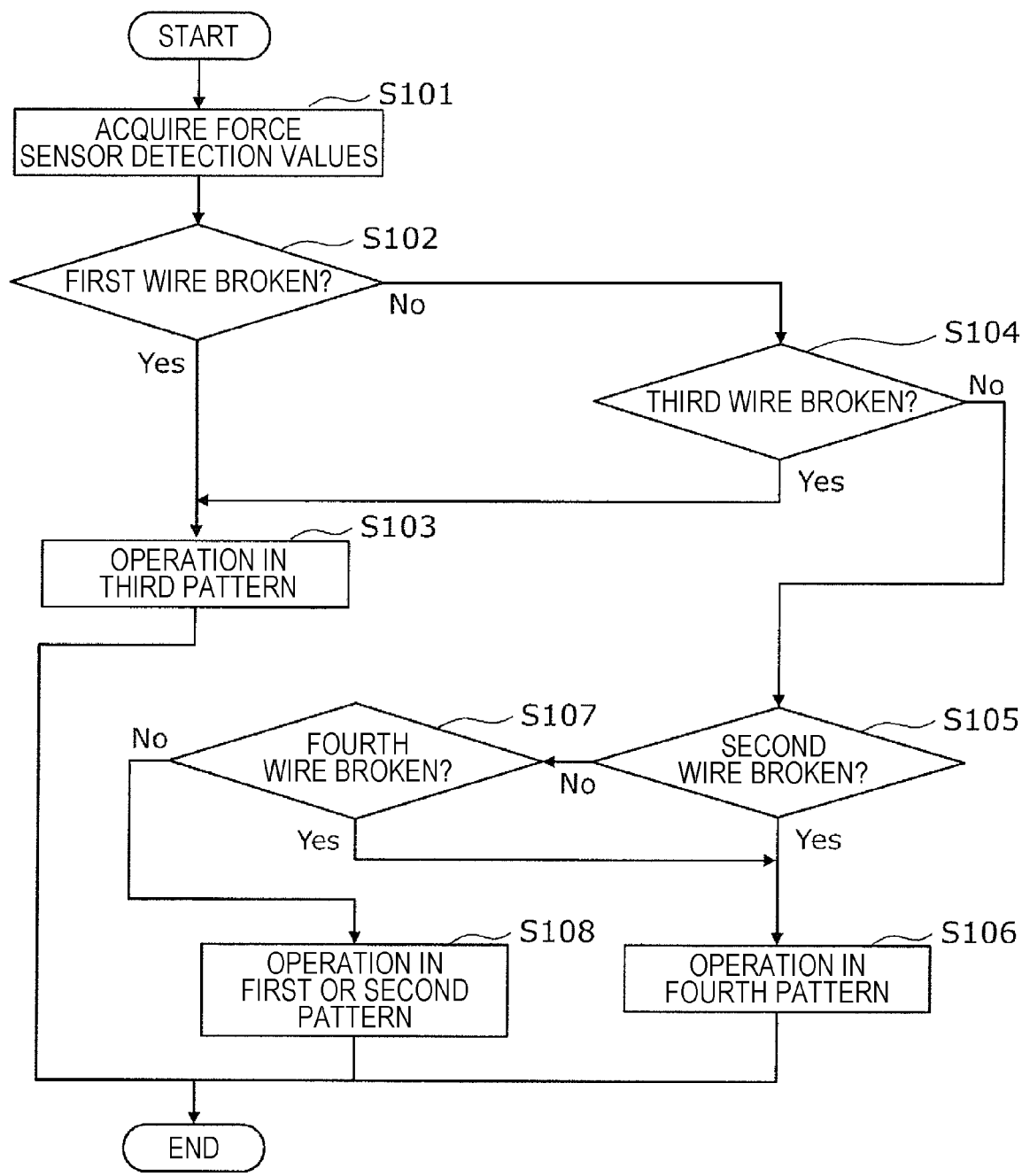
FIG. 27 is a flowchart illustrating an example flow of an operation of the assistance apparatus according to the embodiment when a wire is broken.

3-3. Description of Operations of Assistance Apparatus in Third and Fourth Patterns The operations of the assistance apparatus 100 in a third pattern and a fourth pattern will be described. The operation in the third pattern and the operation in the fourth pattern are operations performed by the assistance apparatus 100 when any one of the wires 110*a*1 to 110*a*4 is broken. Specifically, the operation in the third pattern is an operation performed by the assistance apparatus 100 when at least one of the wires 110*a*1 and 110*a*3 is broken during the operation in the first or second pattern. The operation in the fourth pattern is an operation performed by the assistance apparatus 100 when at least one of the wires 110*a*2 and 110*a*4 is broken during the operation in the first or second pattern. For example, FIG. 27 is a flowchart illustrating an example flow of the operation of the assistance apparatus 100 when a wire is broken. In the example illustrated in FIG. 27, the assistance apparatus 100 assists both flexion and extension of the left and right legs of the user. At this time, the assistance apparatus 100 produces a wire tension while changing the wire tension, with a maximum tension being 100 N.

The overall operation of the assistance apparatus 100 when at least one of the wires 110*a*1 to 110*a*4 is broken will be described with reference to FIG. 27. In step S101, the control unit 120 of the assistance apparatus 100 acquires signals, that is, detection values that are sensor values, from the force sensors 115*a*1 to 115*a*4. At this time, the assistance apparatus 100 assists the user by using the operation in the first or second pattern.

Then, in step S102, the control unit 120 determines whether the wire 110*a*1 for assisting flexion of the left leg is broken. The wire tension recognition unit 124 of the control unit 120 calculates the tensions of the wires 110*a*1 to 110*a*4 from the signals of the force sensors 115*a*1 to 115*a*4, respectively. When the tension of the wire 110*a*1 decreases or becomes 0 although the motor 114*a*1 is driven, the drive control unit 122 of the control unit 120 determines that the wire 110*a*1 is broken. The drive control unit 122 can determine whether each of the wires 110*a*2 to 110*a*4 is broken by using a method similar to the method for determining whether the wire 110*a*1 is broken. If the wire 110*a*1 is broken (Yes in step S102), the drive control unit 122 proceeds to step S103. If the wire 110*a*1 is not broken (No in step S102), the drive control unit 122 proceeds to step S104.

In step S103, the drive control unit 122 controls the tensions of the wires 110*a*1 to 110*a*4 in accordance with the content of the operation in the third pattern stored in the storage unit 125. The operation in the third pattern will be described in detail below.

In step S104, the drive control unit 122 determines whether the wire 110*a*3 for assisting flexion of the right leg is broken by using a method similar to the determination method of step S102. If the wire 110*a*3 is broken (Yes in step S104), the drive control unit 122 proceeds to step S103. If the wire 110*a*3 is not broken (No in step S104), the drive control unit 122 proceeds to step S105.

In step S105, the drive control unit 122 determines whether the wire 110*a*2 for assisting extension of the left leg is broken by using a method similar to the determination method of step S102. If the wire 110*a*2 is broken (Yes in step S105), the drive control unit 122 proceeds to step S106. If the wire 110*a*2 is not broken (No in step S105), the drive control unit 122 proceeds to step S107.

In step S106, the drive control unit 122 controls the tensions of the wires 110*a*1 to 110*a*4 in accordance with the content of the operation in the fourth pattern stored in the storage unit 125. The operation in the fourth pattern will be described in detail below.

In step S107, the drive control unit 122 determines whether the wire 110*a*4 for assisting extension of the right leg is broken by using a method similar to the determination method of step S102. If the wire 110*a*4 is broken (Yes in step S107), the drive control unit 122 proceeds to step S106. If the wire 110*a*4 is not broken (No in step S107), the drive control unit 122 proceeds to step S108.

In step S108, the drive control unit 122 controls the tensions of the wires 110*a*1 to 110*a*4 in accordance with the operation in the first or second pattern, which is currently being performed.

The control unit 120 repeatedly performs the series of processing operations of steps S101 to S108 to detect which of the wires 110*a*1 to 110*a*4 is broken, and controls the tensions of the wires 110*a*1 to 110*a*4 in accordance with the operation in a pattern selected on the basis of the detection result.

Next, the operation in the third pattern will be described in detail. For example, FIG. 28 illustrates an example operation of the assistance apparatus 100 in the third pattern when the wire 110*a*1 is broken during the operation in the first pattern in which no object is carried.

Figure 28:
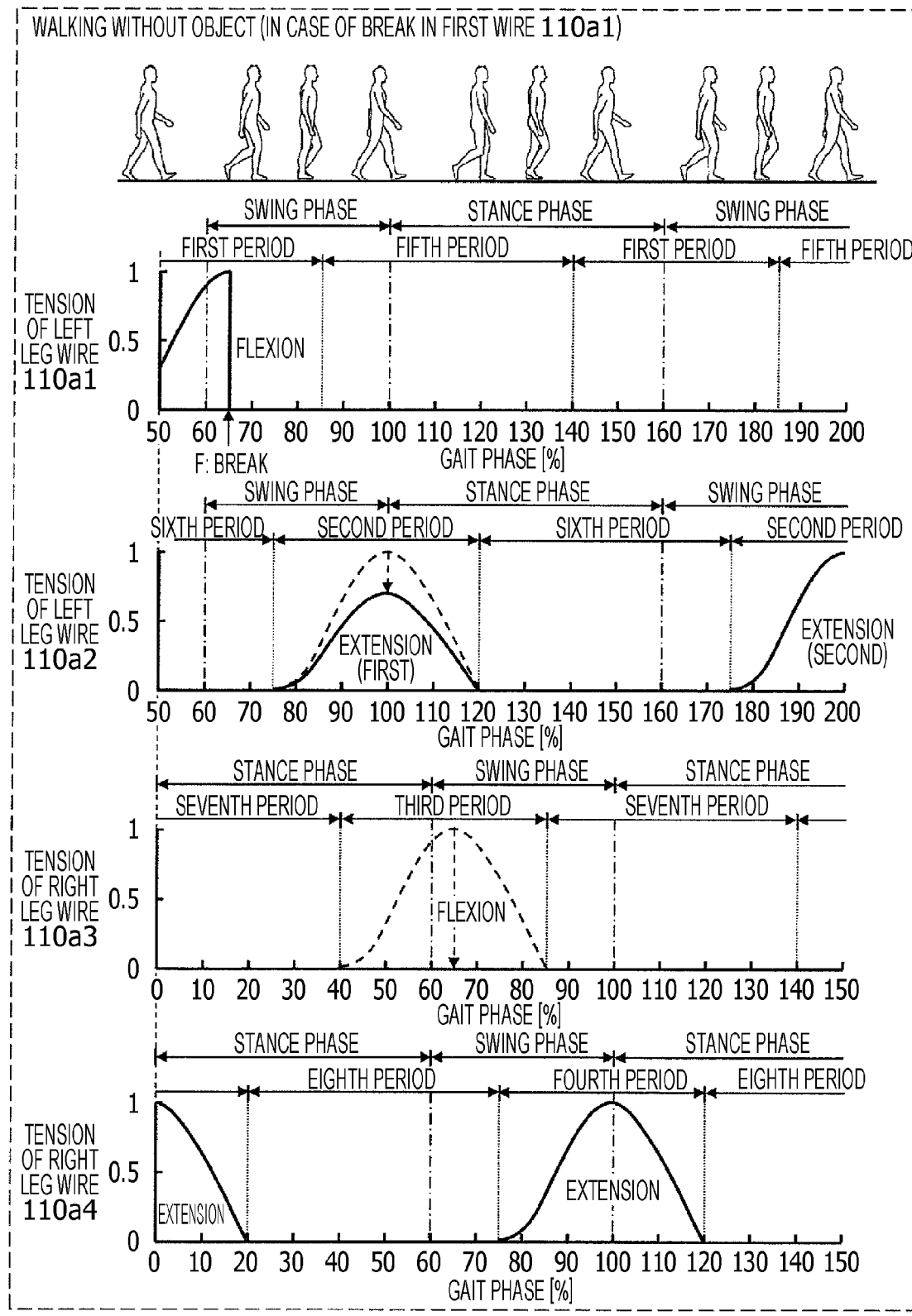
FIG. 28 is a diagram illustrating an example operation of the assistance apparatus according to the embodiment in a third pattern when a wire is broken during an operation in a first pattern in which no object is carried.

As illustrated in FIG. 28, upon detection of a break in the wire 110*a*1 at a time point F in a period of 0 to 100% of a gait phase of the left leg, the drive control unit 122 decreases the maximum value of the tension of the second wire 110*a*2 during a second period in the gait phase of the left leg that appears first at and after the break time point F, which is the timing at which the wire 110*a*1 is broken. In the example illustrated in FIG. 28, the break time point F corresponds to a time point of approximately 65% of the gait phase of the left leg. Thus, the drive control unit 122 determines a period of 75 to 120% of the gait phase of the left leg as the initial second period.

Then, the drive control unit 122 changes the input profile of the wire tension of the wire 110*a*2 during the determined second period to an input profile whose maximum tension is reduced. Specifically, the maximum wire tension of the wire 110*a*2 is changed to a maximum tension that is 0.4 to 0.8 times the original maximum tension. For example, in the example illustrated in FIG. 28, the original maximum tension, e.g., 100 N, in a period during which no break occurs in the wire 110*a*1 is changed to a maximum tension that is 0.6 times, namely, to 60 N. The drive control unit 122 uses the input profile of the wire tension corresponding to the changed maximum tension. The duration over which a tension is generated using the changed input profile is equal to the duration over which a tension is generated using the original input profile. As illustrated in FIG. 28, furthermore, the waveform of the original input profile may be similar to the waveform of the changed input profile. The changed input profile may be created in advance and stored in the storage unit 125, or may be created by the drive control unit 122 in accordance with the changed maximum tension.

When the break time point F is included in a period more than 20% and less than 75% of the gait phase of the left leg, the drive control unit 122 determines a second period, which is a period of 75 to 120% of the gait phase of the left leg, as the initial second period. The initial second period does not include the break time point F. Then, as described above, the drive control unit 122 changes the entire input profile of the wire tension of the wire 110*a*2 in the initial second period to an input profile whose maximum tension is reduced. In this way, the assistance apparatus 100 weakens the assistance force for extension to be applied for the first time at and after the break time point F to the left leg, for which the wire 110*a*1 for assisting flexion is broken, compared with that in the second period before the break in the wire 110*a*1.

When the break time point F is included in a period of 0% or more and 20% or less of the gait phase of the left leg or in a period of 75% or more and 100% or less of the gait phase of the left leg, the drive control unit 122 uses a different wire tension input profile than that described above. During these periods, the drive control unit 122 generates a tension in the wire 110*a*2. When the break time point F is included in a period of 0% or more and 20% or less of the gait phase of the left leg, the drive control unit 122 determines a second period starting from the break time point F and ending at a time point of 20% of the gait phase of the left leg as the initial second period. When the break time point F is included in a period of 75% or more and 100% or less of the gait phase of the left leg, the drive control unit 122 determines a second period starting from the break time point F and ending at a time point of 120% of the gait phase of the left leg as the initial second period. In these cases, the initial second period includes the break time point F. During the initial second period, the drive control unit 122 does not generate a tension greater than the tension generated at the break time point F in the wire 110*a*2. In the initial second period, the tension generated at the break time point F is the greatest tension at and after the break time point F.

When a second period starting from the break time point F and ending at a time point of 20% of the gait phase of the left leg is the initial second period, the drive control unit 122 gradually decreases the tension of the wire 110*a*2 from the tension generated at the break time point F to a tension generated at the time point of 20% of the gait phase of the left leg over an entire period from the break time point F to the time point of 20% of the gait phase of the left leg. When a second period starting from the break time point F and ending at a time point of 120% of the gait phase of the left leg is the initial second period, the drive control unit 122 gradually decreases the tension of the wire 110*a*2 from the tension generated at the break time point F to a tension generated at the time point of 120% of the gait phase of the left leg over an entire period from the break time point F to the time point of 120% of the gait phase of the left leg. To prevent the user from feeling a rapid change in the level of assistance, the tension may be reduced slowly and smoothly. Accordingly, the drive control unit 122 uses an input profile in which the tension of the wire 110*a*2 is reduced in a period from the break time point F to the end time point of the initial second period. The assistance apparatus 100, which performs the operation described above, weakens the assistance force for extension to be applied for the first time at and after the break time point F to the left leg, for which the wire 110*a*1 for assisting flexion is broken, compared with that before the break in the wire 110*a*1.

Further, the drive control unit 122 reduces a tension to be generated in the wire 110*a*3 at and after the break time point F to a level smaller than the second threshold value. For example, in the example illustrated in FIG. 28, the drive control unit 122 generates a tension of 0 in the wire 110*a*3. Thus, in all third periods at and after the break time point F within the gait phase of the right leg, the drive control unit 122 does not assist flexion of the right leg using a tension greater than or equal to the first threshold value. When the break time point F is included in a third period, the drive control unit 122 may reduce the tension to be generated in the wire 110*a*3 to a level smaller than the second threshold value during a third period next to the third period including the break time point F and during the following third periods. Alternatively, the drive control unit 122 may reduce the tension to be generated in the wire 110*a*3 to a level smaller than the second threshold value stepwise over two or more third periods. The two or more third periods may include the third period next to the third period including the break time point F and the third period coming after the next third period.

Further, in a second period that appears next to the initial second period at and after the break time point F within the gait phase of the left leg, that is, during the second-appearing second period, the drive control unit 122 returns the input profile of the wire tension of the wire 110*a*2 to the original input profile, which is used in a period during which no break occurs in the wire 110*a*1. For example, in the example illustrated in FIG. 28, the drive control unit 122 generates a tension in the wire 110*a*2 during the second-appearing second period in accordance with an input profile whose maximum tension is 100 N. In the second- and subsequently-appearing second periods, the drive control unit 122 controls the tension of the wire 110*a*2 in accordance with an input profile used in a period during which no wire break occurs.

The drive control unit 122 controls the wire tension for the wire 110a4 at and after the break time point F illustrated in FIG. 28 in a way similar to that in a period during which no break occurs in the wire 110a1. That is, the drive control unit 122 does not change tension control for the wire 110a4 before and after the break time point F.

Figure 29:
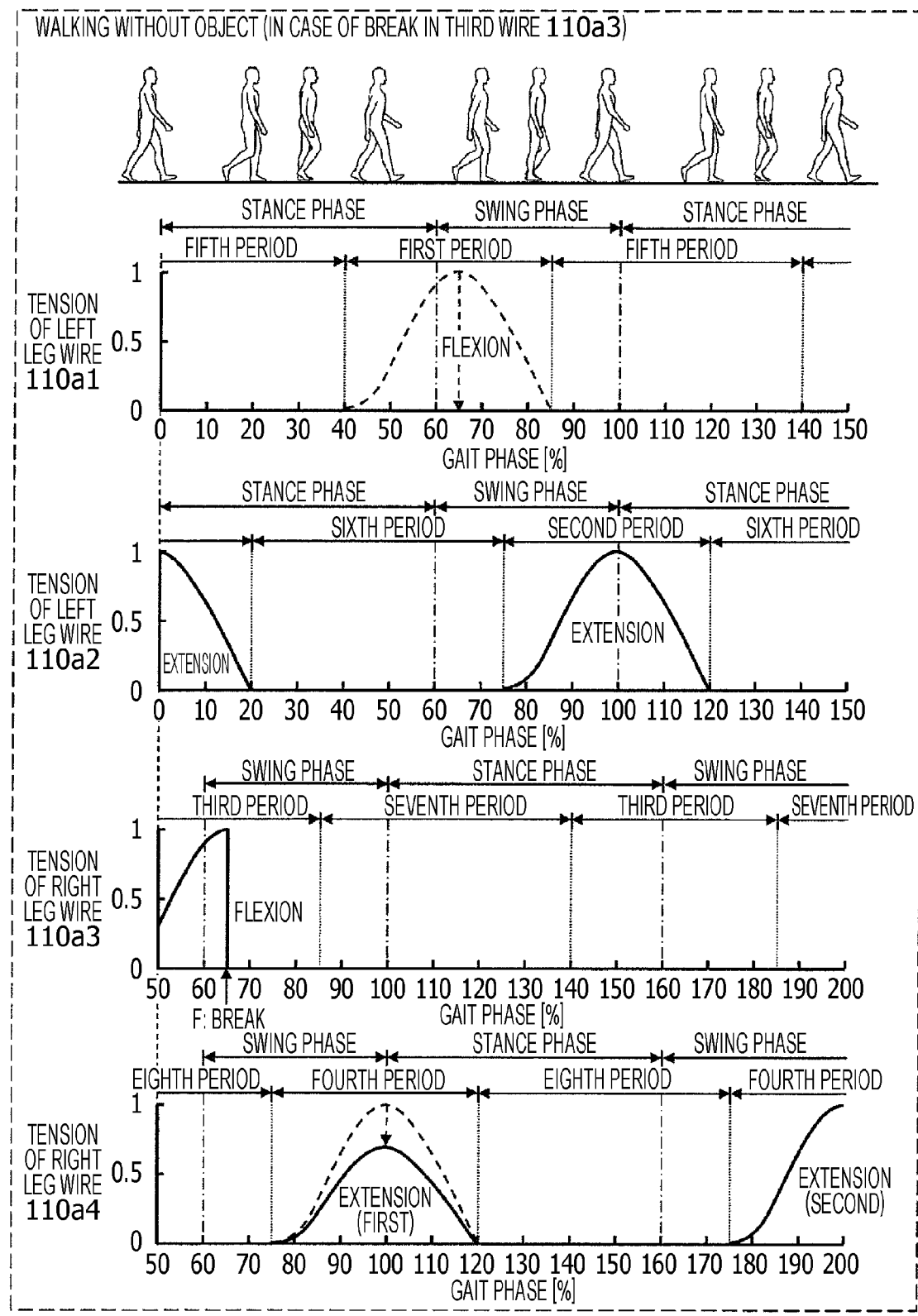
FIG. 29 is a diagram illustrating an example operation of the assistance apparatus according to the embodiment in the third pattern when a wire is broken during the operation in the first pattern in which no object is carried.

FIG. 29 illustrates an example operation of the assistance apparatus 100 in the third pattern when the wire 110a3 is broken during the operation in the first pattern in which no object is carried. In the example illustrated in FIG. 29, a break in the wire 110a3 is detected at a time point F in a period of 0 to 100% of a gait phase of the right leg. Specifically, the break time point F is a time point of approximately 65% of the gait phase of the right leg. Also in this case, the drive control unit 122 performs tension control on the wire 110a4 in a way similar to that on the wire 110a2 in the example illustrated in FIG. 28. That is, in the initial fourth period at and after the break time point F within the gait phase of the right leg, the drive control unit 122 controls the tension of the wire 110a4 in accordance with an input profile having a lower maximum tension. In the second- and subsequently-appearing fourth periods at and after the break time point F, the drive control unit 122 controls the tension of the wire 110a4 in accordance with the original input profile, which is used before the break in the wire 110a3. Further, the drive control unit 122 performs tension control on the wire 110a1 in a way similar to that on the wire 110a3 in the example illustrated in FIG. 28. That is, the drive control unit 122 reduces the tension of the wire 110a1 at and after the break time point F to a level lower than the second threshold value. Further, the drive control unit 122 performs tension control on the wire 110a2 in a way similar to that on the wire 110a4 in the example illustrated in FIG. 28. That is, the drive control unit 122 does not change tension control for the wire 110a2 before and after the break time point F.

As described above, when the wire 110a1 for assisting flexion of the left leg is broken, the drive control unit 122 generates a wire tension in the wire 110a2 during the initial second period. The wire tension in the wire 110a2 during the initial second period is smaller than that in a period during which the wire 110a1 is unbroken. The wire 110a2 for assisting extension and the broken wire 110a1 are provided to assist the same lag in the situation. Then, the drive control unit 122 generates the same wire tension as that when there is no wire break in the wire 110a2 during the second- and subsequently-appearing second periods after the break time point F within the gait phase. Further, the drive control unit 122 reduces the tension of the wire 110a3, which is not broken, to a level smaller than the second threshold value at and after the break time point F.

As described above, when the wire 110a3 for assisting flexion of the right leg is broken, the drive control unit 122 generates a wire tension in the wire 110a4 during the initial fourth period. The wire tension in the wire 110a4 during the initial fourth period is smaller than that in a period during which the wire 110a3 is unbroken. The wire 110a4 for assisting extension and the broken wire 110a3 are provided to assist the same lag in the situation. Then, the drive control unit 122 generates the same wire tension as that when there is no wire break in the wire 110a4 during the second- and subsequently-appearing fourth periods after the break time point F within the gait phase. Further, the drive control unit 122 reduces the tension of the wire 110a1, which is not broken, to a level smaller than the second threshold value at and after the break time point F.

Accordingly, when the wire 110a1 for assisting flexion of the left leg is broken, the assistance apparatus 100 weakens the assistance force for extension of the left leg to be applied for the first time at and after the break time point F, compared with the assistance force for extension of the left leg which is applied before the break in the wire 110a1. For example, if a wire break suddenly stops exerting an assistance force for flexion on the left leg, the user is likely to disrupt the balance between the movements of the left and right legs and can fall. When the wire 110a1 for assisting flexion of the left leg is broken, the assistance force to be applied for the first time at and after the break time point F to the left leg is weakened, which may prevent the user from disrupting the balance between the movements of the left and right legs.

When the wire 110a3 for assisting flexion of the right leg is broken, the assistance apparatus 100 weakens the assistance force for extension of the right leg to be applied for the first time at and after the break time point F, compared with the assistance force for extension of the right leg which is applied before the break in the wire 110a3. For example, if a wire break suddenly stops exerting an assistance force for flexion on the right leg, the user is likely to disrupt the balance between the movements of the left and right legs and can fall. When the wire 110a3 for assisting flexion of the right leg is broken, the assistance force to be applied for the first time at and after the break time point F to the right leg is weakened, which may prevent the user from disrupting the balance between the movements of the left and right legs.

When the wire 110a1 for assisting flexion of the left leg is broken, furthermore, the assistance apparatus 100 makes the assistance forces for extension to be applied to the left leg for the second and following times, among assistance forces for extension to be applied to the left leg at and after the break time point F, equal to the assistance force for extension that is applied to the left leg before the break in the wire 110a1. The timing at which an assistance force for extension is applied to the left leg for the second and following times corresponds to a time point when one or more gait cycles elapse after the break time point F. At this time point, the user is likely to restore the balance between the movements of the left and right legs to a stable state from an unstable state immediately after a wire break has occurred. Thus, when the wire 110a1 for assisting flexion of the left leg is broken, the assistance force for extension to be applied to the left leg less affects the body balance of the user even if the assistance force is made equal to an assistance force for extension to be applied to the left leg in a period during which no wire break occurs. Further, the assistance apparatus 100 applies a uniform and sufficiently strong assistance force for extension to the left and right legs of the user.

When the wire 110a3 for assisting flexion of the right leg is broken, furthermore, the assistance apparatus 100 makes the assistance forces for extension to be applied to the right leg for the second and following times, among assistance forces for extension to be applied to the right leg at and after the break time point F, equal to the assistance force for extension that is applied to the right leg before the break in the wire 110a3. The timing at which an assistance force for extension is applied to the right leg for the second and following times corresponds to a time point when one or more gait cycles elapse after the break time point F. At this time point, the user is likely to restore the balance between the movements of the left and right legs to a stable state from an unstable state immediately after a wire break has occurred. Thus, when the wire 110a3 for assisting flexion of the right leg is broken, the assistance force for extension to be applied to the right leg less affects the body balance of the user even if the assistance force is made equal to an assistance force for extension to be applied to the right leg in a period during which no wire break occurs. Further, the assistance apparatus 100 applies a uniform and sufficiently strong assistance force for extension to the left and right legs of the user.

Further, the assistance apparatus 100 reduces the tension of the wire 110a1, which is broken, and the tension of the wire 110a3, which is not broken, to values less than the second threshold value. This prevents unbalanced assistance for flexion of the left and right legs from being provided to the user and allows the user to maintain the balance between the movements of the left and right legs. The assistance apparatus 100 reduces the tension of the wire 110a3, which is broken, and the tension of the wire 110a1, which is not broken, to values less than the second threshold value. This prevents unbalanced assistance for flexion of the left and right legs from being provided to the user and allows the user to maintain the balance between the movements of the left and right legs.

As described above, when the wire 110a1 is broken, the assistance apparatus 100 controls the tensions of the wires 110a1 to 110a4 in accordance with the input profiles of the wire tensions illustrated in FIG. 28. Further, for example, if the wire 110a3, which is not broken, is broken after the wire 110a1 has been broken, the assistance apparatus 100 may continuously control the tensions of the wires 110a1 to 110a4 in accordance with the input profiles of the wire tensions illustrated in FIG. 29 or may stop assistance.

As described above, when the wire 110a3 is broken, the assistance apparatus 100 controls the tensions of the wires 110a1 to 110a4 in accordance with the input profiles of the wire tensions illustrated in FIG. 29. Further, for example, if the wire 110a1, which is not broken, is broken after the wire 110a3 has been broken, the assistance apparatus 100 may continuously control the tensions of the wires 110a1 to 110a4 in accordance with the input profiles of the wire tensions illustrated in FIG. 28 or may stop assistance.

Figure 30:
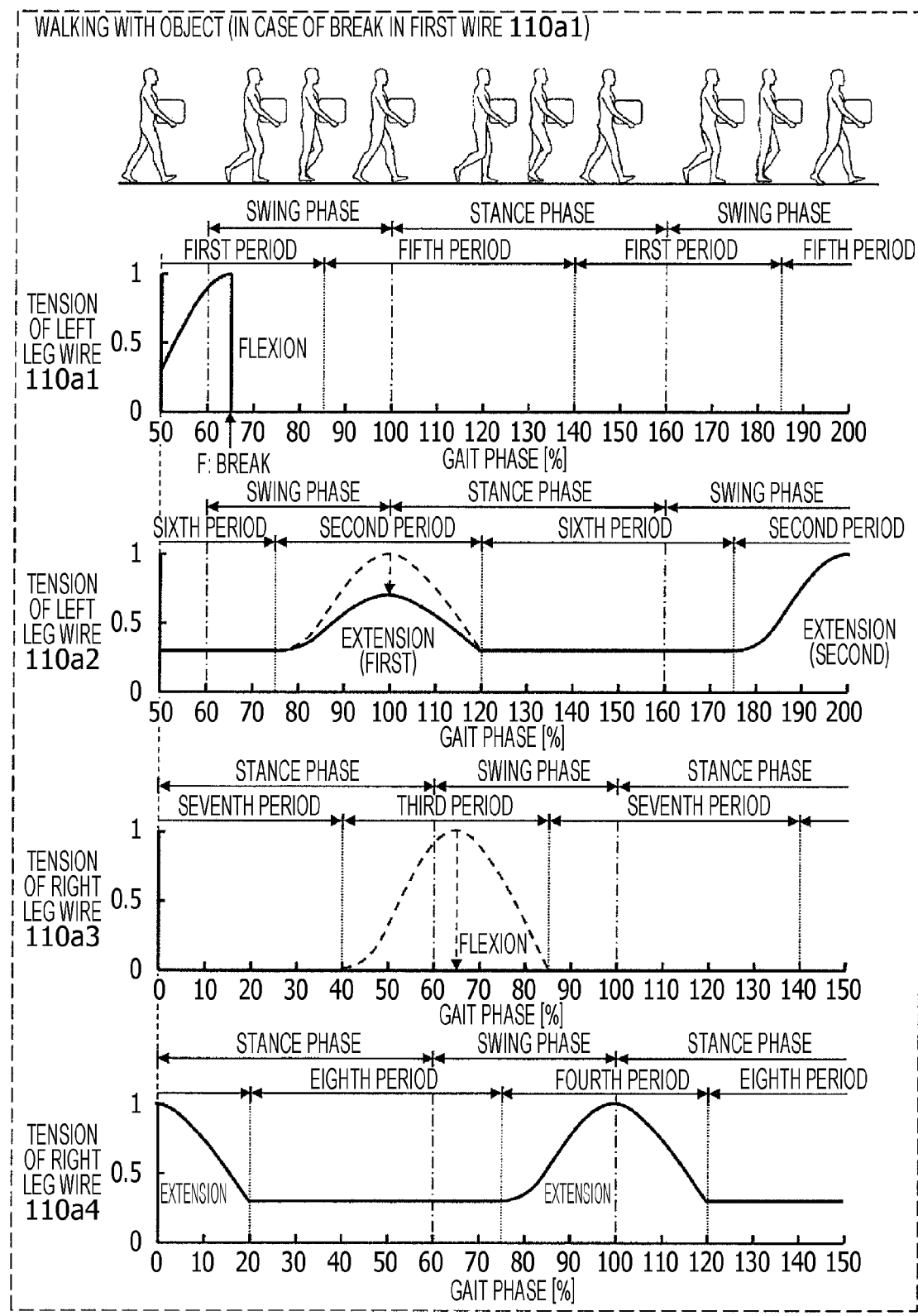
FIG. 30 is a diagram illustrating an example operation of the assistance apparatus according to the embodiment in the third pattern when a wire is broken during an operation in a second pattern in which an object is carried.

FIG. 30 illustrates an example operation of the assistance apparatus 100 in the third pattern when the wire 110a1 is broken during the operation in the second pattern in which an object is carried. In this case, the drive control unit 122 also controls wire tension in a way similar to that in the example illustrated in FIG. 28.

Specifically, the drive control unit 122 decreases the maximum value of the tension of the wire 110a2 during a second period in the gait phase of the left leg that appears first at and after the break time point F at which the wire 110a1 is broken. In the initial second period, the drive control unit 122 controls the tension of the wire 110a2 by using an input profile whose maximum tension matches the changed maximum tension. In the second- and subsequently-appearing second periods at and after the break time point F within the gait phase of the left leg, the drive control unit 122 controls the tension of the wire 110a2 by using the input profile used in a period during which no break occurs in the wire 110a1. Further, during a sixth period in the gait phase of the left leg, the drive control unit 122 continuously generates a tension greater than or equal to the second threshold value and less than or equal to the fourth threshold value in the wire 110a2, regardless of whether the wire 110a1 is broken. That is, before and after the break time point F, the drive control unit 122 continuously generates a tension greater than or equal to the second threshold value and less than or equal to the fourth threshold value in the wire 110a2.

Further, the drive control unit 122 reduces a tension to be generated in the wire 110a3 at and after the break time point F to a level smaller than the second threshold value. Further, the drive control unit 122 controls the wire tension for the wire 110a4 at and after the break time point F in a way similar to when no break occurs in the wire 110a1. That is, the drive control unit 122 does not change tension control for the wire 110a4 before and after the break time point F.

Figure 31:
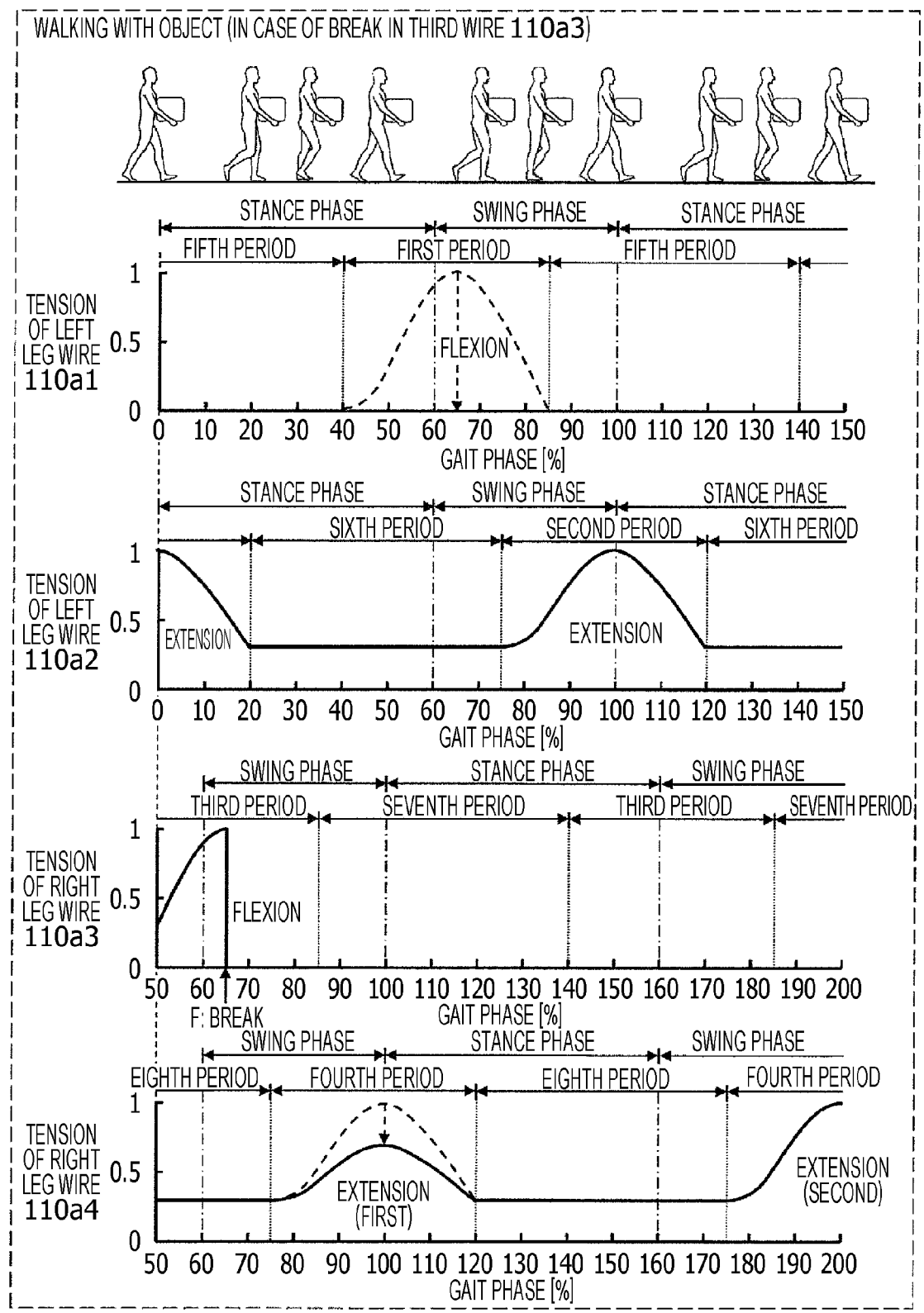
FIG. 31 is a diagram illustrating an example operation of the assistance apparatus according to the embodiment in the third pattern when a wire is broken during the operation in the second pattern in which an object is carried.

FIG. 31 illustrates an example operation of the assistance apparatus 100 in the third pattern when the wire 110a3 is broken during the operation in the second pattern in which an object is carried. Also in this case, the drive control unit 122 performs tension control on the wire 110a4 in a way similar to that on the wire 110a2 in the example illustrated in FIG. 30. That is, in the initial fourth period at and after the break time point F within the gait phase of the right leg, the drive control unit 122 controls the tension of the wire 110a4 in accordance with an input profile having a lower maximum tension. In the second- and subsequently-appearing fourth periods at and after the break time point F, the drive control unit 122 controls the tension of the wire 110a4 in accordance with the original input profile, which is used before the break in the wire 110a3. Further, the drive control unit 122 performs tension control on the wire 110a1 in a way similar to that on the wire 110a3 in the example illustrated in FIG. 30. That is, the drive control unit 122 reduces the tension of the wire 110a1 at and after the break time point F to a level lower than the second threshold value. Further, the drive control unit 122 performs tension control on the wire 110a2 in a way similar to that on the wire 110a4 in the example illustrated in FIG. 30. That is, the drive control unit 122 does not change tension control for the wire 110a2 before and after the break time point F.

Further, for example, if the wire 110a3, which is not broken, is broken after the wire 110a1 has been broken, the assistance apparatus 100 may continuously control the tensions of the wires 110a1 to 110a4 in accordance with the input profiles of the wire tensions illustrated in FIG. 31 or may stop assistance.

For example, if the wire 110a1, which is not broken, is broken after the wire 110a3 has been broken, the assistance apparatus 100 may continuously control the tensions of the wires 110a1 to 110a4 in accordance with the input profiles of the wire tensions illustrated in FIG. 30 or may stop assistance.

The assistance apparatus 100, which performs the operation described above, assists a user in walking with an object with the center of gravity of the body of the user being kept at the center of gravity position in the upright posture of the user while preventing the user from disrupting the balance between the movements of the left and right legs due to a break in the wire 110a1 or 110a3.

The operation in the fourth pattern will now be described in detail. For example, FIG. 32A and FIG. 32B illustrate an example operation of the assistance apparatus 100 in the fourth pattern when the wire 110a2 is broken during the operation in the first pattern in which no object is carried.

Figure 32A:
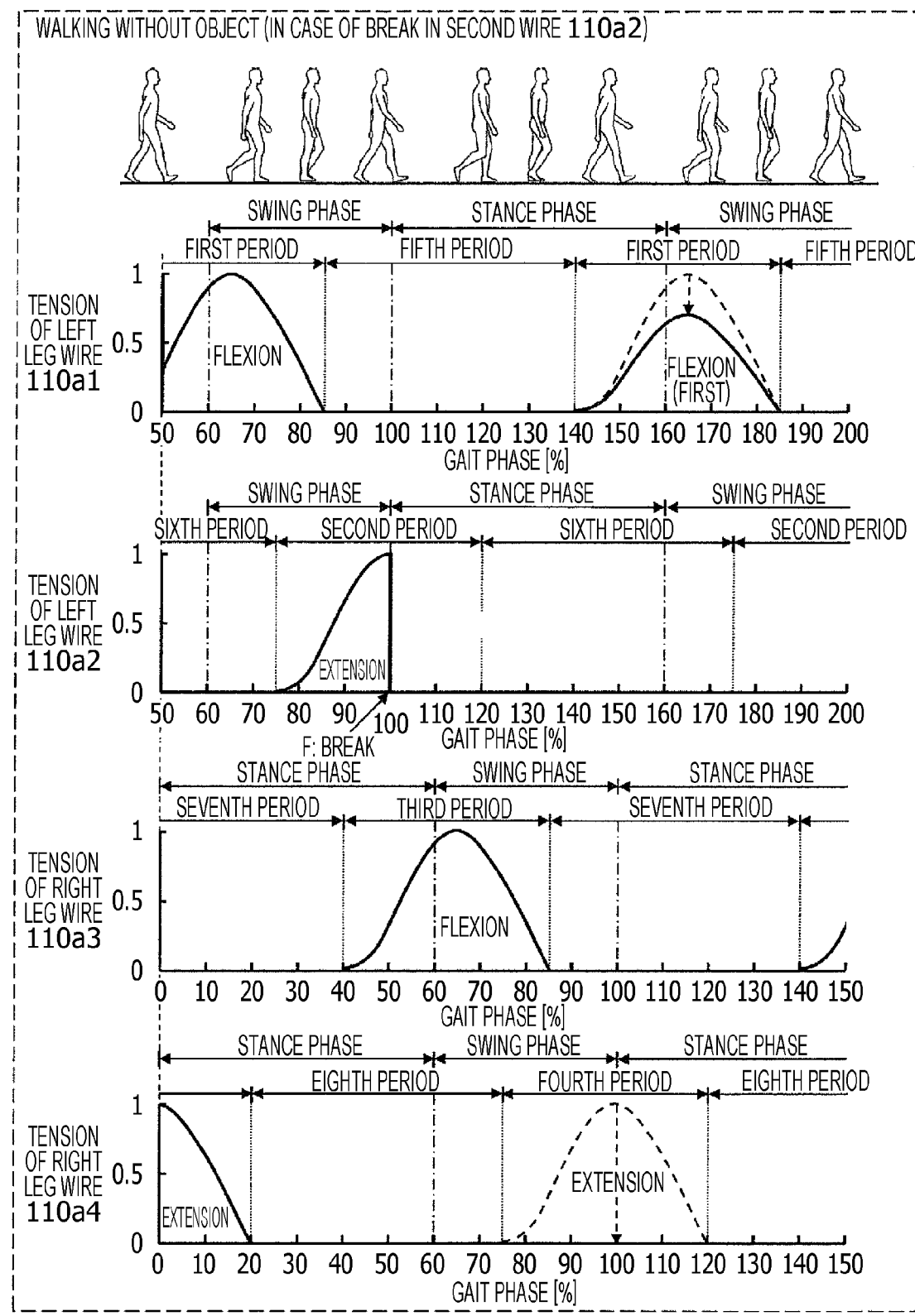
FIG. 32A is a diagram illustrating an example operation of the assistance apparatus according to the embodiment in a fourth pattern when a wire is broken during the operation in the first pattern in which no object is carried.
Figure 32B:
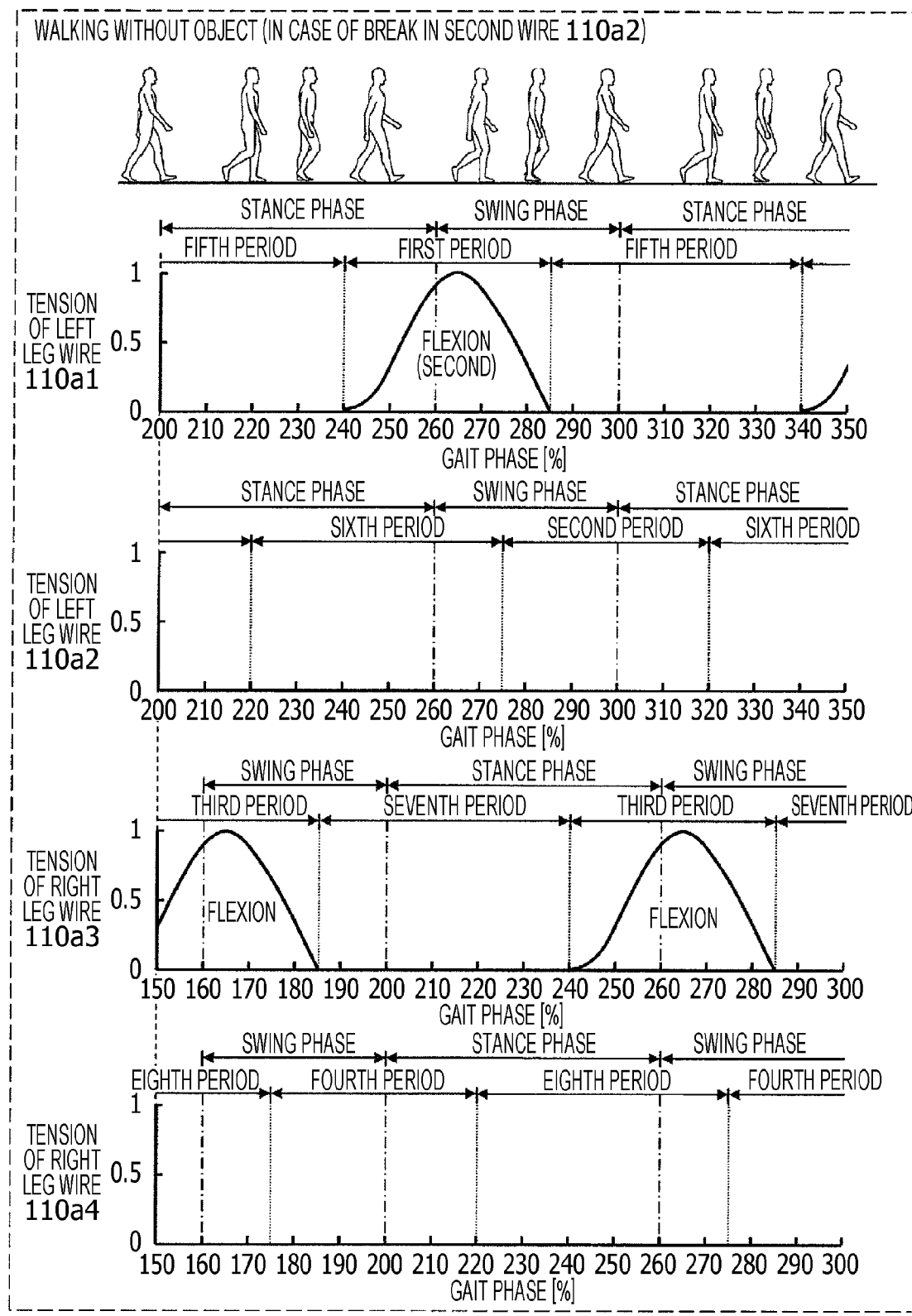
FIG. 32B is a diagram illustrating an example operation of the assistance apparatus according to the embodiment in the fourth pattern when a wire is broken during the operation in the first pattern in which no object is carried.

As illustrated in FIG. 32A and FIG. 32B, upon detection of a break in the wire 110a2 at a time point F in a period of 0 to 100% of a gait phase of the left leg, the drive control unit 122 decreases the maximum value of the tension of the wire 110a1 during a first period in the gait phase of the left leg that appears first at and after the break time point F, which is the timing at which the wire 110a2 is broken. In the illustrated example, the break time point F corresponds to a time point of approximately 100% of the gait phase of the left leg. Thus, the drive control unit 122 determines a period of 140 to 185% of the gait phase of the left leg as the initial first period.

The drive control unit 122 changes the input profile of the wire tension of the wire 110a1 during the determined first period to an input profile whose maximum tension is reduced. Specifically, the maximum wire tension of the wire 110a1 is changed to a maximum tension that is 0.4 to 0.8 times the original maximum tension. In the initial first period at and after the break time point F within the gait phase of the left leg, the drive control unit 122 controls the tension of the wire 110a1 by using an input profile whose maximum tension matches the changed maximum tension. In the second- and subsequently-appearing first periods at and after the break time point F within the gait phase of the left leg, the drive control unit 122 controls the tension of the wire 110a1 by using the input profile used in a period during which no break occurs in the wire 110a2.

When the break time point F is included in a period of 0% or more and less than 40% of the gait phase of the left leg, the drive control unit 122 determines a first period, which is a period of 40 to 85% of the gait phase of the left leg, as the initial first period. When the break time point F is included in a period of more than 85% and 100% or less of the gait phase of the left leg, the drive control unit 122 determines a first period, which is a period of 140 to 185% of the gait phase of the left leg, as the initial first period. In these cases, the initial first period does not include the break time point F. Then, as described above, the drive control unit 122 changes the entire input profile of the wire tension of the wire 110a1 in the initial first period to an input profile whose maximum tension is reduced. In this way, when the wire 110a2 for assisting extension of the left leg is broken, the assistance apparatus 100 weakens the assistance force for flexion to be applied for the first time at and after the break time point F to the left leg, compared with the assistance force for flexion to be applied to the left leg during the first period before the break in the wire 110a2.

When the break time point F is included in a period of 40% or more and 85% or less of the gait phase of the left leg, the drive control unit 122 uses a different wire tension input profile than that described above. During this period, the drive control unit 122 generates a tension in the wire 110a1. When the break time point F is included in a period of 40% or more and 85% or less of the gait phase of the left leg, the drive control unit 122 determines a first period starting from the break time point F and ending at a time point of 85% of the gait phase of the left leg as the initial first period. In this case, the initial first period includes the break time point F. During the initial first period, the drive control unit 122 does not generate a tension greater than the tension generated at the break time point F in the wire 110a1. The greatest tension at and after the break time point F is the tension generated at the break time point F. The drive control unit 122 gradually decreases the tension of the wire 110a1 from the tension generated at the break time point F to a tension generated at the time point of 85% of the gait phase of the left leg over an entire period from the break time point F to the time point of 85% of the gait phase of the left leg. To prevent the user from feeling a rapid change in the level of assistance, the tension may be reduced slowly and smoothly. Accordingly, the drive control unit 122 uses an input profile in which the tension of the wire 110a1 is reduced in a period from the break time point F to the end time point of the initial first period. The assistance apparatus 100, which performs the operation described above, weakens the assistance force for flexion to be applied for the first time at and after the break time point F to the left leg, for which the wire 110a2 for assisting extension is broken, compared with that before the break in the wire 110a2.

Further, the drive control unit 122 reduces a tension to be generated in the wire 110a4 at and after the break time point F to a level smaller than the second threshold value. That is, in all fourth periods at and after the break time point F within the gait phase of the right leg, the drive control unit 122 reduces a tension to be generated in the wire 110a4 to a level smaller than the second threshold value. For example, in the example illustrated in FIG. 32A and FIG. 32B, the drive control unit 122 generates a tension of 0 in the wire 110a4. When the break time point F is included in a fourth period, the drive control unit 122 may reduce the tension to be generated in the wire 110a4 to a level smaller than the second threshold value during a fourth period next to the fourth period including the break time point F and during the following fourth periods. Alternatively, the drive control unit 122 may reduce the tension to be generated in the wire 110a4 to a level smaller than the second threshold value stepwise over two or more fourth periods. The two or more fourth periods may include the fourth period next to the fourth period including the break time point F and the fourth period coming after the next fourth period.

Further, the drive control unit 122 performs tension control on the wire 110a3 at and after the break time point F in a way similar to when no break occurs in the wire 110a2. That is, the drive control unit 122 does not change tension control for the wire 110a3 before and after the break time point F.

Figure 33A:
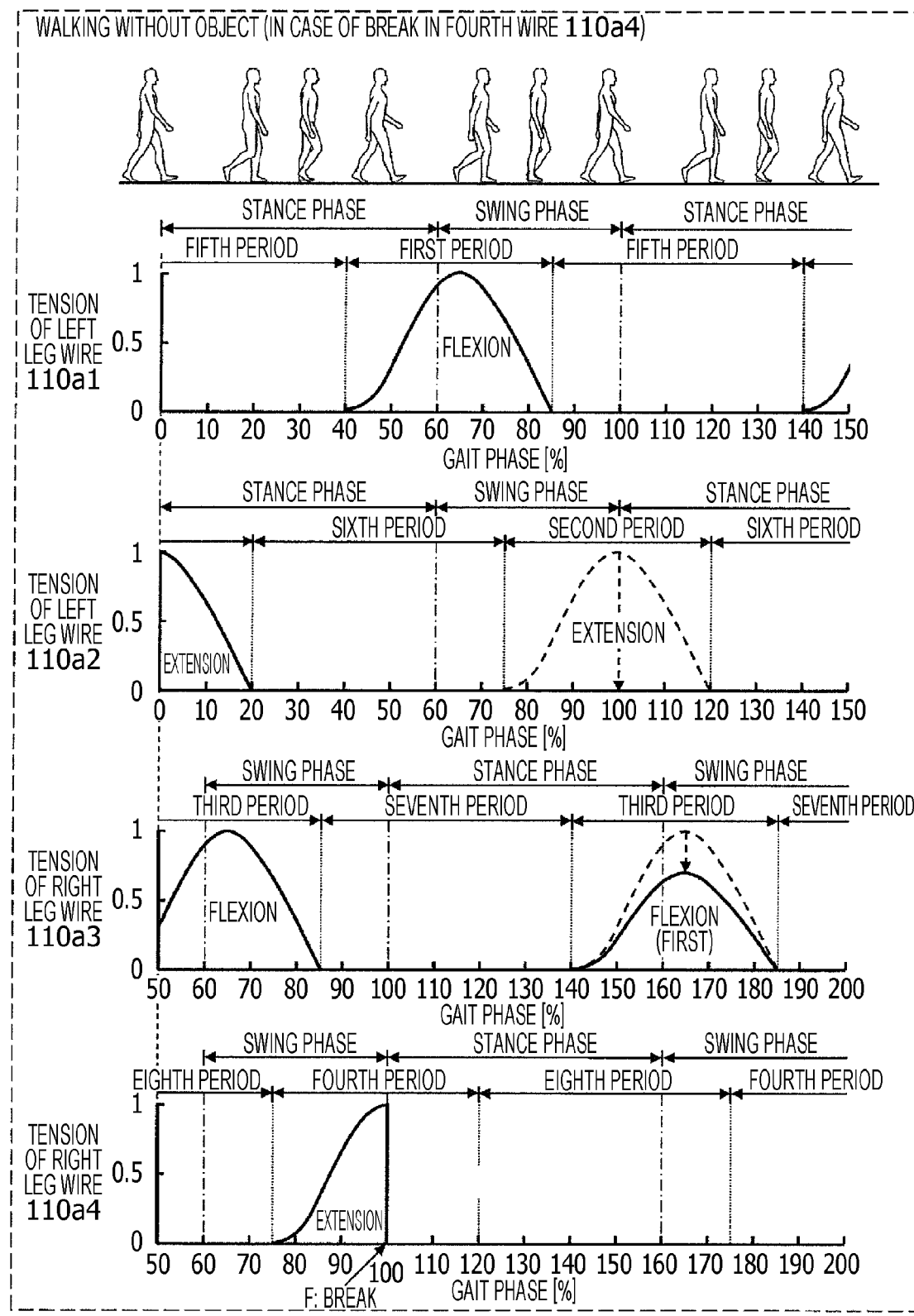
FIG. 33A is a diagram illustrating an example operation of the assistance apparatus according to the embodiment in the fourth pattern when a wire is broken during the operation in the first pattern in which no object is carried.
Figure 33B:
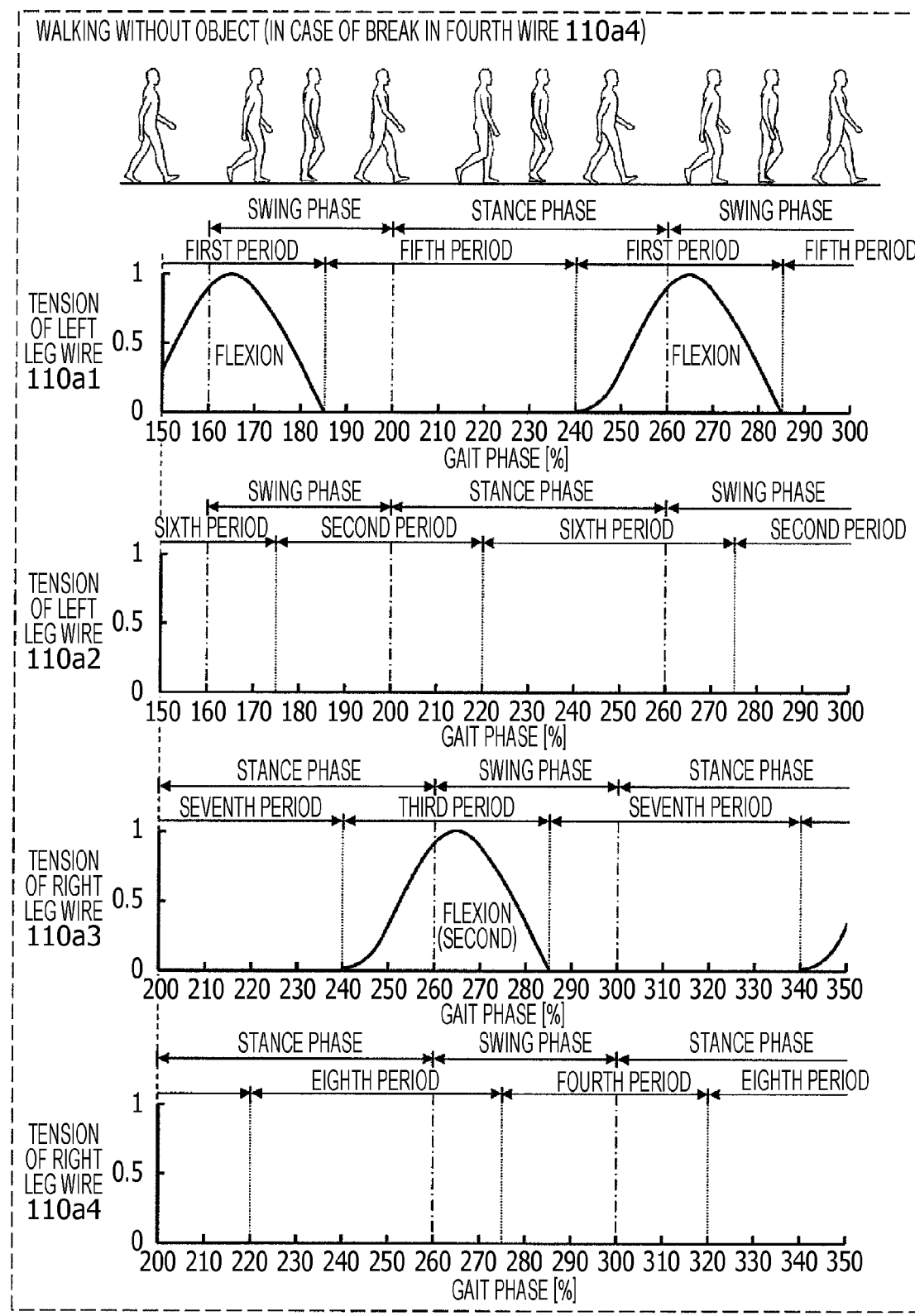
FIG. 33B is a diagram illustrating an example operation of the assistance apparatus according to the embodiment in the fourth pattern when a wire is broken during the operation in the first pattern in which no object is carried.

FIG. 33A and FIG. 33B illustrate an example operation of the assistance apparatus 100 in the fourth pattern when the wire 110a4 is broken during the operation in the first pattern. In the example illustrated in FIG. 33A and FIG. 33B, a break in the wire 110a4 is detected at a time point F in a period of 0 to 100% of a gait phase of the right leg. Specifically, the break time point F is a time point of approximately 100% of the gait phase of the right leg. Also in this case, the drive control unit 122 performs tension control on the wire 110a3 in a way similar to that on the wire 110a1 in the example illustrated in FIG. 32A and FIG. 32B. That is, in the initial third period at and after the break time point F within the gait phase of the right leg, the drive control unit 122 controls the tension of the wire 110a3 in accordance with an input profile having a lower maximum tension. In the second- and subsequently-appearing third periods at and after the break time point F, the drive control unit 122 controls the tension of the wire 110a3 in accordance with the original input profile, which is used before the break in the wire 110a4. Further, the drive control unit 122 performs tension control on the wire 110a2 in a way similar to that on the wire 110a4 in the example illustrated in FIG. 32A and FIG. 32B. That is, the drive control unit 122 reduces the wire tension at and after the break time point F to a level lower than the second threshold value. Further, the drive control unit 122 performs tension control on the wire 110a1 in a way similar to that on the wire 110a3 in the example illustrated in FIG. 32A and FIG. 32B. That is, the drive control unit 122 does not change tension control before and after the break time point F.

Further, for example, if the wire 110a4, which is not broken, is broken after the wire 110a2 has been broken, the assistance apparatus 100 may continuously control the tensions of the wires 110a1 to 110a4 in accordance with the input profiles of the wire tensions illustrated in FIG. 33A to FIG. 33B or may stop assistance.

As described above, when the wire 110a2 for assisting extension of the left leg is broken, the drive control unit 122 generates a wire tension in the wire 110a1 during the initial first period. The wire tension in the wire 110a1 during the initial first period is smaller than that in a period during which the wire 110a2 is unbroken. The wire 110a1 for assisting flexion and the broken wire 110a2 are provided to assist the same lag in the situation. Then, the drive control unit 122 generates the same wire tension as that when there is no wire break in the wire 110a1 during the second- and subsequently-appearing first periods after the break time point F within the gait phase. Further, the drive control unit 122 reduces the tension of the wire 110a4, which is not broken, to a level smaller than the second threshold value at and after the break time point F. When the wire 110a4 for assisting extension of the right leg is broken, the drive control unit 122 generates a wire tension in the wire 110a3 during the initial third period. The wire tension in the wire 110a3 during the initial third period is smaller than that in a period during which the wire 110a4 is unbroken. The wire 110a3 for assisting flexion and the broken wire 110a4 are provided to assist the same lag in the situation. Then, the drive control unit 122 generates the same wire tension as that when there is no wire break in the wire 110a3 during the second- and subsequently-appearing third periods after the break time point F within the gait phase. Further, the drive control unit 122 reduces the tension of the wire 110a2, which is not broken, to a level smaller than the second threshold value at and after the break time point F.

Accordingly, also in the operation in the fourth pattern, as in the operation in the third pattern, the assistance apparatus 100 assists the user in walking while preventing the user from disrupting the balance between the movements of the left and right legs due to a break in the wire 110a2 or 110a4. In addition, after the user restores the balance between the movements of the left and right legs to a stable state from an unstable state immediately after a wire break has occurred, the assistance apparatus 100 applies a uniform and sufficiently strong assistance force for flexion to the left and right legs of the user. Moreover, the assistance apparatus 100 reduces the tensions of the wires 110a2 and 110a4 to values less than the second threshold value at and after the break time point F, and thus does not provide unbalanced assistance for extension to the left and right legs of the user.

Figure 34:
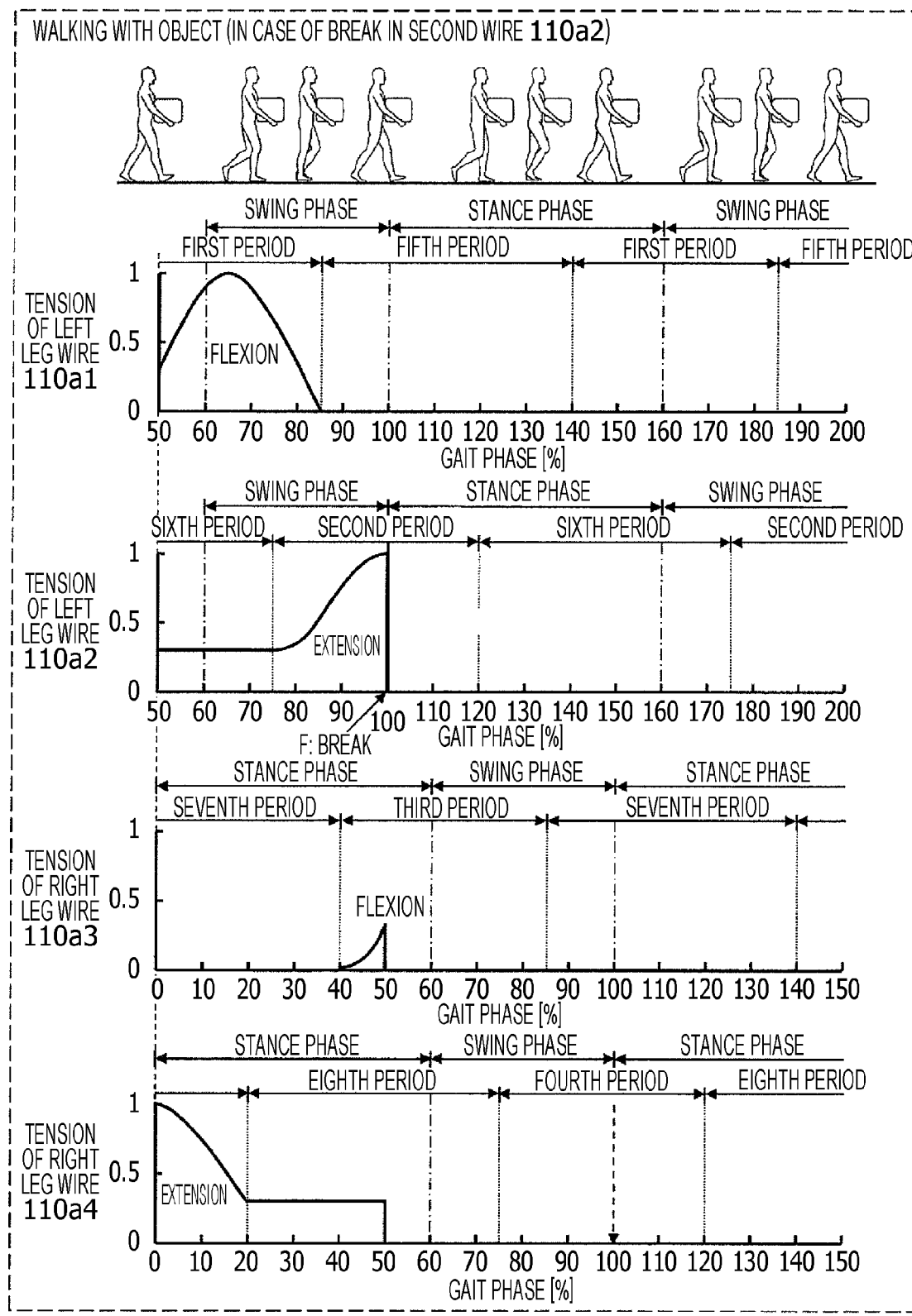
FIG. 34 is a diagram illustrating an example operation of the assistance apparatus according to the embodiment in the fourth pattern when a wire is broken during the operation in the second pattern in which an object is carried.

FIG. 34 illustrates an example operation of the assistance apparatus 100 in the fourth pattern when the wire 110a2 is broken during the operation in the second pattern in which an object is carried. As illustrated in FIG. 34, upon detection of a break in the wire 110a2 at a time point F during the operation in the second pattern, the drive control unit 122 stops the operation of the assistance apparatus 100. That is, the drive control unit 122 generates no tension in the wires 110a1, 110a3, and 110a4, which are not broken, at and after the break time point F. In the operation in the second pattern, the assistance apparatus 100 assists a user in walking with an object. In this case, to assist the user with the center of gravity of the body of the user, which tends to be moved forward, being kept at the center of gravity position in the upright posture of the user, the drive control unit 122 continuously generates a tension greater than or equal to the second threshold value and less than or equal to the fourth threshold value in the wires 110a2 and 110a4. However, due to the break in the wire 110a2, the assistance apparatus 100 is unable to continuously provide the assistance described above, and thus the drive control unit 122 stops the assistance apparatus 100 from providing assistance. For example, when the assistance apparatus 100 continuously provides assistance for flexion by using the wires 110a1 and 110a3 without generating a tension in the wires 110a2 and 110a4, the load imposed on the user may increase.

Figure 35:
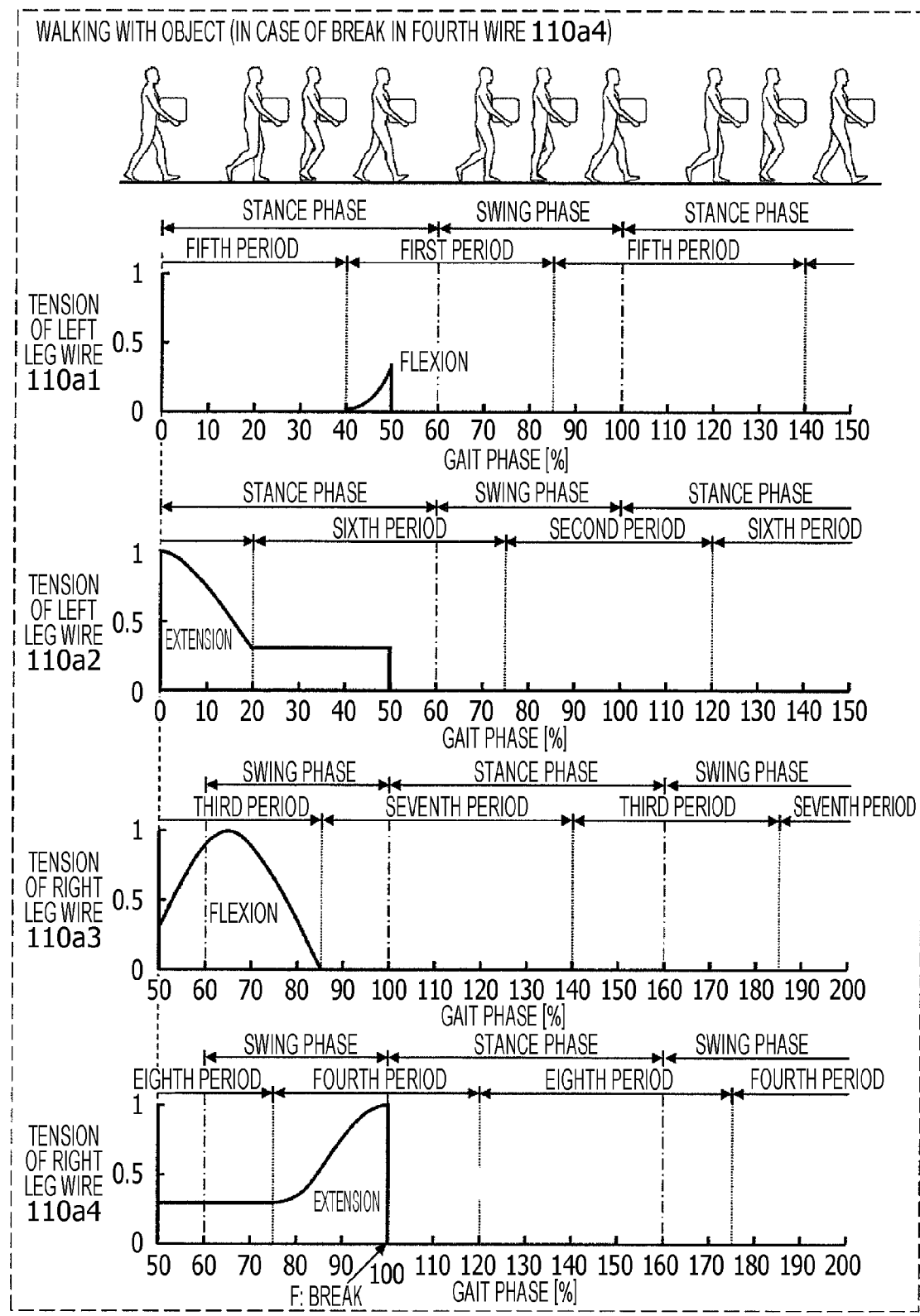
FIG. 35 is a diagram illustrating an example operation of the assistance apparatus according to the embodiment in the fourth pattern when a wire is broken during the operation in the second pattern in which an object is carried.

FIG. 35 illustrates an example operation of the assistance apparatus 100 in the fourth pattern when the wire 110a4 is broken during the operation in the second pattern in which an object is carried. In FIG. 35, as in FIG. 34, upon detection of a break in the wire 110a4 at a time point F during the operation in the second pattern, the drive control unit 122 stops the operation of the assistance apparatus 100. That is, the drive control unit 122 generates no tension in the wires 110a1, 110a3, and 110a2, which are not broken, at and after the break time point F.

Accordingly, when the wire 110a2 or 110a4 for assisting extension of a user who is walking with an object is broken, the assistance apparatus 100 stops providing assistance to the user.

3-4. Modification of Operation of Assistance Apparatus

In the respective operations of the assistance apparatuses 100 and 200 according to the embodiment and the modification, the same input profile of wire tension and the same maximum wire tension are set for all the wires 110 for assisting flexion and extension. However, the present disclosure is not limited to the embodiment and the modification described above. Since the moment arms of the hip joints and the lengths of the legs differ from one user to another, the assistance torque exerted on the hip joint differs depending on the user even when the same tension is applied to the same wire. The assistance torque is determined by an expression of wire tension×moment arm. Thus, different tensions may be applied to wires in accordance with the user. A fatter user has a larger moment arm of the hip joint than a thinner user. Thus, for example, the maximum wire tension may be set to 60 N for a fat user with a girth of 100 cm or more, whereas the maximum wire tension may be set to 120 N for a thin user with a girth or 70 cm or less. This may make assistance torques exerted on a fat user and a thin user equivalent.

In addition, the wire tension may change in accordance with the lengths of the legs of the user. In assistance for flexion and extension, since a vertical, or upward and downward, force component of wire tension is more largely exerted on a user with longer legs, the wire tension for a user with longer legs may be reduced. Adjusting the wire tension for each user in accordance with the body type and the leg length enables a comfortable assistance torque to be applied to each user.

In addition, the wire tensions on the front and back sides of the legs of the user are set to the same value. However, the present disclosure is not limited to the embodiment and the modification described above. For example, the tensions of the wires located on the front side of the legs may be greater than the tensions of the wires located on the back side of the legs. Since the wires on the back side pass through the buttocks of the user, the moment arm on the back side of the body of the user is greater than that on the front side of the body of the user. Accordingly, the assistance torque exerted on the hip joints on the back side of the body of the user is greater than that on the front side of the body of the user. Thus, by increasing the tension of the wires on the front side, the assistance apparatuses 100 and 200 can assist flexion and extension of the user on the front and back sides in a well-balanced manner.

The periods during which wire tensions are generated in the wires 110 for assistance for flexion and extension are equal to each other. However, the present disclosure is not limited to the embodiment and the modification described above. For example, in the example illustrated in FIG. 25, the period during which a wire tension for assisting flexion is generated and the period during which a wire tension for assisting extension of the same leg is generated overlap. To reduce the overlap period, the length of either of the periods may be reduced. In particular, the periods may be adjusted such that the period in which a wire tension greater than or equal to the first threshold value is generated during assistance for flexion does not overlap the period in which a wire tension greater than or equal to the first threshold value is generated during assistance for extension. This also applies to the examples illustrated in FIG. 26 to FIG. 35. This prevents the user from being confused by the simultaneous feeling of assistance for flexion and assistance for extension. The relationship between the period during which a wire tension for assisting flexion is generated and the period during which a wire tension for assisting extension is generated may be determined in accordance with the flexion and extension ability of the user.

In FIG. 25, FIG. 26, and FIG. 28 to FIG. 35, the waveforms of the input profiles of wire tensions are convex curve. However, the present disclosure is not limited to the illustrated examples. The waveforms of the input profiles illustrated in FIG. 25, FIG. 26, and FIG. 28 to FIG. 35 are waveforms obtained through experiments, which are waveforms that allow users to feel effective and comfortable when enjoying the benefits of assistance provided by the assistance apparatus 100. The input profiles of the wire tensions may be each created using, for example, a rectangular waveform, a trapezoidal waveform, a triangular waveform, a Gaussian waveform, or the like. When a rectangular waveform is used, the assistance apparatus 100 continuously generates a maximum tension during an entire period over which a wire tension is generated. When a trapezoidal waveform is used, the assistance apparatus 100 continuously generates a maximum tension during an entire period over which a wire tension is generated, except the initial and terminal periods. When each input profile is created using a waveform that is quadrangle such as a rectangular waveform and a trapezoidal waveform, a steep rise or a steep fall of the wire tension may occur. Such a change in tension may cause a user to feel uncomfortable during assistance. Thus, for example, when the waveform of each input profile is triangular, a rise of the wire tension to the maximum tension may be changed to a gentler one, with the wire tension changing gradually. Accordingly, the assistance apparatus 100 can carefully assist movements of the legs of the user, resulting in a reduction in the risk of falling of the user due to a steep change in wire tension.

In actual human walking, flexion and extension torques produced by the legs smoothly and continuously change. Thus, the waveform of each input profile may be implemented as a Gaussian waveform. The Gaussian waveform may be a waveform created by, for example, adding together, or superposing, Gaussian functions by using a Gaussian function given by Equation (1) below. In this case, among superposition methods of Gaussian functions, a superposition method that is closest to the waveform of a torque of the legs in actual human walking is found and applied to the generation of a waveform of an input profile. Finding such a method is also referred to as Gaussian fitting. Accordingly, assistance torques can be applied to realize walking similar to actual human walking, and more natural assistance can be achieved.

$$f(x) = \frac{1}{\sqrt{2\pi}\,\sigma}\exp\left\{-\frac{(x-\mu)^2}{2\sigma^2}\right\} \qquad (1)$$

Specifically, a Gaussian function has a pair of variables $\mu$ and $\sigma$ (also referred to as parameters), and the waveform of the Gaussian function depends on the two parameters. The time indicating a peak of a wave of the Gaussian function depends on the variable $\mu$, and the width of the wave of the Gaussian function depends on the variable $\sigma$. Thus, various Gaussian functions may be generated by using various combinations of values of the two parameters.

A function obtained by multiplying an amplitude of a torque generated in a leg during human walking by a Gaussian function forms a waveform that shows time (in seconds) on the horizontal axis and torque (in Nm) on the vertical axis. Examples of the amplitude include a maximum torque of a leg during human walking, and the amplitude is, for example, 20 Nm. Gaussian functions are superposed to find a superposition method that is closest to the torque-time waveform of the leg during actual human walking. At this time, Gaussian fitting is performed on actual human gait data by using n Gaussian functions $f_1(x), f_2(x), \ldots,$ and $f_n(x)$ having various values of the two parameters $\mu$ and $\sigma$ to obtain Gaussian functions. The obtained Gaussian functions are further superposed to obtain a new Gaussian function. By adjusting the two parameters $\mu$ and $\sigma$ of the new Gaussian function, an input profile of a wire tension can be created.

Further, the assistance apparatus 100 may change a maximum tension to be generated in a wire in accordance with the time of year when the user wears the assistance apparatus 100. For example, in summer when the user wears light clothes, the user's moment arm is shorter than in winter when the user wears thick clothes. Accordingly, even when the assistance apparatus 100 applies the same tension to a wire, the torque exerted on the leg of the user in summer is smaller than that in winter. Thus, for example, the assistance apparatus 100 may increase the tension to be applied to each wire in summer to, for example, 1.2 times that in winter.

The operation of the assistance apparatus 200 according to the modification illustrated in FIG. 13 to FIG. 21 is also similar to that of the assistance apparatus 100 according to the embodiment. For the operations described above, the wire tension control for the first wire 110a1 and the wire tension control for the fifth wire 110a5 of the assistance apparatus 200 are similar to the wire tension control for the wire 110a1 of the assistance apparatus 100. The wire tension control for the second wire 110a2 and the wire tension control for the sixth wire 110a6 of the assistance apparatus 200 are similar to the wire tension control for the wire 110a2 of the assistance apparatus 100. The wire tension control for the third wire 110a3 and the wire tension control for the seventh wire 110a7 of the assistance apparatus 200 are similar to the wire tension control for the wire 110a3 of the assistance apparatus 100. The wire tension control for the fourth wire 110a4 and the wire tension control for the eighth wire 110a8 of the assistance apparatus 200 are similar to the wire tension control for the wire 110a4 of the assistance apparatus 100.

When assisting flexion or extension, the assistance apparatus 200 generates tensions in two wires of the same leg at the same timing. Thus, the maximum tension to be generated in the first wire 110a1 and the maximum tension to be generated in the fifth wire 110a5 of the assistance apparatus 200 may be different from the maximum tension to be generated in the wire 110a1 of the assistance apparatus 100 and may be smaller than the maximum tension to be generated in the wire 110a1 of the assistance apparatus 100, for example. The maximum tension to be generated in the second wire 110a2 and the maximum tension to be generated in the sixth wire 110a6 of the assistance apparatus 200 may be different from the maximum tension to be generated in the wire 110a2 of the assistance apparatus 100 and may be smaller than the maximum tension to be generated in the wire 110a2 of the assistance apparatus 100, for example. The maximum tension to be generated in the third wire 110a3 and the maximum tension to be generated in the seventh wire 110a7 of the assistance apparatus 200 may be different from the maximum tension to be generated in the wire 110a3 of the assistance apparatus 100 and may be smaller than the maximum tension to be generated in the wire 110a3 of the assistance apparatus 100, for example. The maximum tension to be generated in the fourth wire 110a4 and the maximum tension to be generated in the eighth wire 110a8 of the assistance apparatus 200 may be different from the maximum tension to be generated in the wire 110a4 of the assistance apparatus 100 and may be smaller than the maximum tension to be generated in the wire 110a4 of the assistance apparatus 100, for example.

The relationship between the maximum tension to be generated in the first wire 110a1 and the maximum tension to be generated in the fifth wire 110a5 of the assistance apparatus 200 and the maximum tension to be generated in the wire 110a1 of the assistance apparatus 100 changes in accordance with the angle between the direction in which the wire 110a1 of the assistance apparatus 100 extends and the direction in which the first wire 110a1 of the assistance apparatus 200 extends and in accordance with the angle between the direction in which the wire 110a1 of the assistance apparatus 100 extends and the direction in which the fifth wire 110a5 of the assistance apparatus 200 extends, and can be determined in accordance with the angles. The relationship between the maximum tension to be generated in the second wire 110a2 and the maximum tension to be generated in the sixth wire 110a6 of the assistance apparatus 200 and the maximum tension to be generated in the wire 110a2 of the assistance apparatus 100 changes in accordance with the angle between the direction in which the wire 110a2 of the assistance apparatus 100 extends and the direction in which the second wire 110a2 of the assistance apparatus 200 extends and in accordance with the angle between the direction in which the wire 110a2 of the assistance apparatus 100 extends and the direction in which the sixth wire 110a6 of the assistance apparatus 200 extends, and can be determined in accordance with the angles. The relationship between the maximum tension to be generated in the third wire 110a3 and the maximum tension to be generated in the seventh wire 110a7 of the assistance apparatus 200 and the maximum tension to be generated in the wire 110a3 of the assistance apparatus 100 changes in accordance with the angle between the direction in which the wire 110a3 of the assistance apparatus 100 extends and the direction in which the third wire 110a3 of the assistance apparatus 200 extends and in accordance with the angle between the direction in which the wire 110a3 of the assistance apparatus 100 extends and the direction in which the seventh wire 110a7 of the assistance apparatus 200 extends, and can be determined in accordance with the angles. The relationship between the maximum tension to be generated in the fourth wire 110a4 and the maximum tension to be generated in the eighth wire 110a8 of the assistance apparatus 200 and the maximum tension to be generated in the wire 110a4 of the assistance apparatus 100 changes in accordance with the angle between the direction in which the wire 110a4 of the assistance apparatus 100 extends and the direction in which the fourth wire 110a4 of the assistance apparatus 200 extends and in accordance with the angle between the direction in which the wire 110a4 of the assistance apparatus 100 extends and the direction in which the eighth wire 110a8 of the assistance apparatus 200 extends, and can be determined in accordance with the angles.

The term "same timing" is used to include not only exactly the same timing but also different timings or timings with a difference. The difference may be less than 10% or may be 5% or less in terms of the value of the gait phase. For example, when the difference is 5% or less, the values at all timings in the gait phase are included in a range of values of the gait phase, which is within ±5% from an average value of values at the timings in the gait phase.

If both the wires 110a1 and 110a5 are broken or both the wires 110a3 and 110a7 are broken during the operation in the first or second pattern, the assistance apparatus 200 may perform the operation in the third pattern. For example, if both the wires 110a1 and 110a5 are broken, the assistance apparatus 200 controls wire tension for the pair of wires 110a2 and 110a6, the pair of wires 110a3 and 110a7, and the pair of wires 110a4 and 110a8 in a way similar to that for the wires 110a2, 110a3, and 110a4 illustrated in FIG. 28 or FIG. 30, respectively. If both the wires 110a3 and 110a7 are broken, the assistance apparatus 200 controls wire tension in a way similar to that illustrated in FIG. 29 or FIG. 31.

If either of the wires 110a1 and 110a5 is broken or either of the wires 110a3 and 110a7 is broken during the operation in the first or second pattern, the assistance apparatus 200 may continuously perform the operation in the first or second pattern or may perform the operation in the third pattern. Even if one of a pair of wires is broken, the assistance apparatus 200 can assist flexion of the left and right legs of the user by using the wire that is not broken. When performing the operation in the third pattern, the assistance apparatus 200 reduces the tension of an unbroken wire that is paired with a broken wire to a level smaller than the second threshold value at and after a break time point and controls wire tension in a way similar to that illustrated in FIG. 28 to FIG. 31.

If both the wires 110a2 and 110a6 are broken or both the wires 110a4 and 110a8 are broken during the operation in the first or second pattern, the assistance apparatus 200 may perform the operation in the fourth pattern and stop assistance. If either of the wires 110a2 and 110a6 is broken or either of the wires 110a4 and 110a8 is broken during the operation in the first or second pattern, the assistance apparatus 200 may continuously perform the operation in the first or second pattern or may perform the operation in the fourth pattern.

4. Example

An experiment was made for the assistance operation using the assistance apparatus 100 according to the embodiment in three patterns for comparison and verification. The operation in the first pattern, the operation in the second pattern, and an operation in a new fifth pattern were compared.

In the operation in the fifth pattern, the assistance apparatus 100 controlled wire tension for the wires 110a1 and 110a3 in a way similar to that for the operation in the first pattern and the operation in the second pattern. Further, the assistance apparatus 100 continuously generated a maximum tension in the wires 110a2 and 110a4 during the entire duration of the assistance. Thus, strong assistance forces for extension were continuously applied to both legs of the wearer of the assistance apparatus 100 all the time during the entire duration of the assistance.

In the operation in the second pattern, the tension to be generated in the wire 110a2 was set to 20% of the maximum tension during the sixth period in the gait phase of the left leg. Further, the tension to be generated in the wire 110a4 was set to 20% of the maximum tension during the eighth period in the gait phase of the right leg. The maximum tension to be generated in the wire 110 was set to 100 N in the operation in the first pattern, the operation in the second pattern, and the operation in the fifth pattern.

The experiment was conducted on four subjects, namely A to D. The subjects A, C, and D were males, and the subject B was female. All the subjects A to D wearing the assistance apparatus 100 received three types of assistance based on the operation in the first pattern, the operation in the second pattern, and the operation in the fifth pattern, while walking forward with luggage in both hands in front of the body. Then, the subjects A to D selected one optimum operation, which was the most comfortable walking operation, from among the operations in the three patterns. The selection results are given in Table 1 below. Table 1 indicates that the operation in the second pattern is the most effective to assist the wearer in walking forward while carrying luggage. Table 1 also indicates that the operation in the first pattern is also effective to assist the wearer in walking forward.

TABLE 1

Evaluation results of assistance based on operations in patterns

| Subject | First pattern | Second pattern | Fifth pattern |
|---------|---------------|----------------|---------------|
| A       |               | Optimum        |               |
| B       |               | Optimum        |               |
| C       |               | Optimum        |               |
| D       | Optimum       |                |               |

5. Other Embodiments

While an assistance apparatus and so on according to one or more aspects have been described in conjunction with an embodiment and a modification, the present disclosure is not limited to the embodiment and modification. Applications of various modifications conceived of by persons skilled in the art to this embodiment and modification and embodiments based on combinations of constituent elements in different embodiments and modifications may also be encompassed in the scope of one or more aspects as long as such applications or embodiments do not depart from the gist of the present disclosure.

For example, in the assistance apparatuses 100 and 200 according to the embodiment and modification, the timings at which the control unit 120 activates the motors 114 to generate tensions in the wires 110 and values of the gait phase regarding the input profiles of the tensions are not limited to the values described in the embodiment and modification. The timings and the values of the gait phase regarding the input profiles of the tensions may be different from those described in the embodiment and modification. For example, an error of several percent in terms of gait phase may occur.

In the assistance apparatuses 100 and 200 according to the embodiment and modification, each of the wires 110 is provided with a motor. However, the present disclosure is not limited to the embodiment and modification. One motor may be coupled to wires. For example, in the assistance apparatus 200, one motor may pull the wires 110a1 and 110a5. That is, the assistance apparatus 200 may include, for example, four motors so that one motor is provided for two wires.

In the assistance apparatuses 100 and 200 according to the embodiment and the modification, four wires or eight wires are used to couple the upper-body belt 111 to the knee belts 112a and 112b. That is, two wires or four wires are coupled to each knee belt. However, the number of wires to be coupled to each knee belt is not limited to that described above. Any number of wires more than one may be coupled to each knee belt. For example, the numbers of wires to be coupled to the front part and the back part of each knee belt may be different. Flexion of the left leg may mean flexion of the hip joint of the left leg. Flexion of the right leg may mean flexion of the hip joint of the right leg. Extension of the left leg may mean extension of the hip joint of the left leg. Extension of the right leg may mean extension of the hip joint of the right leg.

The present disclosure is applicable to an apparatus for assisting a user in changing direction.

What is claimed is:

1. An assistance apparatus comprising:
an upper-body belt to be worn on an upper half of a body of a user;
a left knee belt to be worn on a left knee of the user;
a right knee belt to be worn on a right knee of the user;
a first wire that couples the upper-body belt and the left knee belt to each other on or above a front part of the body of the user;
a second wire that couples the upper-body belt and the left knee belt to each other on or above a back part of the body of the user;
a third wire that couples the upper-body belt and the right knee belt to each other on or above the front part of the body of the user;
a fourth wire that couples the upper-body belt and the right knee belt to each other on or above the back part of the body of the user;
at least one motor;
a first sensor that detects at least a tension of the first wire and a tension of the third wire; and
a control circuit, wherein
$TL(i)$ is an ith gait cycle of a left leg of the user and $TR(i)$ is an ith gait cycle of a right leg of the user,
in first assistance for assisting the user in walking without an object,
the control circuit controls the at least one motor to generate
(i) a tension greater than or equal to a first threshold value in the first wire during a first period, the first period being a period from 35% to 90% of the $TL(i)$,
(ii) a tension greater than or equal to the first threshold value in the second wire during a second period, the second period being a period from 0% to 25% of the $TL(i)$ and a period from 65% to 100% of the $TL(i)$,
(iii) a tension greater than or equal to the first threshold value in the third wire during a third period, the third period being a period from of 35% to 90% of the $TR(i)$,
(iv) a tension greater than or equal to the first threshold value in the fourth wire during a fourth period, the fourth period being a period from 0% to 25% of the $TR(i)$ and a period from 65% to 100% of the $TR(i)$, (v) a tension less than a second threshold value in the first wire during a fifth period included in the TL(i), the fifth period and the first period being separate, (vi) a tension less than the second threshold value in the second wire during a sixth period included in the TL(i), the sixth period and the second period being separate, (vii) a tension less than the second threshold value in the third wire during a seventh period included in the TR(i), the seventh period and the third period being separate, and (viii) a tension less than the second threshold value in the fourth wire during an eighth period included in the TR(i), the eighth period and the fourth period being separate, the first threshold value is larger than the second threshold value, the control circuit detects at least a break in the first wire and a break in the third wire based on a sensor value of the first sensor, in response to detection of a break in the first wire, the control circuit controls the at least one motor to generate a tension in the second wire during the second period that appears first after a timing of the break in the first wire, the tension being less than a tension of the second wire in a period during which no break occurs in the first wire, and in response to detection of a break in the third wire, the control circuit controls the at least one motor to generate a tension in the fourth wire during the fourth period that appears first after a timing of the break in the third wire, the tension being less than a tension of the fourth wire in a period during which no break occurs in the third wire.

2. The assistance apparatus according to claim 1, wherein in second assistance for assisting the user in walking with an object, the control circuit controls the at least one motor to generate (i) a tension less than the second threshold value in the first wire during the fifth period, (ii) a tension greater than or equal to the second threshold value in the second wire during the sixth period, (iii) a tension less than the second threshold value in the third wire during the seventh period, and (iv) a tension greater than or equal to the second threshold value in the fourth wire during the eighth period, the tension of the second wire in the sixth period during the second assistance is greater than the tension of the second wire in the sixth period during the first assistance, and the tension of the fourth wire in the eighth period during the second assistance is greater than the tension of the fourth wire in the eighth period during the first assistance.

3. The assistance apparatus according to claim 2, wherein in the second assistance, the tension of the first wire in the fifth period is less than the tension of the second wire in the sixth period, and the tension of the third wire in the seventh period is less than the tension of the fourth wire in the eighth period.

4. The assistance apparatus according to claim 1, wherein the control circuit controls the at least one motor to generate (i) a tension in the second wire during the second period that appears second after the timing of the break in the first wire, the tension being equal to the tension of the second wire in the period during which no break occurs in the first wire, and (ii) a tension in the fourth wire during the fourth period that appears second after the timing of the break in the third wire, the tension being equal to the tension of the fourth wire in the period during which no break occurs in the third wire.

5. The assistance apparatus according to claim 1, wherein the control circuit controls the at least one motor to generate (i) a tension less than the second threshold value in the third wire during the third period after the timing of the break in the first wire, and (ii) a tension less than the second threshold value in the first wire during the first period after the timing of the break in the third wire.

6. The assistance apparatus according to claim 1, wherein the left leg shifts from a stance phase to a swing phase during the first period, the left leg shifts from the swing phase to the stance phase during the second period, the right leg shifts from the stance phase to the swing phase during the third period, and the right leg shifts from the swing phase to the stance phase during the fourth period.

7. The assistance apparatus according to claim 1, wherein the at least one motor includes a first motor, a second motor, a third motor, and a fourth motor, the first wire has a first end fixed to the left knee belt,
the first wire has a second end fixed to the first motor,
the second wire has a first end fixed to the left knee belt,
the second wire has a second end fixed to the second motor,
the third wire has a first end fixed to the right knee belt,
the third wire has a second end fixed to the third motor,
the fourth wire has a first end fixed to the right knee belt, and
the fourth wire has a second end fixed to the fourth motor.

8. The assistance apparatus according to claim 1, further comprising:

a fifth wire that couples the upper-body belt and the left knee belt to each other and that extends on or above the front part of the body of the user in a direction crossing a direction in which the first wire extends;

a sixth wire that couples the upper-body belt and the left knee belt to each other and that extends on or above the back part of the body of the user in a direction crossing a direction in which the second wire extends;

a seventh wire that couples the upper-body belt and the right knee belt to each other and that extends on or above the front part of the body of the user in a direction crossing a direction in which the third wire extends; and an eighth wire that couples the upper-body belt and the right knee belt to each other and that extends on or above the back part of the body of the user in a direction crossing a direction in which the fourth wire extends, wherein in the first assistance, the control circuit controls the at least one motor to generate (i) a tension greater than or equal to the first threshold value in the first wire and the fifth wire during the first period, (ii) a tension greater than or equal to the first threshold value in the second wire and the sixth wire during the second period, (iii) a tension greater than or equal to the first threshold value in the third wire and the seventh wire during the third period, (iv) a tension greater than or equal to the first threshold value in the fourth wire and the eighth wire during the fourth period, (v) a tension less than the second threshold value in the first wire and the fifth wire during the fifth period, (vi) a tension less than the second threshold value in the second wire and the sixth wire during the sixth period, (vii) a tension less than the second threshold value in the third wire and the seventh wire during the seventh period, and (viii) a tension less than the second threshold value in the fourth wire and the eighth wire during the eighth period.

9. The assistance apparatus according to claim 8, wherein in second assistance for assisting the user in walking with an object, the control circuit controls the at least one motor to generate (i) a tension less than the second threshold value in the first wire during the fifth period, (ii) a tension greater than or equal to the second threshold value in the second wire during the sixth period, (iii) a tension less than the second threshold value in the third wire during the seventh period, and (iv) a tension greater than or equal to the second threshold value in the fourth wire during the eighth period, the tension of the second wire in the sixth period during the second assistance is greater than the tension of the second wire in the sixth period during the first assistance, the tension of the fourth wire in the eighth period during the second assistance is greater than the tension of the fourth wire in the eighth period during the first assistance, and in the second assistance, the control circuit controls the at least one motor to generate (i) a tension less than the second threshold value in the first wire and the fifth wire during the fifth period, (ii) a tension greater than or equal to the second threshold value in the second wire and the sixth wire during the sixth period, (iii) a tension less than the second threshold value in the third wire and the seventh wire during the seventh period, and (iv) a tension greater than or equal to the second threshold value in the fourth wire and the eighth wire during the eighth period.

10. The assistance apparatus according to claim 1, wherein a time point of 50% of the TL(i) corresponds to a time point of 0% of the TR(i), and a time point of 50% of the TR(i) corresponds to a time point of 0% of the TL(i+1).

11. The assistance apparatus according to claim 1, further comprising a memory, wherein the memory stores a program for controlling the at least one motor, and the control circuit controls the at least one motor in accordance with the program.

12. The assistance apparatus according to claim 1, further comprising a second sensor that detects a gait cycle of the user, wherein the control circuit calculates the TL(i) and the TR(i) based on a sensor value of the second sensor.

13. The assistance apparatus according to claim 1, further comprising an interface device, wherein the control circuit accepts selection of an assistance method including the first assistance via the interface device, and the control circuit controls the at least one motor in accordance with the assistance method.

14. An assistance method for assisting a movement of a user by using wires attached to a body of the user, the assistance method comprising:

coupling, using a first wire among the wires, an upper-body belt and a left knee belt to each other on or above a front part of the body of the user, the upper-body belt being a belt to be worn on an upper half of the body of the user, the left knee belt being a belt to be worn on a left knee of the user;

coupling, using a second wire among the wires, the upper-body belt and the left knee belt to each other on or above a back part of the body of the user;

coupling, using a third wire among the wires, the upper-body belt and a right knee belt to each other on or above the front part of the body of the user, the right knee belt being a belt to be worn on a right knee of the user;

coupling, using a fourth wire among the wires, the upper-body belt and the right knee belt to each other on or above the back part of the body of the user;

TL(i) being an ith gait cycle of a left leg of the user and TR(i) being an ith gait cycle of a right leg of the user;

in first assistance for assisting the user in walking without an object, generating a tension greater than or equal to a first threshold value in the first wire during a first period, the first period being a period from 35% to 90% of the TL(i);

generating a tension greater than or equal to the first threshold value in the second wire during a second period, the second period being a period from 0% to 25% of the TL(i) and a period from 65% to 100% of the TL(i);

generating a tension greater than or equal to the first threshold value in the third wire during a third period, the third period being a period from 35% to 90% of the TR(i);

generating a tension greater than or equal to the first threshold value in the fourth wire during a fourth period, the fourth period being a period from 0% to 25% of the TR(i) and a period from 65% to 100% of the TR(i);

generating a tension less than a second threshold value in the first wire during a fifth period included in the TL(i), the fifth period and the first period being separate;

generating a tension less than the second threshold value in the second wire during a sixth period included in the TL(i), the sixth period and the second period being separate;

generating a tension less than the second threshold value in the third wire during a seventh period included in the TR(i), the seventh period and the third period being separate;

generating a tension less than the second threshold value in the fourth wire during an eighth period included in the TR(i), the eighth period and the fourth period being separate, the first threshold value being larger than the second threshold value;

acquiring a sensor value of a first sensor that detects at least a tension of the first wire and a tension of the third wire;

in response to detection of a break in the first wire, generating a tension in the second wire during the second period that appears first after a timing of the break in the first wire, the tension being less than a tension of the second wire in a period during which no break occurs in the first wire; and in response to detection of a break in the third wire, generating a tension in the fourth wire during the fourth period that appears first after a timing of the break in the third wire, the tension being less than a tension of the fourth wire in a period during which no break occurs in the third wire, wherein the tension of the first wire, the tension of the second wire, the tension of the third wire, and the tension of the fourth wire are adjusted by a motor that is controlled by at least one control circuit.

15. The assistance method according to claim 14, further comprising:
in second assistance for assisting the user in walking with an object,
generating a tension less than the second threshold value in the first wire during the fifth period;
generating a tension greater than or equal to the second threshold value in the second wire during the sixth period;
generating a tension less than the second threshold value in the third wire during the seventh period; and
generating a tension greater than or equal to the second threshold value in the fourth wire during the eighth period, wherein
the tension of the second wire in the sixth period during the second assistance is greater than the tension of the second wire in the sixth period during the first assistance, and
the tension of the fourth wire in the eighth period during the second assistance is greater than the tension of the fourth wire in the eighth period during the first assistance.

16. The assistance method according to claim 15, wherein in the second assistance,
the tension of the first wire in the fifth period is less than the tension of the second wire in the sixth period, and
the tension of the third wire in the seventh period is less than the tension of the fourth wire in the eighth period.

17. The assistance method according to claim 14, further comprising:
generating a tension in the second wire during the second period that appears second after the timing of the break in the first wire, the tension being equal to the tension of the second wire in the period during which no break occurs in the first wire; and
generating a tension in the fourth wire during the fourth period that appears second after the timing of the break in the third wire, the tension being equal to the tension of the fourth wire in the period during which no break occurs in the third wire.

18. The assistance method according to claim 14, further comprising:
generating a tension less than the second threshold value in the third wire during the third period after the timing of the break in the first wire; and
generating a tension less than the second threshold value in the first wire during the first period after the timing of the break in the third wire.

19. The assistance method according to claim 14, wherein
the left leg shifts from a stance phase to a swing phase during the first period,
the left leg shifts from the swing phase to the stance phase during the second period,
the right leg shifts from the stance phase to the swing phase during the third period, and
the right leg shifts from the swing phase to the stance phase during the fourth period.

20. The assistance method according to claim 14, wherein
a first end of the first wire is fixed to the left knee belt,
a second end of the first wire is fixed to a first motor among the at least one motor,
a first end of the second wire is fixed to the left knee belt,
a second end of the second wire is fixed to a second motor among the at least one motor,
a first end of the third wire is fixed to the right knee belt,
a second end of the third wire is fixed to a third motor among the at least one motor,
a first end of the fourth wire is fixed to the right knee belt, and
a second end of the fourth wire is fixed to a fourth motor among the at least one motor.

21. The assistance method according to claim 14, further comprising:
coupling, using a fifth wire among the wires, the upper-body belt and the left knee belt to each other, the fifth wire extending on or above the front part of the body of the user in a direction crossing a direction in which the first wire extends;
coupling, using a sixth wire among the wires, the upper-body belt and the left knee belt to each other, the sixth wire extending on or above the back part of the body of the user in a direction crossing a direction in which the second wire extends;
coupling, using a seventh wire among the wires, the upper-body belt and the right knee belt to each other, the seventh wire extending on or above the front part of the body of the user in a direction crossing a direction in which the third wire extends;
coupling, using an eighth wire among the wires, the upper-body belt and the right knee belt to each other, the eighth wire extending on or above the back part of the body of the user in a direction crossing a direction in which the fourth wire extends;
in the first assistance,
generating a tension greater than or equal to the first threshold value in the first wire and the fifth wire during the first period;
generating a tension greater than or equal to the first threshold value in the second wire and the sixth wire during the second period;
generating a tension greater than or equal to the first threshold value in the third wire and the seventh wire during the third period;

generating a tension greater than or equal to the first threshold value in the fourth wire and the eighth wire during the fourth period;
generating a tension less than the second threshold value in the first wire and the fifth wire during the fifth period;
generating a tension less than the second threshold value in the second wire and the sixth wire during the sixth period;
generating a tension less than the second threshold value in the third wire and the seventh wire during the seventh period; and
generating a tension less than the second threshold value in the fourth wire and the eighth wire during the eighth period.

22. The assistance method according to claim 21, further comprising:
in second assistance for assisting the user in walking with an object,
generating a tension less than the second threshold value in the first wire during the fifth period;
generating a tension greater than or equal to the second threshold value in the second wire during the sixth period;
generating a tension less than the second threshold value in the third wire during the seventh period;
generating a tension greater than or equal to the second threshold value in the fourth wire during the eighth period,
the tension of the second wire in the sixth period during the second assistance being greater than the tension of the second wire in the sixth period during the first assistance,
the tension of the fourth wire in the eighth period during the second assistance being greater than the tension of the fourth wire in the eighth period during the first assistance;
in the second assistance,
generating a tension less than the second threshold value in the first wire and the fifth wire during the fifth period;
generating a tension greater than or equal to the second threshold value in the second wire and the sixth wire during the sixth period;
generating a tension less than the second threshold value in the third wire and the seventh wire during the seventh period; and
generating a tension greater than or equal to the second threshold value in the fourth wire and the eighth wire during the eighth period.

23. The assistance method according to claim 14, wherein
a time point of 50% of the TL(i) corresponds to a time point of 0% of the TR(i), and
a time point of 50% of the TR(i) corresponds to a time point of 0% of the TL(i+1).

24. The assistance method according to claim 14, further comprising:
acquiring a sensor value of a second sensor that detects a gait cycle of the user; and
calculating the TL(i) and the TR(i) based on the sensor value of the second sensor.

25. The assistance method according to claim 14, further comprising:
accepting selection of an assistance method including the first assistance via an interface device; and
generating a tension in the first wire, the second wire, the third wire, and the fourth wire in accordance with the assistance method.

26. A recording medium storing a control program for causing a device including a processor to execute a process, the recording medium being a non-volatile, computer-readable medium,
a first wire coupling an upper-body belt and a left knee belt to each other on or above a front part of a body of a user, the upper-body belt being a belt to be worn on an upper half of the body of the user, the left knee belt being a belt to be worn on a left knee of the user,
a second wire coupling the upper-body belt and the left knee belt to each other on or above a back part of the body of the user,
a third wire coupling the upper-body belt and a right knee belt to each other on or above the front part of the body of the user, the right knee belt being a belt to be worn on a right knee of the user,
a fourth wire coupling the upper-body belt and the right knee belt to each other on or above the back part of the body of the user,
TL(i) being an ith gait cycle of a left leg of the user and TR(i) being an ith gait cycle of a right leg of the user,
the process comprising:
when assisting the user in walking without an object,
causing at least one motor to generate a tension greater than or equal to a first threshold value in the first wire during a first period, the first period being a period from 35% to 90% of the TL(i);
causing the at least one motor to generate a tension greater than or equal to the first threshold value in the second wire during a second period, the second period being a period from 0% to 25% of the TL(i) and a period from 65% to 100% of the TL(i);
causing the at least one motor to generate a tension greater than or equal to the first threshold value in the third wire during a third period, the third period being a period from 35% to 90% of the TR(i);
causing the at least one motor to generate a tension greater than or equal to the first threshold value in the fourth wire during a fourth period, the fourth period being a period from 0% to 25% of the TR(i) and a period from 65% to 100% of the TR(i);
causing the at least one motor to generate a tension less than a second threshold value in the first wire during a fifth period included in the TL(i), the fifth period and the first period being separate;
causing the at least one motor to generate a tension less than the second threshold value in the second wire during a sixth period included in the TL(i), the sixth period and the second period being separate;
causing the at least one motor to generate a tension less than the second threshold value in the third wire during a seventh period included in the TR(i), the seventh period and the third period being separate;
causing the at least one motor to generate a tension less than the second threshold value in the fourth wire during an eighth period included in the TR(i), the eighth period and the fourth period being separate,
the first threshold value being larger than the second threshold value;
acquiring a sensor value of a first sensor that detects at least a tension of the first wire and a tension of the third wire;
in response to detection of a break in the first wire, generating a tension in the second wire during the second period that appears first after a timing of the break in the first wire, the tension being less than a tension of the second wire in a period during which no break occurs in the first wire; and in response to detection of a break in the third wire, generating a tension in the fourth wire during the fourth period that appears first after a timing of the break in the third wire, the tension being less than a tension of the fourth wire in a period during which no break occurs in the third wire.

27. An assistance apparatus, comprising:
a first belt to be worn on an upper half of a body of a user;
a left knee belt to be worn above a left knee of the user;
a first wire coupling the first belt with the left knee belt on or above a front part of the body;
a second wire coupling the first belt with the left knee belt on or above a back part of the body;
a motor;
a first sensor that detects a tension on the first wire;
a second sensor that detects a tension on the second wire; and
a control circuit,
  wherein the control circuit detects whether the first wire is broken down based on an output value from the first sensor,
  wherein the control circuit detects whether the second wire is broken down based on an output value from the first sensor,
  wherein $TL(i)$ is an ith gait cycle of a left leg of the user and $TR(i)$ is an ith gait cycle of a right leg of the user,
  wherein when the control circuit detects the first wire and the second wire are not broken down, the control circuit, by using the motor, generates
    (a) a first tension on the first wire in a first period being from a first percent of the $TL(i)$ to a second percent of the $TL(i)$, the first percent being from 35 percent to 55 percent, the second percent being from 80 percent to 90 percent, a maximum magnitude of the first tension being a first threshold value or more,
    (b) a second tension on the second wire in a second period being from zero percent of the $TL(i)$ to a third percent of the $TL(i)$ and a third period being from a fourth percent of the $TL(i)$ to 100 percent of the $TL(i)$, the third percent being from 10 percent to 25 percent, the fourth percent being from 65 to 90 percent, a maximum magnitude of the second tension being the first threshold value or more,
    (c) a third tension on the third wire in a fourth period being from a fifth percent of the $TR(i)$ to a sixth percent of the $TR(i)$, the fifth percent being from 35 percent to 55 percent, the sixth percent being from 80 percent to 90 percent, a maximum magnitude of the third tension being the first threshold value or more, the $TR(i)$ being provided between zero percent of the $TL(i)$ and zero percent of $TL(i+1)$,
    (d) a fourth tension on the fourth wire in a fifth period being from zero percent of the $TR(i)$ to a seventh percent of the $TR(i)$ and a sixth period being from an eighth percent of the $TR(i)$ to 100 percent of the $TR(i)$, the seventh percent being from 10 percent to 25 percent, the eighth percent being from 65 percent to 90 percent, a maximum magnitude of the fourth tension being the first threshold value or more,
    (e) a fifth tension on the first wire during a ninth period included in the $TL(i)$ the first period and the ninth period being separate, a maximum magnitude of the fifth tension being a second threshold value or less,
    (f) a sixth tension on the second wire during a tenth period included in the $TL(i)$ the second period and the tenth period being separate, the third period and the tenth period being separate, a maximum magnitude of the sixth tension being the second threshold value or less,
    (g) a seventh tension on the third wire during an eleventh period included in the $TR(i)$ the fourth period and the eleventh period being separate, a maximum magnitude of the seventh tension being the second threshold value or less, and
    (h) an eighth tension on the fourth wire during a twelfth period included in the $TR(i)$ the fifth period and the twelfth period being separate, the sixth period and the twelfth period being separate, a maximum magnitude of the eighth tension being the second threshold value or less, and
  wherein when the control circuit detects the first wire is broken down and the second wire is not broken down in a period in the $TL(i)$ before a start of the second period included in the $TL(i)$, the control circuit, by using the motor, generates
    (i) a ninth tension on the second wire in the fourth period and a period being from zero percent of the $TL(i+1)$ to the third percent of the $TL(i+1)$, a maximum magnitude of the ninth tension being a third threshold value or more, the third threshold value being less than the first threshold value, and
    (j) a tenth tension on the second wire in a period included being from the fourth percent of the $TL(i+1)$ to the third percent of $TL(i+2)$, a maximum magnitude of the tenth tension being the first threshold value or more.

* * * * *